US012799507B2

(12) United States Patent
Boundy-Mills et al.

(10) Patent No.: US 12,799,507 B2
(45) **Date of Patent: *Nov. 17, 2026**

(54) METHODS OF PRODUCING POLYOL LIPIDS

(71) Applicant: THE REGENTS OF THE UNIVERSITY OF CALIFORNIA, Oakland, CA (US)

(72) Inventors: Kyria Boundy-Mills, Davis, CA (US); Luis Antonio Garay Almada, Davis, CA (US); Irnayuli Rosaleida Sitepu, Davis, CA (US); J. Bruce German, Davis, CA (US); Tomas Cajka, Davis, CA (US); Oliver Fiehn, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/676,643

(22) Filed: May 29, 2024

(65) Prior Publication Data

US 2024/0384313 A1 Nov. 21, 2024

Related U.S. Application Data

(60) Continuation of application No. 17/846,733, filed on Jun. 22, 2022, now Pat. No. 12,031,173, which is a division of application No. 16/164,764, filed on Oct. 18, 2018, now Pat. No. 11,401,539, which is a continuation of application No. PCT/US2017/028670, filed on Apr. 20, 2017.

(60) Provisional application No. 62/325,859, filed on Apr. 21, 2016.

(51) Int. Cl.

| | |
|---|---|
| ***C12P 7/6436*** | (2022.01) |
| ***C07H 15/04*** | (2006.01) |
| ***C12N 1/145*** | (2026.01) |
| ***C12N 1/16*** | (2026.01) |
| ***C12P 19/44*** | (2006.01) |
| ***C12R 1/645*** | (2006.01) |

(52) U.S. Cl.

CPC ............ *C12P 7/6436* (2013.01); *C07H 15/04* (2013.01); *C12N 1/145* (2021.05); *C12N 1/16* (2013.01); *C12P 19/44* (2013.01); *C12R 2001/645* (2021.05)

(58) Field of Classification Search

CPC ........ C12P 7/6436; C12P 19/44; C07H 15/04; C12N 1/145; C12N 1/16; C12R 2001/645; C12R 2001/64

See application file for complete search history.

(56) References Cited

U.S. PATENT DOCUMENTS

| | | | |
|---|---|---|---|
| 4,297,340 | A | 10/1981 | Abe |
| 11,401,539 | B2 | 8/2022 | Boundy-Mills |
| 12,031,173 | B2 | 7/2024 | Boundy-Mills |
| 2011/0136110 | A1 | 6/2011 | Van Bogaert |
| 2012/0022241 | A1 | 1/2012 | Gross |
| 2013/0072414 | A1 | 3/2013 | Price |
| 2019/0119707 | A1 | 4/2019 | Boundy-Mills |
| 2022/0325305 | A1 | 10/2022 | Boundy-Mills |

FOREIGN PATENT DOCUMENTS

| | | | |
|---|---|---|---|
| WO | 2007073371 | A1 | 6/2007 |
| WO | 2011127101 | | 10/2011 |
| WO | 2015075443 | A1 | 5/2015 |
| WO | 2015142736 | A1 | 9/2015 |
| WO | 2015153476 | A1 | 10/2015 |
| WO | 2017184884 | A1 | 10/2017 |

OTHER PUBLICATIONS

ISA/US, United States Patent and Trademark Office (USPTO), international search report and written opinion issued Jul. 14, 2017, related PCT international application No. PCT/US2017/028670, pp. 1-10, claims searched, pp. 11-30.
Sitepu, Irnayuli R. et al., "Manipulation of culture conditions alters lipid content and fatty acid profiles of a wide variety of known and new oleaginous yeasts species", Bioresource Technology 144 (2013) 360-369, available online Jun. 28, 2013.
Morita, Tomotake et al., "Analysis of expressed sequence tags from the anamorphic basidiomycetous yeast, *Pseudozyma antartica*, which produces glycolipid biosurfactants mannosylerythritol lipids", Wiley InterScience, 23, 2006, pp. 661-671.
Spencer, J. F. T. et al., "Non-conventional yeasts", Appl. Microbiol Biotechnoly, vol. 58, 2002, pp. 147-156.
Morita, Tomotake et al., "Microbial Conversion of Glycerol into Glycolipid Biosurfactants, Mannosylerthritol Lipids, by a Basidiomycete Yeast, *Pseudozyma antartica* JCM 10317r", Journal of Bioscience and Engineering, Vo. 104, No. 1, 78, 2007, pp. 78-81.
Wikipedia, Rhodotorula glutinis according to Wikipedia, https://en.wikipedia.org/wiki/Rhodotorula_glutinis, downloaded on May 17, 2021, 4 pages.
Ashby, Richard D., et al., "A Process Model for Approximating the Production Costs of the Fermentative Synthesis of Sophorolipids", J. Surfact Deterg., vol. 16, pp. 683-691, 2013.
Kurosawa, Takafumi, et al., 1994) "Extracellular Accumulation of the Polyol Lipids, 3,5-Dihydroxydecanoyl and 5-Hydroxy-2-decenoyl Esters of Arabitol and Mannitol, by *Aureobasidium* sp", Bioscience, Biotechnology, and Biochemistry, vol. 58, No. 11, Jun. 12, 2014, pp. 2057-2060, DOI: 10.1271/bbb.58.2057.
Deinema, Maria H., "Intra-and Extra-Cellular Lipid Production By Yeasts", Veenman, No. 61, 2, 1961, pp. 1-58.
Manitchotpisit, Pennapa, et al. "Heavy oils produced by Aureobasidium pullulans." Biotechnology Letters, vol. 33, 2011, pp. 1151-1157.
Nunez, Alberto, et al. "LC/MS analysis and lipase modification of the sophorolipids produced by Rhodotorula bogoriensis", Biotechnology Letters, vol. 26, 2004, pp. 1087-1093.

(Continued)

*Primary Examiner* — Kade Ariani
(74) *Attorney, Agent, or Firm* — O'BANION & RITCHEY LLP; John P. O'Banion

(57) ABSTRACT

Provided are methods and yeast cultures for producing polyol lipids and polyol lipid compositions.

8 Claims, 17 Drawing Sheets

(56) References Cited

OTHER PUBLICATIONS

Price, Neil PJ, et al. "Structural characterization of novel extracellular liamocins (mannitol oils) produced by Aureobasidium pullulans strain NRRL 50380", Carbohydrate Research, vol. 370, 2013, pp. 24-32.
Stodola, Frank H., et al., "Extracellular lipids of yeasts", Bacteriological Reviews, vol. 31, No. 3, 1967, pp. 194-213.
Suutar, M., P. Priha, et al., "Temperature shifts in regulation of lipids accumulated by Lipomyces starkeyi", Journal of the American Oil Chemists' Society, vol. 70, 1993, pp. 891-894.
Tulloch, A. P., et al., "Extracellular glycolipids of *Rhodotorula* species: the isolation and synthesis of 3-d-hydroxypalmitic and 3-d-hydroxystearic acids", Canadian Journal of Chemistry, vol. 42, No. 4 , 1964, pp. 830-835.
Tulloch, A. P., et al., "A new hydroxy fatty acid sophoroside from Candida bogoriensis." Canadian Journal of Chemistry, vol. 46, No. 3, 1968, pp. 345-348.
Van Bogaert, Inge NA, et al. "Microbial production and application of sophorolipids", Applied Microbiology and Biotechnology, vol. 76, 2011, pp. 23-34.
Sitepu, Irnayuli R. et al., "Manipulation of culture conditions alters lipid content and fatty acid profiles of a wide variety of known and new oleaginous yeasts species", Bioresource Technology, vol. 144, Sep. 2013, pp. 360-369, published online Jun. 28, 2013 (Bioresour Technol. Sep. 2013; 144: 10.1016/j.biortech.2013.06.047), NIH Public Access, Author Manuscript, available in PMC Sep. 1, 2014.

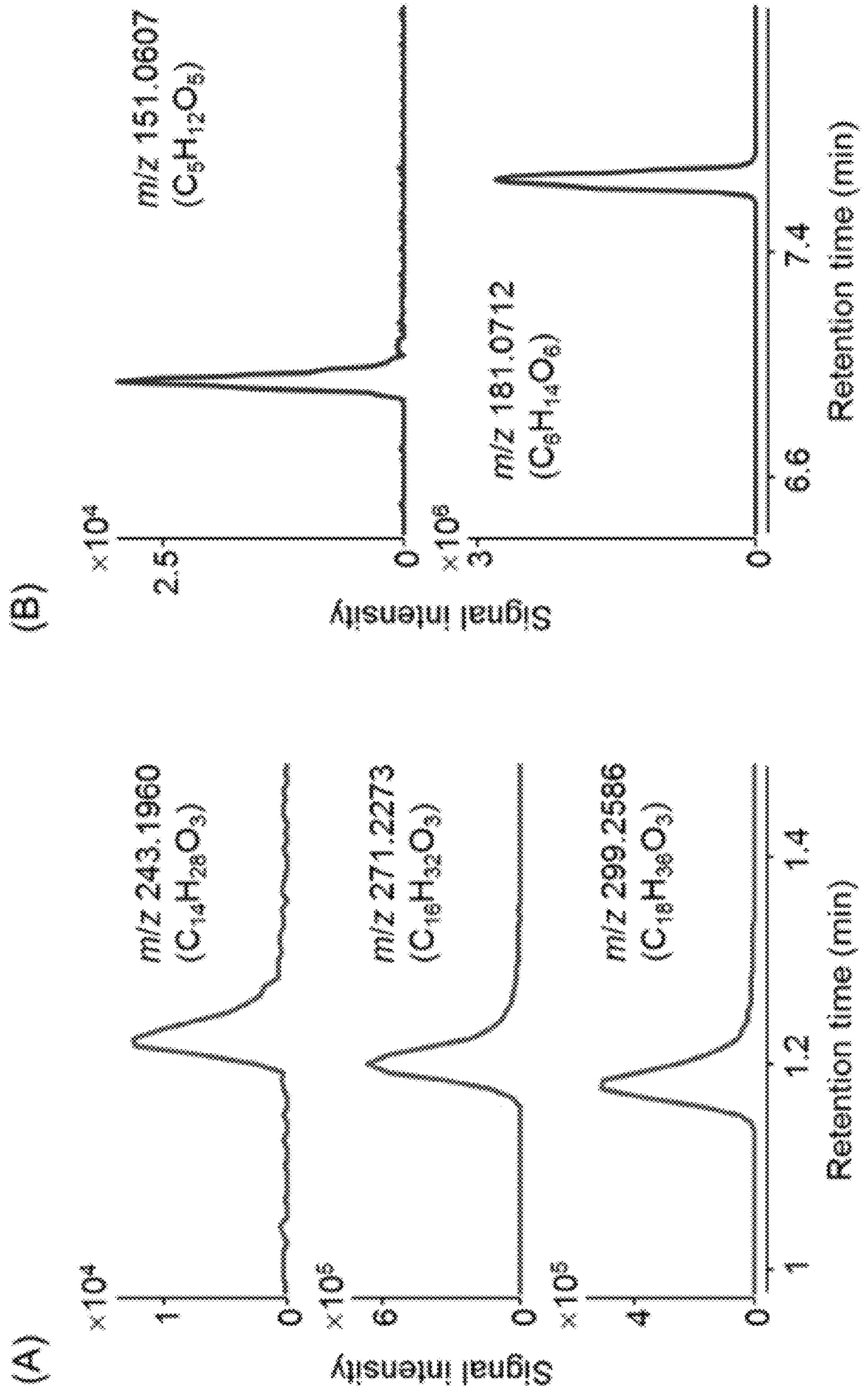
*Fig. 6A-B*

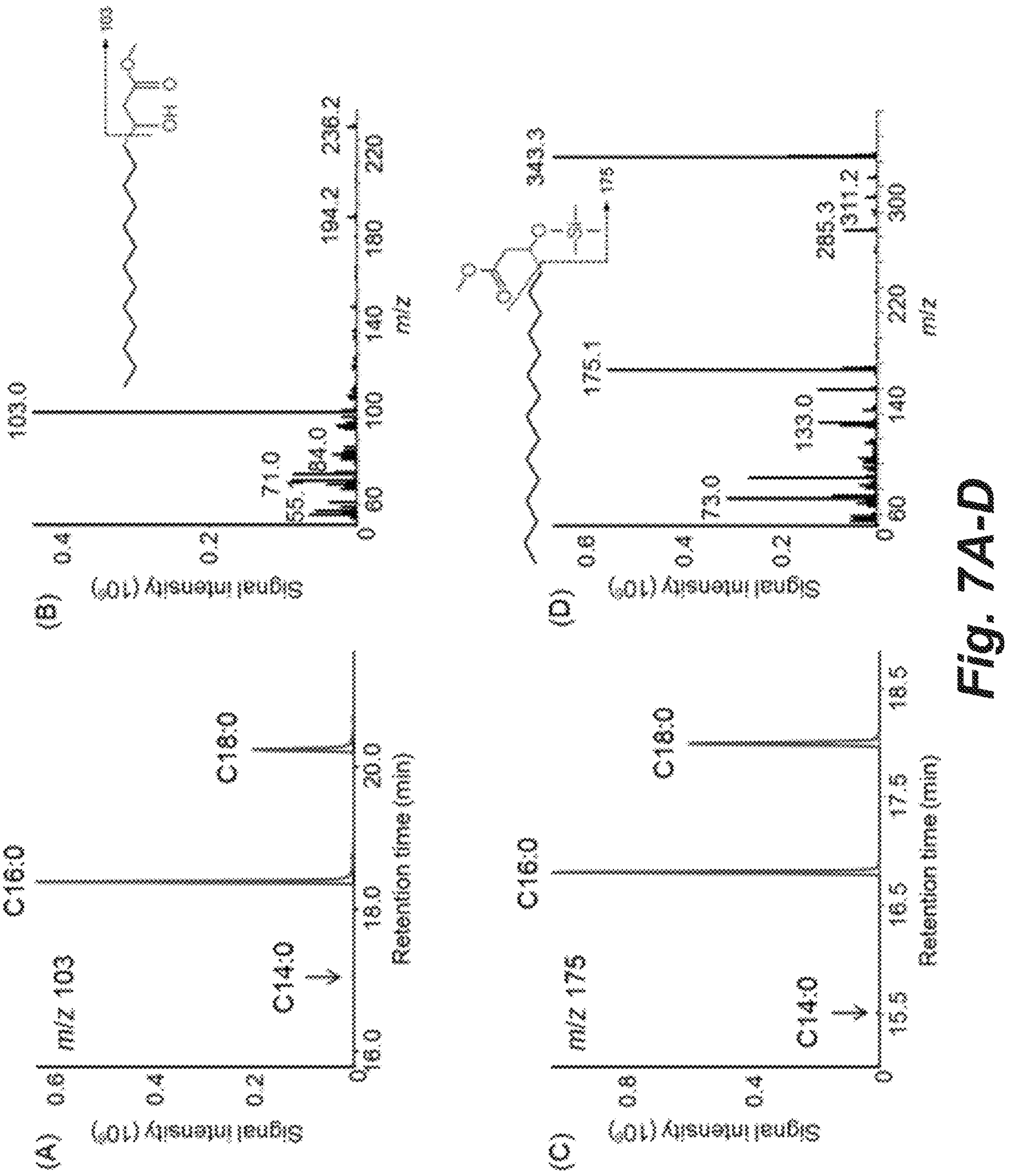
Fig. 7A-D

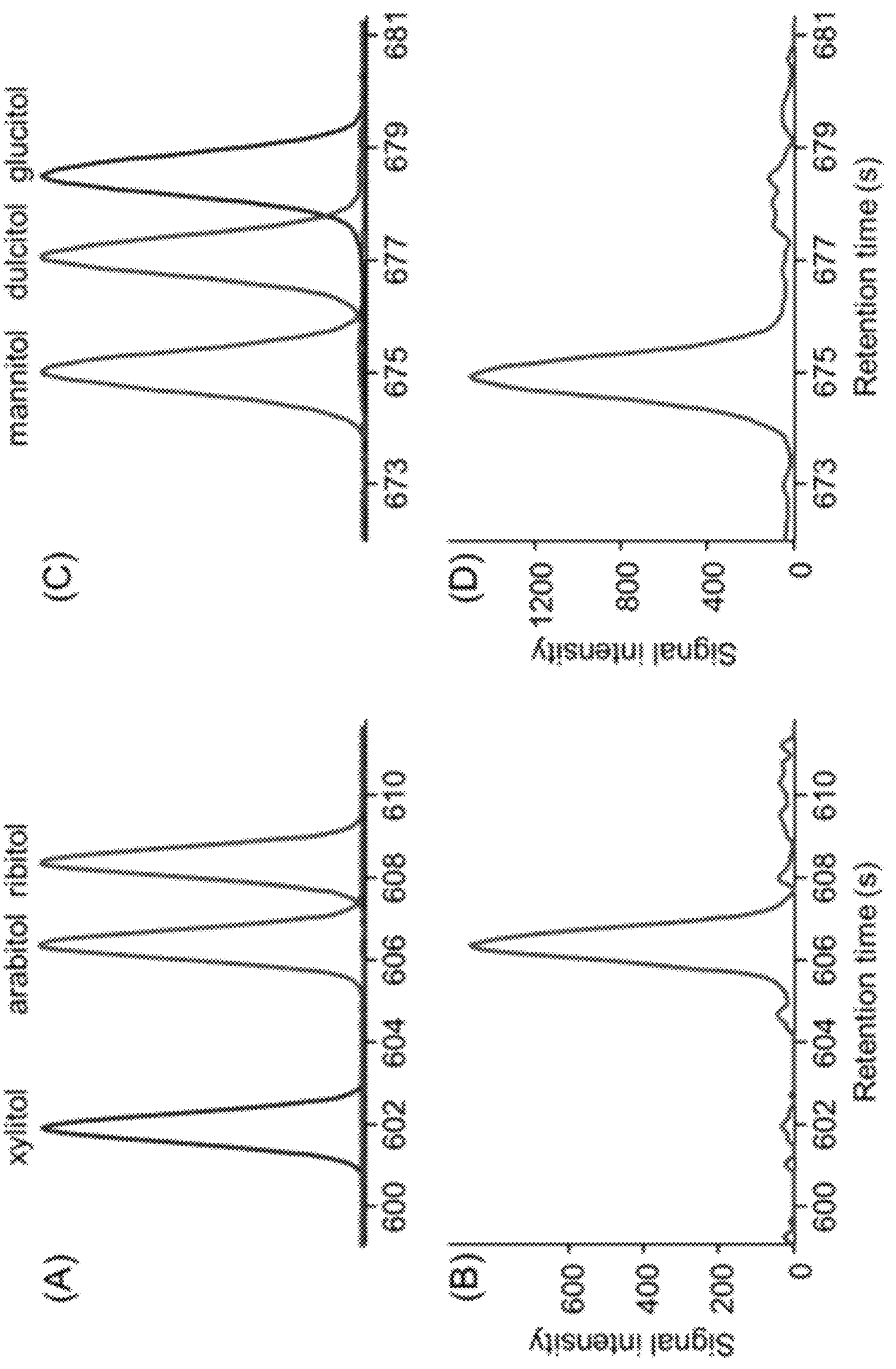
*Fig. 8A-D*

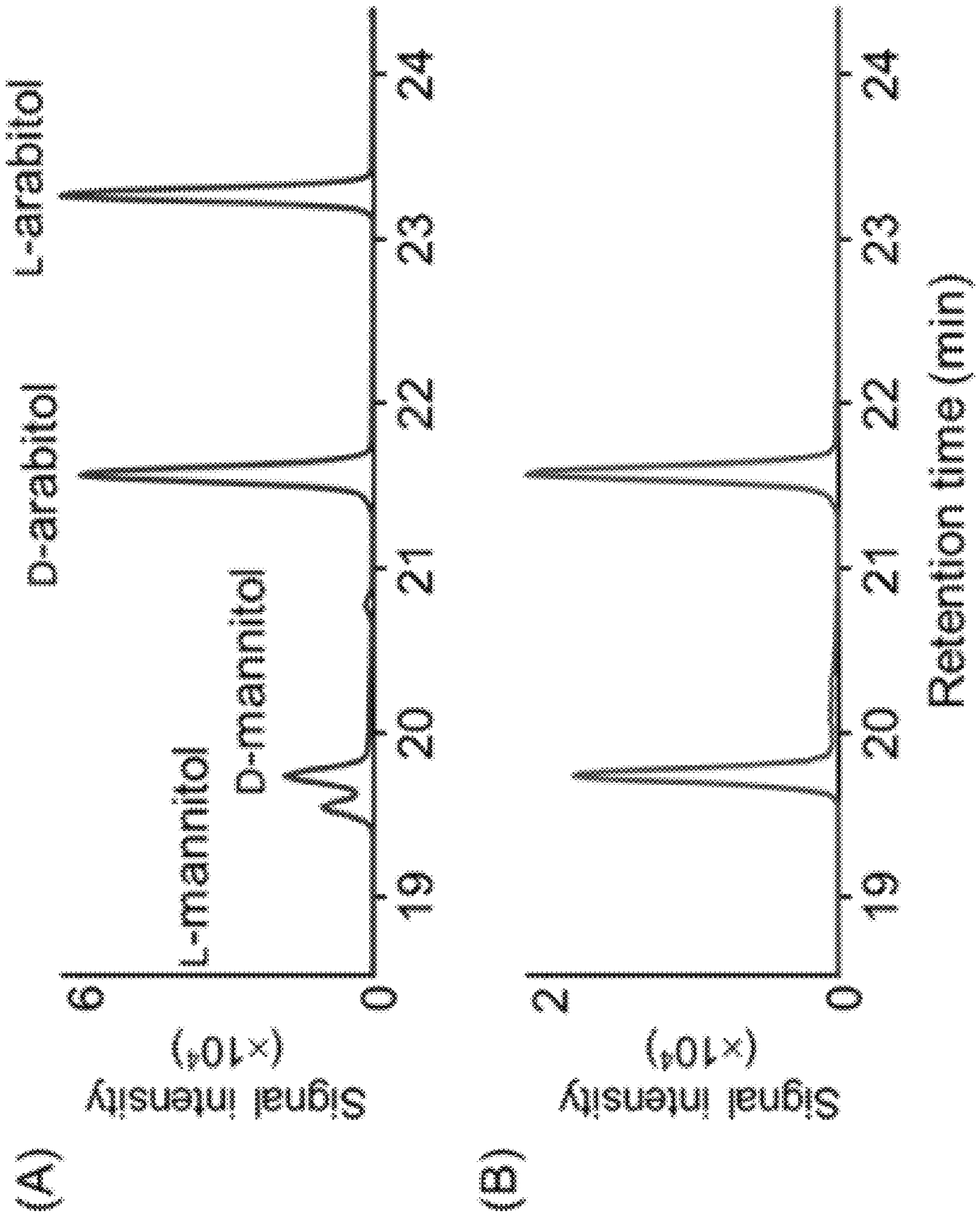
*Fig. 9A-B*

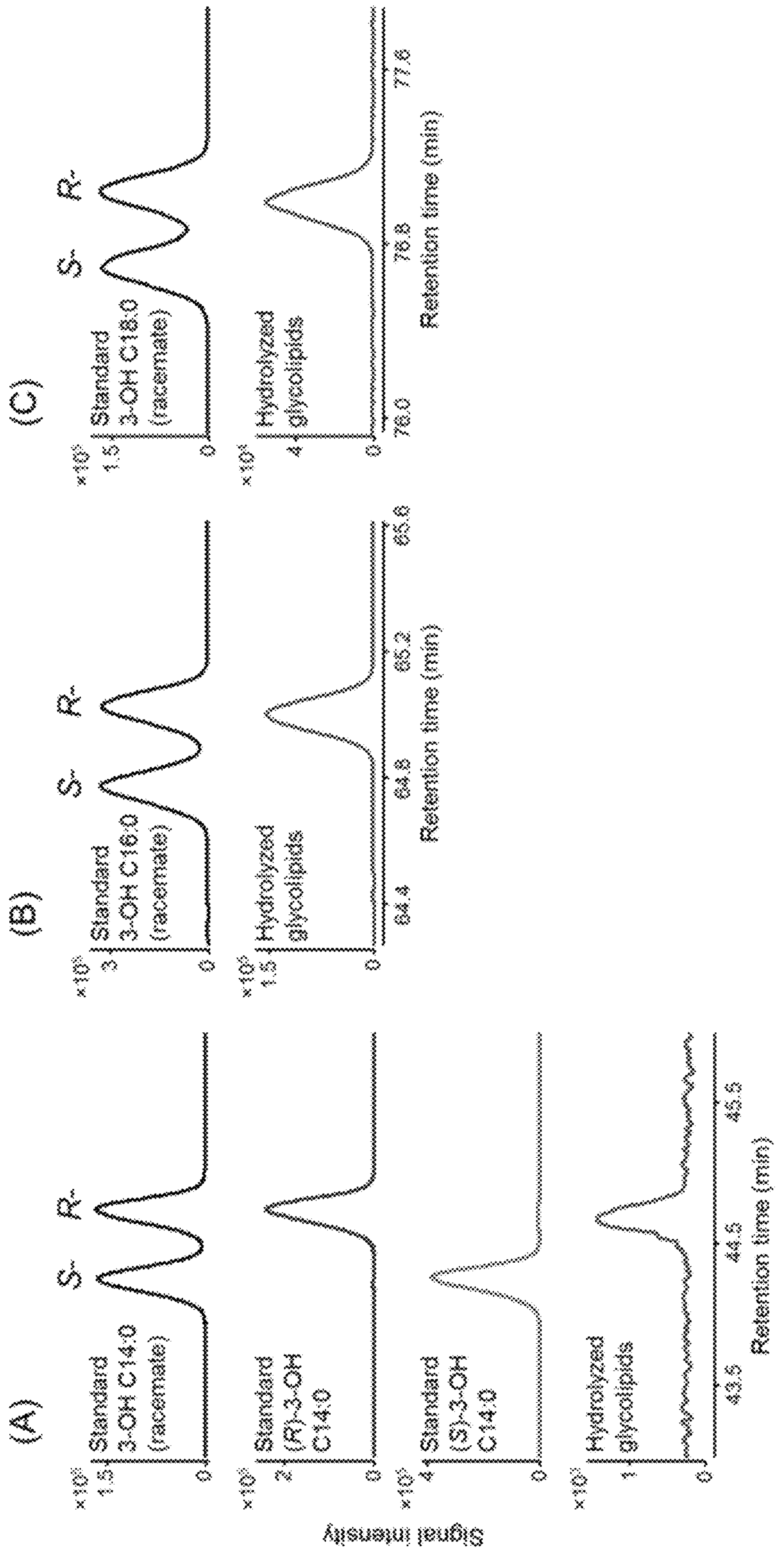
Fig. 10A-C

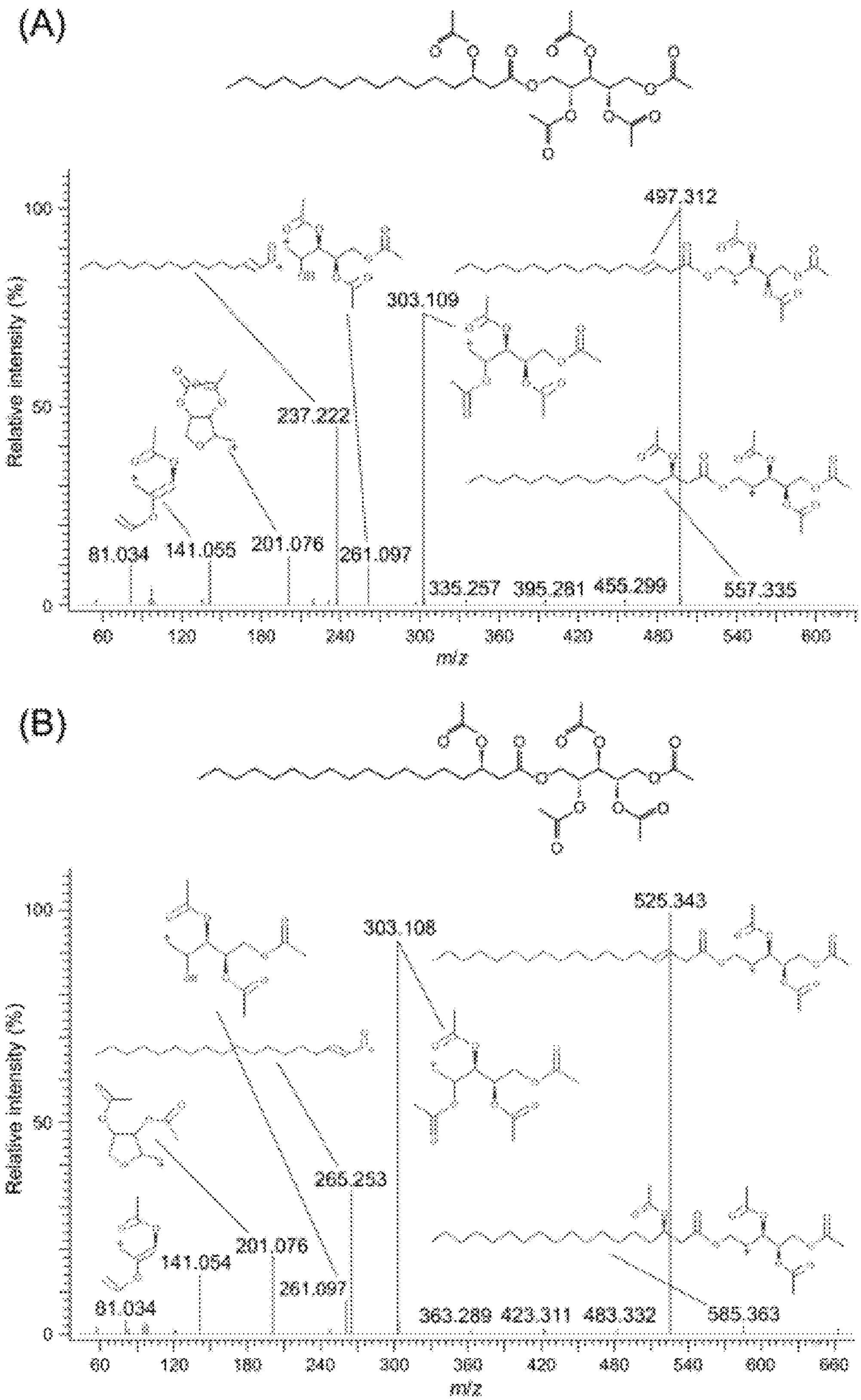
*Fig. 11A-B*

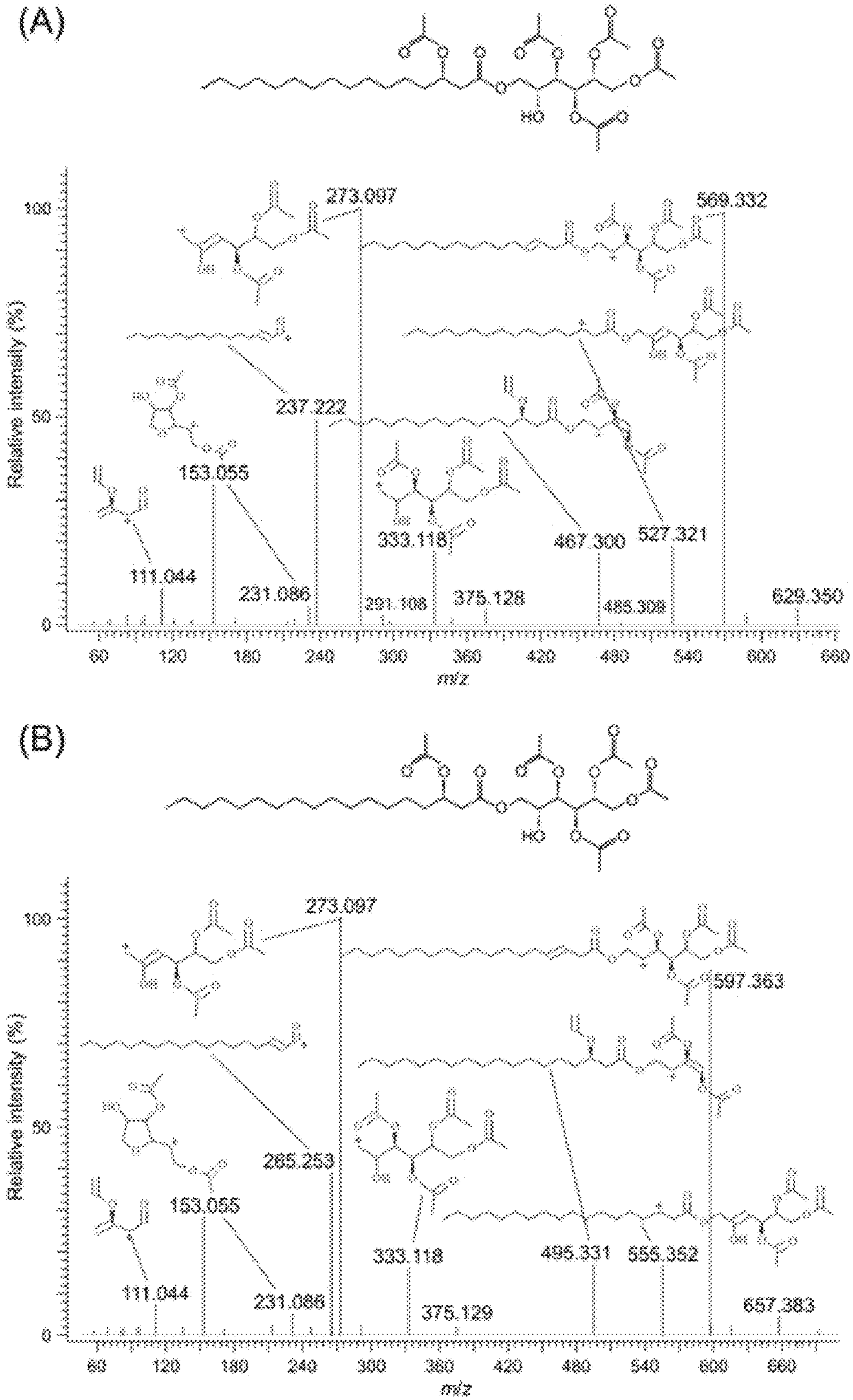
*Fig. 12A-B*

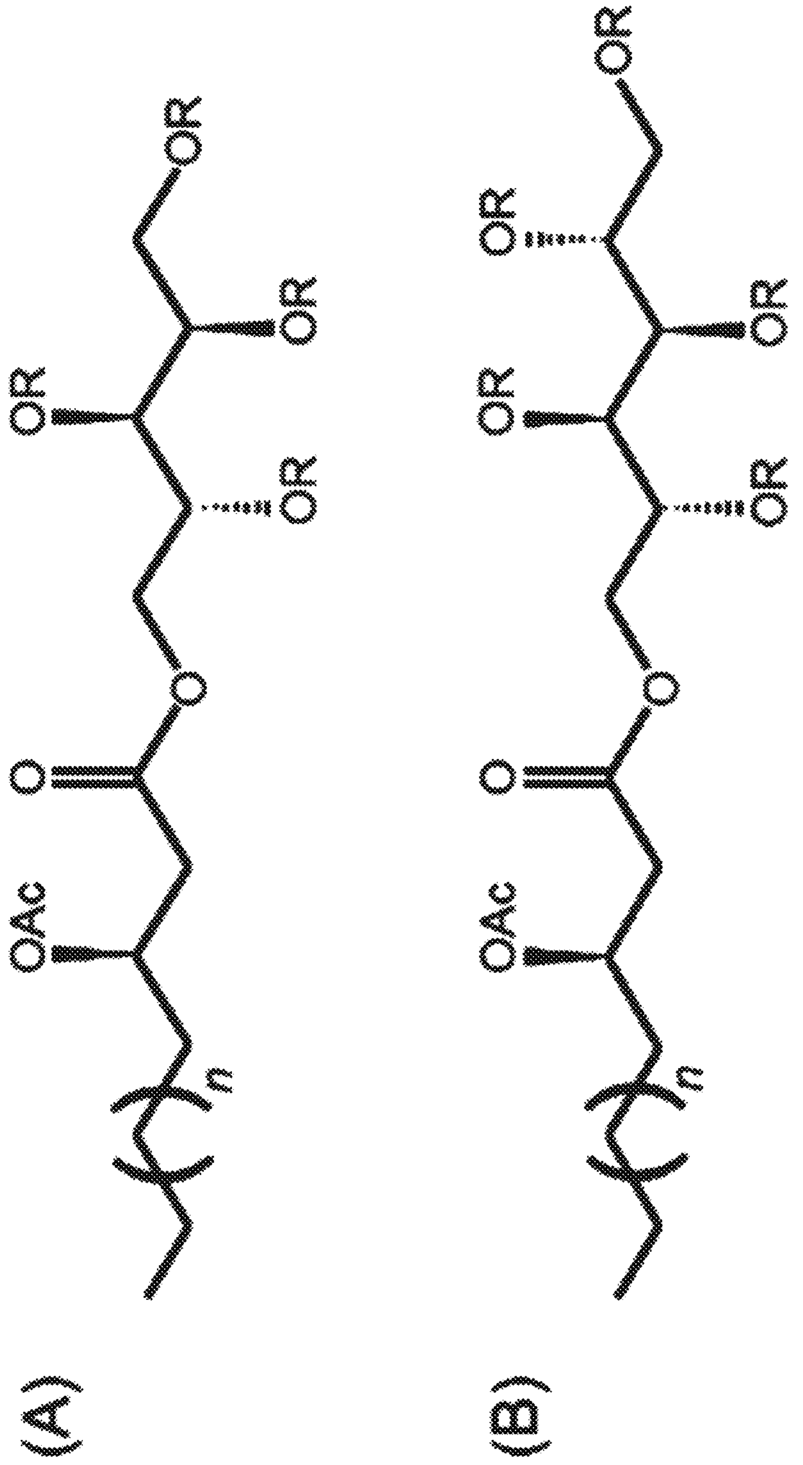
Fig. 13A-B

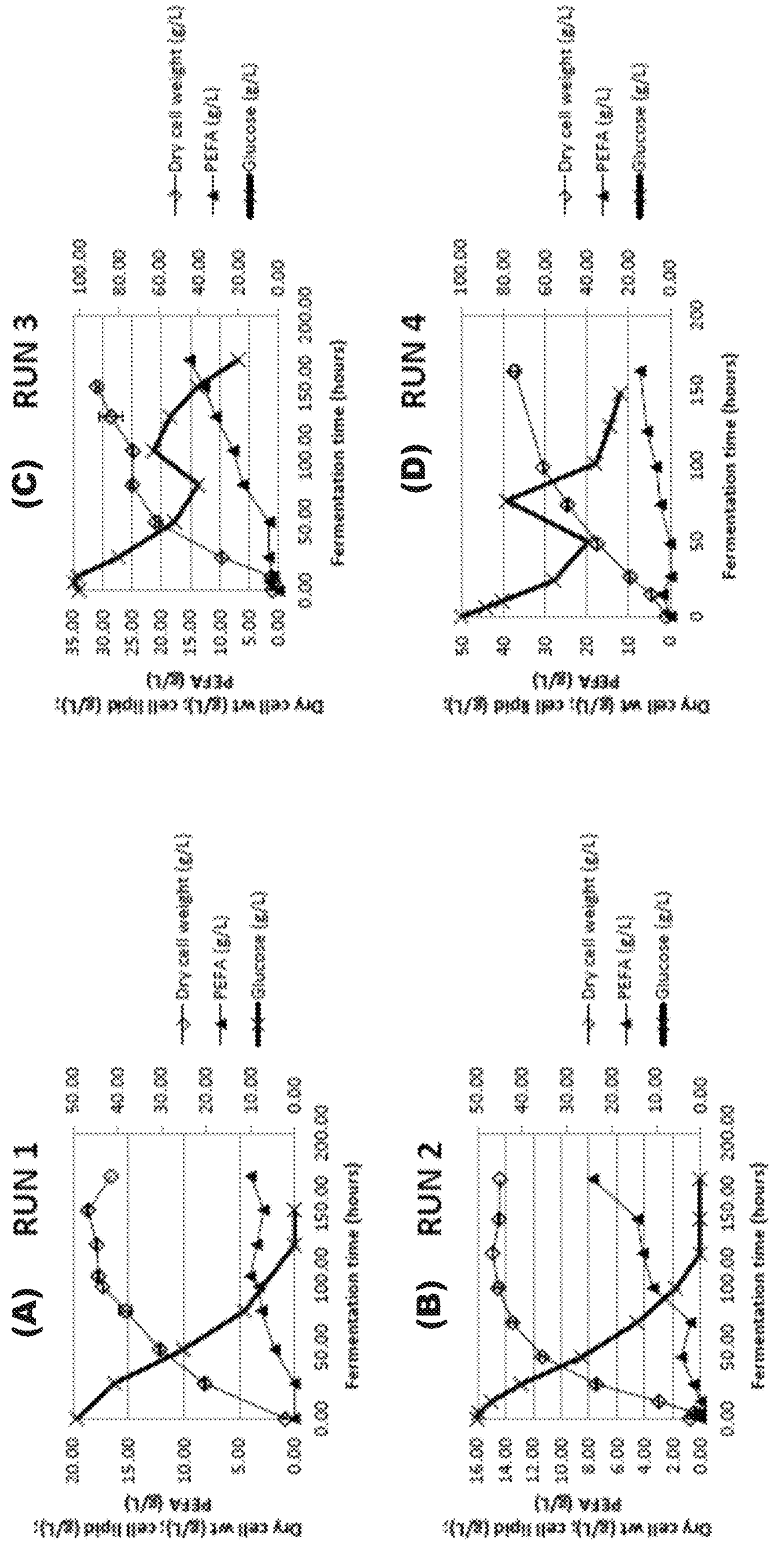
*Fig. 14A-D*

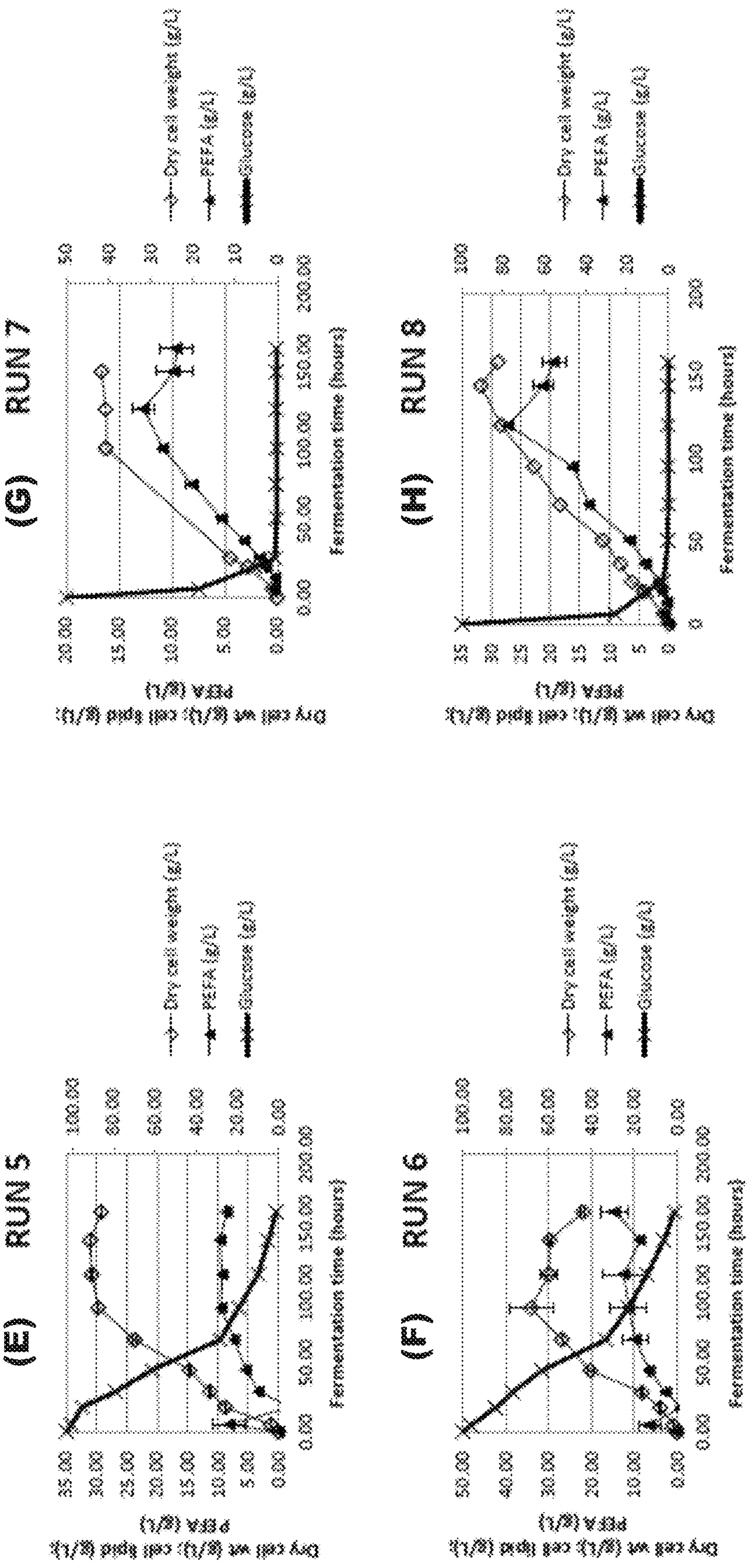
*Fig. 14E-H*

METHODS OF PRODUCING POLYOL LIPIDS

CROSS-REFERENCE TO RELATED APPLICATIONS

This application is a continuation of U.S. patent application Ser. No. 17/846,733 filed on Jun. 22, 2022, now U.S. Pat. No. 12,031,173 issued on Jul. 9, 2024, incorporated herein by reference in its entirety, which is a division of U.S. patent application Ser. No. 16/164,764 filed on Oct. 18, 2018, now U.S. Pat. No. 11,401,539 issued on Aug. 2, 2022, incorporated herein by reference in its entirety, which claims priority to, and is a 35 U.S.C. § 111 (a) continuation of, PCT international application number PCT/US2017/028670 filed on Apr. 20, 2017, incorporated herein by reference in its entirety, which claims priority to, and the benefit of, U.S. provisional patent application Ser. No. 62/325,859, filed on Apr. 21, 2016, incorporated herein by reference in its entirety. Priority is claimed to each of the foregoing applications.

The above-referenced PCT international application was published as PCT International Publication No. WO 2017/184884 A1 on Oct. 26, 2017, which publication is incorporated herein by reference in its entirety.

BACKGROUND

Surfactants, or surface active agents, are amphiphilic organic molecules used as detergents, emulsifiers, wetting agents, dispersants, foaming agents, antifoam agents, and humectants. The annual global production of surfactants was 13 million metric tons in 2008[Ashby (2013) J Surfactants Deterg 16:683-691]. Between 40 and 65% of surfactants are derived from petroleum [Deleu (2004) C R Chim 7:641-646; Rust (2008) Surfactants: a market opportunity study update. OmniTech International Ltd, Midland, MI]. The remaining feedstocks are primarily plant oils such as palm or coconut oil. Due to environmental and food security concerns, renewable and more environmentally friendly alternatives are being sought. Naturally produced microbial biosurfactants are appealing alternatives because they are produced renewably and sustainably [Makkar (2011) AMB express 1:1-19], have low ecotoxicity [Renkin (2003) Riv Ital Sostanze Gr 80:249-252], are highly biodegradable [Mulligan (2005) Environ Pollut 133:183-198; Renkin, supra], and are active under a broad range of conditions [Khan (2014) Biosurfactants: Production and Utilization—Processes, Technologies, and Economics 159:269; Marchant (2012) Trends Biotechnol 30:558-565]. Microbial biosurfactants display a unique combination of market attractiveness and high demand growth, and market prices range $10-$30 per kg, depending on the type, the market and the application [Microbial biosurfactants market: Global industry analysis, size, share, growth, trends and forecast 2014-2020. Transparency Market Research, City, pp 1-74]. Microbial biosurfactants are used in numerous applications including industrial and household cleaning products, cosmetics, lubricants, adhesives, agro-chemicals, mining, petroleum extraction and cleanup, and in pulp and paper industries.

Yeast glycolipids (GL, sec FIG. 1) are a group of microbial biosurfactants comprising sophorolipids (SL), mannosylerythritol lipid (MEL), cellobiose lipids (CL) and polyol lipids (PL) [Marchant, supra]. PL comprise two subgroups: (1) liamocins (LM), which consist of a single partially acetylated polyol head group with three or four 3,5-dihydroxydecanoic tails polyesterified through the 5-hydroxy group and are currently the best understood (FIG. 1*e*) [Price (2016) J Antibiot DOI 10.1038/ja.2016.92; Price (2013) Carbohydr Res 370:24-32], and (2) polyol esters of fatty acids (PEFA) produced by yeasts taxonomically close to the *Rhodotorula glutinis/graminis* clade [Cajka (2016) J Nat Prod 79:2580-2589; Tulloch (1964) Can J Chem 42:830-835]. PEFA are amphiphilic molecules composed of an acetylated (R)-3-hydroxy fatty acid esterified through the carboxyl end to a 5 or 6 carbon polyol, typically D-mannitol or D-arabitol, with varying degrees of acetylations (FIG. 1*d*) [Cajka, supra]. They differ from LM in that the 45 carbon is not hydroxylated and thus, only have a single acetylated (R)-3-hydroxylated acyl chain of varying numbers of carbons, usually C16:0 and C18:0. LM polyol head group is also non-acetylated, while PEFA's polyol head group can present different degrees of acetylation. Commercial production of SL, MEL and CL requires provision of both a hydrophobic carbon source such as vegetable oil, and a hydrophilic carbon source such as glucose. In contrast, PL could be synthesized in commercially relevant amounts without a hydrophobic carbon source. A few ascomycete and basidiomycete yeast species have been reported to produce PL (see Table 1). Interestingly, all the basidiomycetes reported to produce PEFA are taxonomically close to the *Rhodotorula glutinis/graminis* clade [Kurtzman (2011) The Yeasts: A Taxonomic Study. Elsevier, Oxford]. *Rhodotorula babjevae* UCDFST 04-877 secreted five times more PEFA than its phylogenetic neighbors [Cajka, supra], raising the question on whether this feature could be present in related species as well.

Recommended strategies for improving biosurfactant production include identifying new hyper-producing microorganisms, genetically modifying production strains, optimizing media and growth conditions, using wastes or other low-cost raw materials, improving downstream processing, and capturing multiple co-products [Dhanarajan (2014) Biosurfactants: Production and Utilization—Processes, Technologies, and Economics 159:153]. Addressing the first strategy to improve SL production, Kurtzman [Kurtzman (2010) FEMS Microbiol Lett 311:140-146] analyzed 26 strains from the USDA-ARS Culture Collection nrrl.ncaur.usda.gov belonging to 18 yeast species within the Starmerella clade. This clade contains Starmerella species, several related *Candida* species, and numerous species that currently lack valid species names. They confirmed that clade member *Candida apicola* produces SL, which had been previously known [Gorin (1961) Can J Chem 39:846-855; Stodola (1967) Bacteriol Rev 31:194; Tulloch (1968) Can J Chem 46:345-348]. They found three additional SL-secreting yeast species within the Starmerella clade [Kurtzman (2012) Intl J Syst Evol Microbiol 62:2307-2311; Kurtzman (2010) FEMS Microbiol Lett 311:140-146]. Targeting this taxonomic clade was therefore a successful strategy. It is important to point out that SL production was strain-specific. For example, of two strains of *Candida apicola* that were analyzed, one produced very high levels of SL, and one produced no detectable SL.

The main disadvantages of the previous art were that no detailed chemical structures of PEFA from any basidiomycetous yeast was previously described, and that the yields within the basidiomycetous yeast were low, and not suitable for commercialization. In all cases, yeast cultures were grown in media where no iron was supplemented, and the level of aeration was not as high as in cultures and methods described herein.

SUMMARY

In one aspect, a yeast culture is provided. In varying embodiments, the yeast culture comprises a population of basidiomycetous yeast cells, one or more hydrophilic (e.g., non-hydrophobic) carbon sources, and/or at least about 1 g/L polyol lipid (e.g., polyol ester of fatty acid (PEFA)), e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L polyol lipid, e.g., up to about 450 g/L of polyol lipid. In varying embodiments, the culture does not comprise one or more hydrophobic carbon sources. In varying embodiments, the culture does not comprise one or more hydrophobic carbon sources selected from the group consisting of oils, alkanes, fatty acids, fatty esters and mixtures thereof. In varying embodiments, the yeast culture comprises a population of basidiomycetous yeast cells, one or more hydrophilic (e.g., non-hydrophobic) carbon sources, one or more hydrophobic carbons sources, and at least about 1 g/L polyol lipid (e.g., polyol ester of fatty acid (PEFA)), e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L polyol lipid, e.g., up to about 450 g/L of polyol lipid. In varying embodiments, total polyol lipids are as measured after 1, 2, 3, 4, 5, 6, 7 or 8 days growth. In varying embodiments, the culture is a liquid culture. In varying embodiments, the volume of the culture is at least about 0.5 L, 1 L, 2 L, 3 L, 4 L, 5 L, 10 L, 25 L, 50 L, 75 L, 100 L, 250 L, 500 L, 1000 L, or more. In varying embodiments, the one or more hydrophilic carbon sources comprise non-hydrophobic or hydrophilic waste stream and/or hydrolysates. In varying embodiments, the culture comprises less than about 2% (w/v) nitrogen, e.g., in the range of about 0.005% (w/v) to about 2% (w/v) nitrogen. In varying embodiments, the nitrogen source is selected from the group consisting of ammonia, ammonium salt, nitrate, nitrite, nucleotides, nucleosides, proteins, peptides, amino acids, urea and its derivatives, and mixtures thereof. In varying embodiments, the culture comprises about 0.05% (w/v) ammonium chloride. In varying embodiments, the yeast culture comprises an iron salt, e.g., an iron salt selected from the group consisting of iron chloride (II) & (III), iron sulfate (II) & (III), iron nitrate (II) & (III), iron phosphate (II) & (III), fumarate, iron edetate, iron citrate, iron malate, iron oxalate, iron tartrate, iron succinate, iron acetate, in their anhydrous or their hydrated states, and organometallic complexes thereof. In some embodiments, the yeast culture comprises the iron salt in a concentration in the range of about 0.001 mg/L to about 10 g/L, e.g., from about 1 mg/L to about 0.5 g/L, e.g., from about 0.01 g/L to about 0.5 g/L. In varying embodiments, the culture comprises one or more hydrophilic carbon sources at a concentration in the range of about 0.2% (w/v) to about 70% (w/v), e.g., in the range of about 0.2% (w/v) to about 10%, 20%, 30%, 40%, 50% or 60% (w/v). In varying embodiments, the yeast culture is supplemented with extra hydrophilic carbon source (e.g., a mono- or di-saccharide, e.g., glucose and/or sucrose) to a concentration of at least about 50 g/L, e.g., at least about 75 g/L, 100 g/L, 125 g/L, 150 g/L, 175 g/L, 200 g/L, 225 g/L, 250 g/L, 275 g/L or 300 g/L. In varying embodiments, the culture comprises a carbon to nitrogen ratio of about 5:1 to about 400:1, e.g., from about 10:1 to about 200:1, from about 20:1 to about 100:1, e.g., from about 25:1 to about 75:1, e.g., from about 30:1 to about 70:1, e.g., from about 40:1 to about 60:1, e.g., from about 30:1 to about 40:1, e.g., using a nitrogen source that can be consumed or utilized by the yeast cells. In some embodiments, the culture comprises dissolved oxygen at a concentration of a least about 10%, e.g., at least about 15%, 20%, 25%, 30%, 35%, 40%, 45%, and up to 60%, 70%, 80%, 90%, 100% dissolved oxygen, e.g., from about 15% to about 80%, e.g., from about 20% to about 60% dissolved oxygen. In varying embodiments, the hydrophilic carbon source is selected from the group consisting of monosaccharides, oligosaccharides, polysaccharides, sugar alcohols, polyols, polyol lipids (including polyol esters of fatty acid (PEFAs)), organic acids, esters, aldehydes, ketones, alcohols, waste streams, plant materials, lignocellulosic hydrolysates, industrial co-products and mixtures thereof. In varying embodiments, the hydrophilic carbon source is a monosaccharide, an oligosaccharide or a polysaccharide and comprises one or more sugar moieties selected from the group consisting of glucose, sucrose, xylose, galactose, rhamnose, arabinose, mannose, cellobiose, galacturonic acid, lactose, sophorose, glycerol, and mixtures thereof. In varying embodiments, the population of basidiomycetous yeast cells comprises cells in the taxonomic class Microbotryomycetes. In varying embodiments, the population of basidiomycetous yeast cells comprises cells in the taxonomic order Sporidiobolales. In varying embodiments, the population of basidiomycetous yeast cells is from genera classified within the taxonomic order Sporidiobolales selected from the group consisting of *Rhodosporidiobolus, Rhodotorula*, and *Sporobolomyces*. In varying embodiments, the population of basidiomycetous yeast cells comprises *Rhodotorula* cells. In varying embodiments, the *Rhodotorula* cells are *Rhodotorula babjevae* (syn. *Rhodosporidium babjevae*) cells. In varying embodiments, the population of basidiomycetous yeast cells comprises one or more species selected from the group consisting of *Rhodotorula babjevae* (syn. *Rhodosporidium babjevae*), *Rhodotorula diobovata* (syn. *Rhodosporidium diobovatum*), *Rhodotorula kratochvilovae* (syn. *Rhodosporidium kratochvilovae*), *Rhodotorula paludigena* (syn. *Rhodosporidium paludigenum*), *Rhodotorula* aff. *paludigena* (syn. *Rhodosporidium* aff. *paludigenum*), and *Rhodotorula dairenensis*. In varying embodiments, the population of basidiomycetous yeast cells comprises one or more strains selected from the group consisting of:

a) *Rhodotorula babjevae* (syn. *Rhodosporidium babjevae*) strain NRRL Y-67018 (also deposited as UCDFST 04-877),
b) *Rhodotorula babjevae* (syn. *Rhodosporidium babjevae*) strain NRRL Y-67017 (also deposited as UCDFST 05-775),
c) *Rhodotorula babjevae* (syn. *Rhodosporidium babjevae*) strain UCDFST 68-916.1,
d) *Rhodotorula babjevae* (syn. *Rhodosporidium babjevae*) strain UCDFST 67-458,
f) *Rhodotorula diobovata* (syn. *Rhodosporidium diobovatum*) strain UCDFST 04-830,
g) *Rhodotorula diobovata* (syn. *Rhodosporidium diobovatum*) strain NRRL Y-67015 (also deposited as UCDFST 08-225),
h) *Rhodotorula kratochvilovae* (syn. *Rhodosporidium kratochvilovae*) strain NRRL Y-67016 (also deposited as UCDFST 05-632),
i) *Rhodotorula paludigena* (syn. *Rhodosporidium paludigenum*) strain NRRL Y-67012 (also deposited as UCDFST 09-163),
j) *Rhodotorula paludigena* (syn. *Rhodosporidium paludigenum*) strain UCDFST 81-492,
k) *Rhodotorula paludigena* (syn. *Rhodosporidium paludigenum*) strain UCDFST 82-646.2, l) *Rhodotorula* aff. *paludigena* (syn. *Rhodosporidium* aff. *paludigenum* strain NRRL Y-67009 (also deposited as UCDFST 81-84), and m) *Rhodotorula dairenensis* strain NRRL Y-67011 (also deposited as UCDFST 68-257). In varying embodiments, the population of basidiomycetous yeast cells comprises one or more strains selected from the group consisting of: a) *Rhodotorula babjevae* (syn. *Rhodosporidium babjevae*) strain UCDFST 68-916.1, b) *Rhodotorula babjevae* (syn. *Rhodosporidium babjevae*) strain UCDFST 67-458, c) *Rhodotorula babjevae* (syn. *Rhodosporidium babjevae*) strain UCDFST 05-736, d) *Rhodotorula diobovata* (syn. *Rhodosporidium diobovatum*) strain UCDFST 04-830, e) *Rhodotorula paludigena* (syn. *Rhodosporidium paludigenum*) strain UCDFST 81-492, and f) *Rhodotorula paludigena* (syn. *Rhodosporidium paludigenum*) strain UCDFST 82-646.2. In varying embodiments, the cells do not comprise *Pseudohyphozyma bogoriensis* (syn. *Rhodotorula bogoriensis*). In varying embodiments, the polyol lipids comprise polyol esters of fatty acids (PEFAs). In varying embodiments, the polyol lipid comprises an (R)-3-hydroxy fatty acid moiety comprising from 10 to 24 carbon atoms in length, e.g., from 14 to 24 carbon atoms in length. In varying embodiments, the polyol lipid comprises a sugar alcohol moiety esterified to the carboxyl end of the (R)-3-hydroxy fatty acyl moiety. In varying embodiments, the (R)-3-hydroxy fatty acyl moiety can be acetylated. In varying embodiments, the polyol lipid sugar alcohol moiety comprises non-esterified hydroxy groups that can be acetylated. In varying embodiments, the polyol lipid sugar alcohol moiety comprises a backbone selected from D-mannitol and D-arabitol. In varying embodiments, the polyol lipid sugar alcohol moiety does not comprise xylitol.

In varying embodiments of the yeast culture, the polyol lipid comprises one or more polyol esters of fatty acids (PEFAs) listed in Table 4.

In varying embodiments, the yeast culture comprises a polyol lipid (e.g. PEFA) profile comprising:

i) at least about 20%, e.g., at least about 25%, 30%, 35%, 40%, up to about 45% of an acetylated C16:0 (R)-3-hydroxy fatty acid esterified to D-arabitol comprising 4 acetylations (Molecular Formula: $C_{31}H_{52}O_{12}$);

ii) at least about 5%, e.g., at least about 6%, 7%, 8%, 9%, 10%, 15%, 20%, up to about 25%, of an acetylated C18:0 (R)-3-hydroxy fatty acid esterified to D-arabitol comprising 4 acetylations (Molecular Formula: $C_{33}H_{56}O_{12}$); and/or iii) at least about 5%, e.g., at least about 6%, 7%, 8%, 9%, 10%, 15%, up to about 20% of an acetylated C18:0 (R)-3-hydroxy fatty acid esterified to D-mannitol comprising 4 acetylations (Molecular Formula: $C_{34}H_{58}O_{13}$).

In varying embodiments, the yeast culture comprises a polyol lipid (e.g. PEFA) comprising at least about 25%, e.g., at least about 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$).

In varying embodiments, the yeast culture comprises a polyol lipid (e.g. PEFA) comprising:

i) at least about 5%, e.g., at least about 6%, 7%, 8%, 9%, 10%, 15%, up to about 18%, of an acetylated C18:0 (R)-3-hydroxy fatty acid esterified to D-mannitol comprising 3 acetylations (Molecular Formula: $C_{32}H_{56}O_{12}$);

ii) at least about 1%, e.g., at least about 2%, 3%, 4%, 5%, 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

iii) at least about 5%, e.g., at least about 6%, 7%, 8%, 9%, 10%, 15%, 20%, up to about 25%, of an acetylated C18:0 (R)-3-hydroxy fatty acid esterified to D-mannitol comprising 4 acetylations (Molecular Formula: $C_{34}H_{58}O_{13}$);

iv) at least about 15%, e.g., at least about 16%, 17%, 18%, 19%, 20%, 25%, 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$); and/or v) at least about 10%, e.g., at least about 11%, 12%, 13%, 14%, 15%, 16%, 17%, 18%, 19%, 20%, 25%, 30%, up to about 35% of an acetylated C18:0 (R)-3-hydroxy fatty acid esterified to D-arabitol comprising 4 acetylations (Molecular Formula: $C_{33}H_{56}O_{12}$).

In varying embodiments, the yeast culture further comprises a polyol lipid (e.g. PEFA) comprising:

vi) at least about 2%, e.g., at least about 3%, 4%, 5%, 6%, 7%, 8%, 9%, 10%, up to about 12%, of an acetylated C16:0 (R)-3-hydroxy fatty acid esterified to D-mannitol comprising 5 acetylations (Molecular Formula: $C_{34}H_{56}O_{14}$); and/or vii) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol (Molecular Formula: $C_{36}H_{60}O_{14}$).

In varying embodiments, the yeast culture comprises a polyol lipid (e.g. PEFA) comprising:

i) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, 30%, 35%, 40%, up to about 45%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$); and/or v) at least about 15%, e.g., at least about 20%, 25%, 30%, 35%, 40%, up to about 45% of an acetylated C18:0 (R)-3-hydroxy fatty acid esterified to D-arabitol comprising 4 acetylations (Molecular Formula: $C_{33}H_{56}O_{12}$).

In varying embodiments, the yeast culture comprises a polyol lipid (e.g. PEFA) comprising:

i) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, up to about 30%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 5%, e.g., at least about 6%, 7%, 8%, 9%, 10%, up to about 12%, of an acetylated C16:0 (R)-3-hydroxy fatty acid esterified to D-arabitol comprising 4 acetylations (Molecular Formula: $C_{31}H_{52}O_{12}$);

v) at least about 15%, e.g., at least about 20%, 25%, 30%, 35%, 40%, up to about 45%, of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4%, 5% up to about 6% of an acetylated C14:0 (R)-3-hydroxy fatty acid esterified to D-arabitol comprising 4 acetylations (Molecular Formula: $C_{29}H_{48}O_{12}$).

In varying embodiments, the yeast culture comprises a polyol lipid (e.g. PEFA) comprising:

i) at least about 5%, e.g., at least about 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 10%, e.g., at least about 11%, 12%, 13%, 14%, 15%, 16%, 17%, 18%, 19%, 20%, up to about 25%, of an acetylated C16:0 (R)-3-hydroxy fatty acid esterified to D-mannitol comprising 5 acetylations (Molecular Formula: $C_{34}H_{56}O_{14}$);

iii) at least about 5%, e.g., at least about 6%, 7%, 8%, 9%, 10%, up to about 12%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$);

v) at least about 35%, e.g., at least about 36%, 37%, 38%, 39%, 40%, up to about 45% of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4% up to about 5%, of an acetylated C16:0 (R)-3-hydroxy fatty acid esterified to D-mannitol comprising 3 acetylations (Molecular Formula: $C_{30}H_{52}O_{12}$).

In varying embodiments, the yeast culture comprises a polyol lipid (e.g. PEFA) comprising:

i) at least about 5%, e.g., at least about 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

ii) at least about 45%, e.g., at least about 46%, 47%, 48%, 49%, up to about 50% of an acetylated C16:0 (R)-3-hydroxy fatty acid esterified to D-arabitol comprising 4 acetylations (Molecular Formula: $C_{31}H_{52}O_{12}$); and/or iii) at least about 5%, e.g., at least about 6%, 7%, 8%, 9%, 10%, up to about 12% of an acetylated C18:0 (R)-3-hydroxy fatty acid esterified to D-arabitol comprising 4 acetylations (Molecular Formula: $C_{33}H_{56}O_{12}$).

In varying embodiments, the one or more hydrophobic carbon sources are selected from the group consisting of oils, alkanes, fatty acids, fatty esters and mixtures thereof. In varying embodiments, the one or more polyol lipids are present in the medium in a form that can be harvested without solvent extraction.

Further provided is a bioreactor comprising a yeast culture, as described above and herein.

In a further aspect, provided are methods of producing one or more polyol lipids. In some embodiments, the methods comprise culturing a population of basidiomycetous yeast cells in a yeast cell culture comprising one or more hydrophilic (e.g., non-hydrophobic) carbon sources, whereby the basidiomycetous yeast cells produce one or more polyol esters of fatty acids (PEFAs). In varying embodiments, the culture does not comprise one or more hydrophobic carbon sources. In some embodiments, the methods comprise culturing a population of basidiomycetous yeast cells in a yeast cell culture comprising one or more hydrophilic (e.g., non-hydrophobic) carbon sources and one or more hydrophobic carbon sources, whereby the basidiomycetous yeast cells produce one or more polyol lipids (e.g., polyol esters of fatty acids (PEFAs)). In varying embodiments, additional hydrophilic carbon source is added, e.g., during any stage of growth including exponential growth, and after the population of basidiomycetous yeast cells reaches stationary phase. In varying embodiments, at least about 1 g/L polyol lipid (e.g., polyol esters of fatty acids (PEFAs)), e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L polyol lipid, e.g., up to about 450 g/L of polyol lipid, is produced. In some embodiments, a polyol lipid yield in the range of about 0.5 g/L to about 30 g/L can be obtained from yeast cultures comprising in the range of about 10 g/L to about 250 g/L glucose. In some embodiments, a polyol lipid yield of at least about 14 g/L, e.g., from about 14 g/L to about 17 g/L, can be obtained from yeast cultures comprising about 50 g/L glucose. In varying embodiments, total polyol lipids are as measured after 1, 2, 3, 4, 5, 6, 7 or 8 days growth. In varying embodiments, the volume of the culture is at least about 0.5 L, 1 L, 2 L, 3 L, 4 L, 5 L, 10 L, 25 L, 50 L, 75 L, 100 L, 250 L, 500 L, 1000 L, or more. In varying embodiments, the culture comprises less than about 2% (w/v) nitrogen, e.g., in the range of about 0.005% (w/v) to about 2% (w/v) nitrogen. In varying embodiments, the nitrogen source is selected from the group consisting of ammonia, ammonium salt, nitrate, nitrite, nucleotides, nucleosides, proteins, peptides, amino acids, urea and its derivatives, and mixtures thereof. In varying embodiments, the culture comprises about 0.05% (w/v) ammonium chloride. In varying embodiments, the yeast culture comprises an iron salt, e.g., an iron salt selected from the group consisting of iron chloride (II) & (III), iron sulfate (II) & (III), iron nitrate (II) & (III), iron phosphate (II) & (III), fumarate, iron edetate, iron citrate, iron malate, iron oxalate, iron tartrate, iron succinate, iron acetate, in their anhydrous or their hydrated states, and organometallic complexes thereof. In some embodiments, the yeast culture comprises the iron salt in a concentration in the range of about 0.001 mg/L to about 10 g/L, e.g., from about 1 mg/L to about 0.5 g/L, e.g., from about 0.01 g/L to about 0.5 g/L. In varying embodiments, the culture comprises one or more hydrophilic carbon sources at a concentration in the range of about 0.2% (w/v) to about 70% (w/v), e.g., in the range of about 0.2% (w/v) to about 10%, 20%, 30%, 40%, 50% or 60% (w/v). In varying embodiments, the culture comprises a carbon to nitrogen ratio of about 5:1 to about 400:1, e.g., from about 10:1 to about 200:1, from about 20:1 to about 100:1, e.g., from about 25:1 to about 75:1, e.g., from about 30:1 to about 70:1, e.g., from about 40:1 to about 60:1, e.g., from about 30:1 to about 40:1, e.g., using a nitrogen source that can be consumed or utilized by the yeast cells. In some embodiments, the yeast culture is maintained at a temperature in the range of between about 24 °C to about 27 °C. In varying embodiments, the hydrophilic carbon source is selected from the group consisting of monosaccharides, oligosaccharides, polysaccharides, sugar alcohols, polyols, polyol lipids (e.g., polyol esters of fatty acids (PEFAs)), organic acids, esters, aldehydes, ketones, alcohols, waste streams, plant materials, lignocellulosic hydrolysates, industrial co-products and mixtures thereof. In varying embodiments, the hydrophilic carbon source is a monosaccharide, an oligosaccharide or a polysaccharide and comprises one or more sugar moieties selected from the group consisting of glucose, sucrose, xylose, galactose, rhamnose, arabinose, mannose, cellobiose, galacturonic acid, lactose, sophorose, glycerol, and mixtures thereof. In varying embodiments, the population of basidiomycetous yeast cells comprises cells in the taxonomic class Microbotryomycetes. In varying embodiments, the population of basidiomycetous yeast cells comprises cells in the taxonomic order Sporidiobolales. In varying embodiments, the population of basidiomycetous yeast cells is from genera classified within the taxonomic order Sporidiobolales selected from the group consisting of *Rhodosporidiobolus, Rhodotorula*, and *Sporobolomyces*. In varying embodiments, the population of basidiomycetous yeast cells comprises *Rhodotorula* cells. In varying embodiments, the *Rhodotorula* cells are *Rhodotorula babjevae* (syn. *Rhodosporidium babjevae*) cells. In varying embodiments, the population of basidiomycetous yeast cells comprises one or more species selected from the group consisting of *Rhodotorula babjevae* (syn. *Rhodosporidium babjevae*), *Rhodotorula diobovata* (syn. *Rhodosporidium diobovatum*), *Rhodotorula kratochvilovae* (syn. *Rhodosporidium kratochvilovae*), *Rhodotorula paludigena* (syn. *Rhodosporidium paludigenum*), *Rhodotorula* aff. *paludigena* (syn. *Rhodosporidium* aff. *paludigenum*), and *Rhodotorula dairenensis*. In varying embodiments, the population of basidiomycetous yeast cells comprises one or more strains selected from the group consisting of:

a) *Rhodotorula babjevae* (syn. *Rhodosporidium babjevae*) strain NRRL Y-67018 (also deposited as UCDFST 04-877), b) *Rhodotorula babjevae* (syn. *Rhodosporidium babjevae*) strain NRRL Y-67017 (also deposited as UCDFST 05-775), c) *Rhodotorula babjevae* (syn. *Rhodosporidium babjevae*) strain UCDFST 68-916.1, d) *Rhodotorula babjevae* (syn. *Rhodosporidium babjevae*) strain UCDFST 67-458, f) *Rhodotorula diobovata* (syn. *Rhodosporidium diobovatum*) strain UCDFST 04-830, g) *Rhodotorula diobovata* (syn. *Rhodosporidium diobovatum*) strain NRRL Y-67015 (also deposited as UCDFST 08-225), h) *Rhodotorula kratochvilovae* (syn. *Rhodosporidium kratochvilovae*) strain NRRL Y-67016 (also deposited as UCDFST 05-632), i) *Rhodotorula paludigena* (syn. *Rhodosporidium paludigenum*) strain NRRL Y-67012 (also deposited as UCDFST 09-163), j) *Rhodotorula paludigena* (syn. *Rhodosporidium paludigenum*) strain UCDFST 81-492, k) *Rhodotorula paludigena* (syn. *Rhodosporidium paludigenum*) strain UCDFST 82-646.2, l) *Rhodotorula* aff. *paludigena* (syn. *Rhodosporidium* aff. *paludigenum* strain NRRL Y-67009 (also deposited as UCDFST 81-84), and m) *Rhodotorula dairenensis* strain NRRL Y-67011 (also deposited as UCDFST 68-257). In varying embodiments, the population of basidiomycetous yeast cells comprises one or more strains selected from the group consisting of: a) *Rhodotorula babjevae* (syn. *Rhodosporidium babjevae*) strain UCDFST 68-916.1, b) *Rhodotorula babjevae* (syn. *Rhodosporidium babjevae*) strain UCDFST 67-458, c) *Rhodotorula babjevae* (syn. *Rhodosporidium babjevae*) strain UCDFST 05-736, d) *Rhodotorula diobovata* (syn. *Rhodosporidium diobovatum*) strain UCDFST 04-830, e) *Rhodotorula paludigena* (syn. *Rhodosporidium paludigenum*) strain UCDFST 81-492, and f) *Rhodotorula paludigena* (syn. *Rhodosporidium paludigenum*) strain UCDFST 82-646.2. In varying embodiments, the cells do not comprise *Pseudohyphozyma bogoriensis* (syn. *Rhodotorula bogoriensis*). In varying embodiments, the polyol lipid comprises one or more polyol esters of fatty acids (PEFAs). In varying embodiments, the polyol lipid comprises a 3-hydroxy fatty acid comprising from 10 to 24 carbon atoms in length, e.g., from 14 to 24 carbon atoms in length. In varying embodiments, the polyol lipid comprises a sugar alcohol moiety esterified to the carboxyl end of the 3-hydroxy fatty acyl moiety. In varying embodiments, the 3 hydroxyl fatty acyl moiety can be acetylated. In varying embodiments, the polyol lipid sugar alcohol moiety comprises non-esterified hydroxy groups that can be acetylated. In varying embodiments, the polyol lipid sugar alcohol moiety comprises a backbone selected from D-mannitol and D-arabitol. In varying embodiments, the polyol lipid sugar alcohol moiety does not comprise xylitol. In varying embodiments of the yeast culture, the polyol lipid comprises one or more polyol esters of fatty acids (PEFAs) listed in Table 4.

In varying embodiments, the methods produce a yeast culture comprising a polyol lipid (e.g. PEFA) comprising:

i) at least about 20%, e.g., at least about 25%, 30%, 35%, 40%, up to about 45% of an acetylated C16:0 (R)-3-hydroxy fatty acid esterified to D-arabitol comprising 4 acetylations (Molecular Formula: $C_{31}H_{52}O_{12}$);

ii) at least about 5%, e.g., at least about 6%, 7%, 8%, 9%, 10%, 15%, 20%, up to about 25%, of an acetylated C18:0 (R)-3-hydroxy fatty acid esterified to D-arabitol comprising 4 acetylations (Molecular Formula: $C_{33}H_{56}O_{12}$); and/or iii) at least about 5%, e.g., at least about 6%, 7%, 8%, 9%, 10%, 15%, up to about 20% of an acetylated C18:0 (R)-3-hydroxy fatty acid esterified to D-mannitol comprising 4 acetylations (Molecular Formula: $C_{34}H_{58}O_{13}$).

In varying embodiments, the methods produce a yeast culture comprising a polyol lipid (e.g. PEFA) comprising at least about 25%, e.g., at least about 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$).

In varying embodiments, the methods produce a yeast culture comprising a polyol lipid (e.g. PEFA) comprising:

i) at least about 5%, e.g., at least about 6%, 7%, 8%, 9%, 10%, 15%, up to about 18%, of an acetylated C18:0 (R)-3-hydroxy fatty acid esterified to D-mannitol comprising 3 acetylations (Molecular Formula: $C_{32}H_{56}O_{12}$);

ii) at least about 1%, e.g., at least about 2%, 3%, 4%, 5%, 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

iii) at least about 5%, e.g., at least about 6%, 7%, 8%, 9%, 10%, 15%, 20%, up to about 25%, of an acetylated C18:0 (R)-3-hydroxy fatty acid esterified to D-mannitol comprising 4 acetylations (Molecular Formula: $C_{34}H_{58}O_{13}$);

iv) at least about 15%, e.g., at least about 16%, 17%, 18%, 19%, 20%, 25%, 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$); and/or v) at least about 10%, e.g., at least about 11%, 12%, 13%, 14%, 15%, 16%, 17%, 18%, 19%, 20%, 25%, 30%, up to about 35% of an acetylated C18:0 (R)-3-hydroxy fatty acid esterified to D-arabitol comprising 4 acetylations (Molecular Formula: $C_{33}H_{56}O_{12}$).

In varying embodiments, the methods produce a yeast culture comprising a polyol lipid (e.g. PEFA) comprising:

vi) at least about 2%, e.g., at least about 3%, 4%, 5%, 6%, 7%, 8%, 9%, 10%, up to about 12%, of an acetylated C16:0 (R)-3-hydroxy fatty acid esterified to D-mannitol comprising 5 acetylations (Molecular Formula: $C_{34}H_{56}O_{14}$); and/or vii) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol (Molecular Formula: $C_{36}H_{60}O_{14}$).

In varying embodiments, the methods produce a yeast culture comprising a polyol lipid (e.g. PEFA) comprising:

i) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, 30%, 35%, 40%, up to about 45%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$); and/or v) at least about 15%, e.g., at least about 20%, 25%, 30%, 35%, 40%, up to about 45% of an acetylated C18:0 (R)-3-hydroxy fatty acid esterified to D-arabitol comprising 4 acetylations (Molecular Formula: $C_{33}H_{56}O_{12}$).

In varying embodiments, the methods produce a yeast culture comprising a polyol lipid (e.g. PEFA) comprising:

i) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, up to about 30%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 5%, e.g., at least about 6%, 7%, 8%, 9%, 10%, up to about 12%, of an acetylated C16:0 (R)-3-hydroxy fatty acid esterified to D-arabitol comprising 4 acetylations (Molecular Formula: $C_{31}H_{52}O_{12}$);

v) at least about 15%, e.g., at least about 20%, 25%, 30%, 35%, 40%, up to about 45%, of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4%, 5% up to about 6% of an acetylated C14:0 (R)-3-hydroxy fatty acid esterified to D-arabitol comprising 4 acetylations (Molecular Formula: $C_{29}H_{48}O_{12}$).

In varying embodiments, the methods produce a yeast culture comprising a polyol lipid (e.g. PEFA) comprising:

i) at least about 5%, e.g., at least about 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 10%, e.g., at least about 11%, 12%, 13%, 14%, 15%, 16%, 17%, 18%, 19%, 20%, up to about 25%, of an acetylated C16:0 (R)-3-hydroxy fatty acid esterified to D-mannitol comprising 5 acetylations (Molecular Formula: $C_{34}H_{56}O_{14}$);

iii) at least about 5%, e.g., at least about 6%, 7%, 8%, 9%, 10%, up to about 12%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$);

v) at least about 35%, e.g., at least about 36%, 37%, 38%, 39%, 40%, up to about 45% of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4% up to about 5%, of an acetylated C16:0 (R)-3-hydroxy fatty acid esterified to D-mannitol comprising 3 acetylations (Molecular Formula: $C_{30}H_{52}O_{12}$).

In varying embodiments, the methods produce a yeast culture comprising a polyol lipid (e.g. PEFA) comprising:

i) at least about 5%, e.g., at least about 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

ii) at least about 45%, e.g., at least about 46%, 47%, 48%, 49%, up to about 50% of an acetylated C16:0 (R)-3-hydroxy fatty acid esterified to D-arabitol comprising 4 acetylations (Molecular Formula: $C_{31}H_{52}O_{12}$); and/or iii) at least about 5%, e.g., at least about 6%, 7%, 8%, 9%, 10%, up to about 12% of an acetylated C18:0 (R)-3-hydroxy fatty acid esterified to D-arabitol comprising 4 acetylations (Molecular Formula: $C_{33}H_{56}O_{12}$).

In varying embodiments of the methods of producing, the one or more hydrophobic carbon sources are selected from the group consisting of oils, alkanes, fatty acids, fatty esters and mixtures thereof. In varying embodiments, the method does not comprise actively pH-adjusting the culture. In some embodiments, the culture volume to container volume ratio is 1:3 or greater, e.g., 1:4, 1:5, 1:6, 1:7, 1:8, 1:9, 1:10 or greater. In some embodiments, the container is a baffled flask, e.g., covered in such a manner to allow air/oxygen exchange, e.g., with a foam stopper. In some embodiments, the culture comprises dissolved oxygen at a concentration of a least about 10%, e.g., at least about 15%, 20%, 25%, 30%, 35%, 40%, 45%, and up to 60%, 70%, 80%, 90%, 100% dissolved oxygen, e.g., from about 15% to about 80%, e.g., from about 20% to about 60% dissolved oxygen. In varying embodiments, the methods further comprise purifying and/or isolating the polyol lipid. In varying embodiments, the polyol lipid does not need to be purified from a hydrophobic carbon source. In varying embodiments, the polyol lipid can be purified and/or isolated without cell lysis, e.g., directly from the media. In some embodiments, the yeast cells secrete the one or more polyol lipids into the medium in a form that can be harvested without solvent extraction.

In a related aspect, provided are polyol lipid compositions produced according to the methods described above and herein. In another aspect, provided are compositions comprising one or more polyol esters of fatty acids (PEFAs) listed in Table 4. In varying embodiments, the polyol lipid compositions are selected from the group consisting of a cleanser, a detergent, a surfactant (e.g., for recovery of oil), a wetting agent, an antifoam agent, an emulsifier, an emollient, a dispersant (e.g., for cleanup of oil including spilled petroleum), a humectant, an antibacterial agent, an antiviral agent, an antifungal agent, a spermicide, an insecticide, a lubricant, an adhesive, a crystal modifier, an instantizer, a viscosity modifier, a mixing/blending aid, a release agent, a cream, a foam, a mousse, a lotion, a balm, and an ointment. In varying embodiments, polyol lipid composition is free of any hydrophobic carbon source. In varying embodiments, the method is performed as a batch, fed batch or continuous-feed process.

In varying embodiments, the composition comprises a polyol lipid (e.g. PEFA) comprising:

i) at least about 20%, e.g., at least about 25%, 30%, 35%, 40%, up to about 45% of an acetylated C16:0 (R)-3-hydroxy fatty acid esterified to D-arabitol comprising 4acetylations (Molecular Formula: $C_{31}H_{52}O_{12}$);

ii) at least about 5%, e.g., at least about 6%, 7%, 8%, 9%, 10%, 15%, 20%, up to about 25%, of an acetylated C18:0 (R)-3-hydroxy fatty acid esterified to D-arabitol comprising 4 acetylations (Molecular Formula: $C_{33}H_{56}O_{12}$); and/or iii) at least about 5%, e.g., at least about 6%, 7%, 8%, 9%, 10%, 15%, up to about 20% of an acetylated C18:0 (R)-3-hydroxy fatty acid esterified to D-mannitol comprising 4 acetylations (Molecular Formula: $C_{34}H_{58}O_{13}$).

In varying embodiments, the composition comprises a polyol lipid (e.g. PEFA) comprising at least about 25%, e.g., at least about 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$).

In varying embodiments, the composition comprises a polyol lipid (e.g. PEFA) comprising:

i) at least about 5%, e.g., at least about 6%, 7%, 8%, 9%, 10%, 15%, up to about 18%, of an acetylated C18:0 (R)-3-hydroxy fatty acid esterified to D-mannitol comprising 3 acetylations (Molecular Formula: $C_{32}H_{56}O_{12}$);

ii) at least about 1%, e.g., at least about 2%, 3%, 4%, 5%, 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

iii) at least about 5%, e.g., at least about 6%, 7%, 8%, 9%, 10%, 15%, 20%, up to about 25%, of an acetylated C18:0 (R)-3-hydroxy fatty acid esterified to D-mannitol comprising 4 acetylations (Molecular Formula: $C_{34}H_{58}O_{13}$);

iv) at least about 15%, e.g., at least about 16%, 17%, 18%, 19%, 20%, 25%, 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$); and/or v) at least about 10%, e.g., at least about 11%, 12%, 13%, 14%, 15%, 16%, 17%, 18%, 19%, 20%, 25%, 30%, up to about 35% of an acetylated C18:0 (R)-3-hydroxy fatty acid esterified to D-arabitol comprising 4 acetylations (Molecular Formula: $C_{33}H_{56}O_{12}$).

In varying embodiments, the compositions further comprise a polyol lipid (e.g. PEFA) comprising:

vi) at least about 2%, e.g., at least about 3%, 4%, 5%, 6%, 7%, 8%, 9%, 10%, up to about 12%, of an acetylated C16:0 (R)-3-hydroxy fatty acid esterified to D-mannitol comprising 5 acetylations (Molecular Formula: $C_{34}H_{56}O_{14}$); and/or vii) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol (Molecular Formula: $C_{36}H_{60}O_{14}$).

In varying embodiments, the composition comprises a polyol lipid (e.g. PEFA) comprising:

i) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, 30%, 35%, 40%, up to about 45%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$); and/or v) at least about 15%, e.g., at least about 20%, 25%, 30%, 35%, 40%, up to about 45% of an acetylated C18:0

(R)-3-hydroxy fatty acid esterified to D-arabitol comprising 4 acetylations (Molecular Formula: $C_{33}H_{56}O_{12}$).

In varying embodiments, the composition comprises a polyol lipid (e.g. PEFA) comprising:

i) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, up to about 30%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 5%, e.g., at least about 6%, 7%, 8%, 9%, 10%, up to about 12%, of an acetylated C16:0 (R)-3-hydroxy fatty acid esterified to D-arabitol comprising 4 acetylations (Molecular Formula: $C_{31}H_{52}O_{12}$);

v) at least about 15%, e.g., at least about 20%, 25%, 30%, 35%, 40%, up to about 45%, of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4%, 5% up to about 6% of an acetylated C14:0 (R)-3-hydroxy fatty acid esterified to D-arabitol comprising 4 acetylations (Molecular Formula: $C_{29}H_{48}O_{12}$).

In varying embodiments, the composition comprises a polyol lipid (e.g. PEFA) comprising:

i) at least about 5%, e.g., at least about 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 10%, e.g., at least about 11%, 12%, 13%, 14%, 15%, 16%, 17%, 18%, 19%, 20%, up to about 25%, of an acetylated C16:0 (R)-3-hydroxy fatty acid esterified to D-mannitol comprising 5 acetylations (Molecular Formula: $C_{34}H_{56}O_{14}$);

iii) at least about 5%, e.g., at least about 6%, 7%, 8%, 9%, 10%, up to about 12%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$);

v) at least about 35%, e.g., at least about 36%, 37%, 38%, 39%, 40%, up to about 45% of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4% up to about 5%, of an acetylated C16:0 (R)-3-hydroxy fatty acid esterified to D-mannitol comprising 3 acetylations (Molecular Formula: $C_{30}H_{52}O_{12}$).

In varying embodiments, the composition comprises a polyol lipid (e.g. PEFA) comprising:

i) at least about 5%, e.g., at least about 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

ii) at least about 45%, e.g., at least about 46%, 47%, 48%, 49%, up to about 50% of an acetylated C16:0 (R)-3-hydroxy fatty acid esterified to D-arabitol comprising 4 acetylations (Molecular Formula: $C_{31}H_{52}O_{12}$); and/or iii) at least about 5%, e.g., at least about 6%, 7%, 8%, 9%, 10%, up to about 12% of an acetylated C18:0 (R)-3-hydroxy fatty acid esterified to D-arabitol comprising 4 acetylations (Molecular Formula: $C_{33}H_{56}O_{12}$).

In a further aspect, provided is a yeast cell of a yeast strain selected from the group consisting of:

a) *Rhodotorula babjevae* (syn. *Rhodosporidium babjevae*) strain NRRL Y-67018 (also deposited as UCDFST 04-877), b) *Rhodotorula babjevae* (syn. *Rhodosporidium babjevae*) strain NRRL Y-67017 (also deposited as UCDFST 05-775), c) *Rhodotorula babjevae* (syn. *Rhodosporidium babjevae*) strain UCDFST 68-916.1, d) *Rhodotorula babjevae* (syn. *Rhodosporidium babjevae*) strain UCDFST 67-458, f) *Rhodotorula diobovata* (syn. *Rhodosporidium diobovatum*) strain UCDFST 04-830, g) *Rhodotorula diobovata* (syn. *Rhodosporidium diobovatum*) strain NRRL Y-67015 (also deposited as UCDFST 08-225), h) *Rhodotorula kratochvilovae* (syn. *Rhodosporidium kratochvilovae*) strain NRRL Y-67016 (also deposited as UCDFST 05-632), i) *Rhodotorula paludigena* (syn. *Rhodosporidium paludigenum*) strain NRRL Y-67012 (also deposited as UCDFST 09-163), j) *Rhodotorula paludigena* (syn. *Rhodosporidium paludigenum*) strain UCDFST 81-492, k) *Rhodotorula paludigena* (syn. *Rhodosporidium paludigenum*) strain UCDFST 82-646.2, l) *Rhodotorula* aff. *paludigena* (syn. *Rhodosporidium* aff. *paludigenum* strain NRRL Y-67009 (also deposited as UCDFST 81-84), and m) *Rhodotorula dairenensis* strain NRRL Y-67011 (also deposited as UCDFST 68-257). In another aspect, provided is a yeast cell of a yeast strain selected from the group consisting of: a) *Rhodotorula babjevae* (syn. *Rhodosporidium babjevae*) strain UCDFST 68-916.1; b) *Rhodotorula babjevae* (syn. *Rhodosporidium babjevae*) strain UCDFST 67-458; c) *Rhodotorula babjevae* (syn. *Rhodosporidium babjevae*) strain UCDFST 05-736; d) *Rhodotorula diobovata* (syn. *Rhodosporidium diobovatum*) strain UCDFST 04-830; e) *Rhodotorula paludigena* (syn. *Rhodosporidium paludigenum*) strain UCDFST 81-492; and f) *Rhodotorula paludigena* (syn. *Rhodosporidium paludigenum*) strain UCDFST 82-646.2.

Further provided is a population of yeast cells comprising one or more yeast strains as described above and herein. Further provided is a yeast culture comprising one or more yeast strains as described above and herein.

DEFINITIONS

The term "population of yeast cells" refers to two or more yeast cells.

The term "hydrophobic carbon source" refers to an organic compound that is insoluble in water or has a solubility in water of less than 1 g/L.

The term "hydrophilic carbon source refers to an organic compound that is soluble in water at concentrations greater than 1 g/L.

BRIEF DESCRIPTION OF THE DRAWINGS

FIGS. 6A-B illustrates a separation of PEFA extracts after acidic hydrolysis using HILIC-ESI(−)MS with extracted ion chromatograms of (A) 3-hydroxy fatty acids and (B) C5- and C6-sugar alcohols. Both classes of compounds were detected as deprotonated molecules $[M-H]^-$.

FIGS. 7A-D illustrate a GC-MS chromatogram of 3-hydroxy fatty acids detected in PEFA extracts after acidic hydrolysis. (A) Derivatized 3-hydroxy fatty acids detected as methyl esters (m/z 103). (B) EI spectrum of methyl palmitate with highlighted specific fragment m/z 103. (C) Derivatized 3-hydroxy fatty acids detected as 3-trimethylsiloxy methyl esters (m/z 175). (D) 3-[(Trimethylsiloxy)] methyl palmitate with highlighted specific fragment m/z 175.

FIG. 8A-D illustrate GC-MS chromatograms (m/z 217) of polyols detected in PEFA extracts after acidic hydrolysis and a series of standards: (A) xylitol, arabitol (mixture of D-/L-forms), ribitol standards; (B) detected arabitol in PEFA hydrolysate; (C) mannitol (mixture of D-/L-forms), dulcitol, glucitol standards; (D) detected mannitol in PEFA hydrolysate.

FIGS. 9A-B illustrate enantioselective analysis of polyols using GC-EIMS. Extracted ion chromatograms (m/z 69) of (A) a standard mixture of D-/L-arabitol and D-/L-mannitol and (B) detected D-arabitol and D-mannitol in hydrolyzed PEFA. Compounds were detected as TFA derivatives.

FIGS. 10A-C illustrate enantioselective analysis of 3-hydroxy fatty acids using GC-EIMS. Extracted ion chromatograms (m/z 189) of (A) 3-hydroxy C14:0, (B) 3-hydroxy C16:0, and (C) 3-hydroxy C18:0. Compounds were detected as MTPA-O-fatty acid methyl esters.

FIGS. 11A-B illustrate predicted fragment structures of polyol esters of fatty acids based on MS/MS spectra acquired in ESI(+): (A) acetylated 3-hydroxypalmitic acid condensed with completely acetylated arabitol ($C_{31}H_{52}O_{12}$; peak 5 in FIG. 5); (B) acetylated 3-hydroxystearic acid condensed with completely acetylated arabitol ($C_{33}H_{56}O_{12}$; peak 10 in FIG. 5).

FIG. 12A-B illustrates predicted fragment structures of polyol esters of fatty acids based on MS/MS spectra acquired in ESI (+): (A) acetylated 3-hydroxypalmitic acid condensed with partially acetylated mannitol ($C_{32}H_{54}O_{13}$; peak 4 in FIG. 5); (B) acetylated 3-hydroxystearic acid condensed with partially acetylated mannitol ($C_{34}H_{58}O_{13}$; peak 9 in FIG. 5).

FIGS. 13A-B illustrate a general structure of polyol esters of fatty acids with (A) arabitol and (B) mannitol as a hydrophilic moiety secreted by *Rhodotorula babjevae* UCDFST 04-877. The value for n can vary from 8 to 12. R can be either hydrogen-H or an acetyl group —$COCH_3$.

FIGS. 14A-I illustrate the data obtained during Runs 1-9 of benchtop bioreactor cultivation of yeast strains *Rhodotorula babjevae* UCDFST 04-877, *Rhodotorula* aff. *paludigena* UCDFST 81-84, using either glucose or sucrose as main carbon sources, dosed in different amounts and fashions. The end point results and sugar dosing are given in Table 5.

DETAILED DESCRIPTION

1. Introduction

Figure 1:
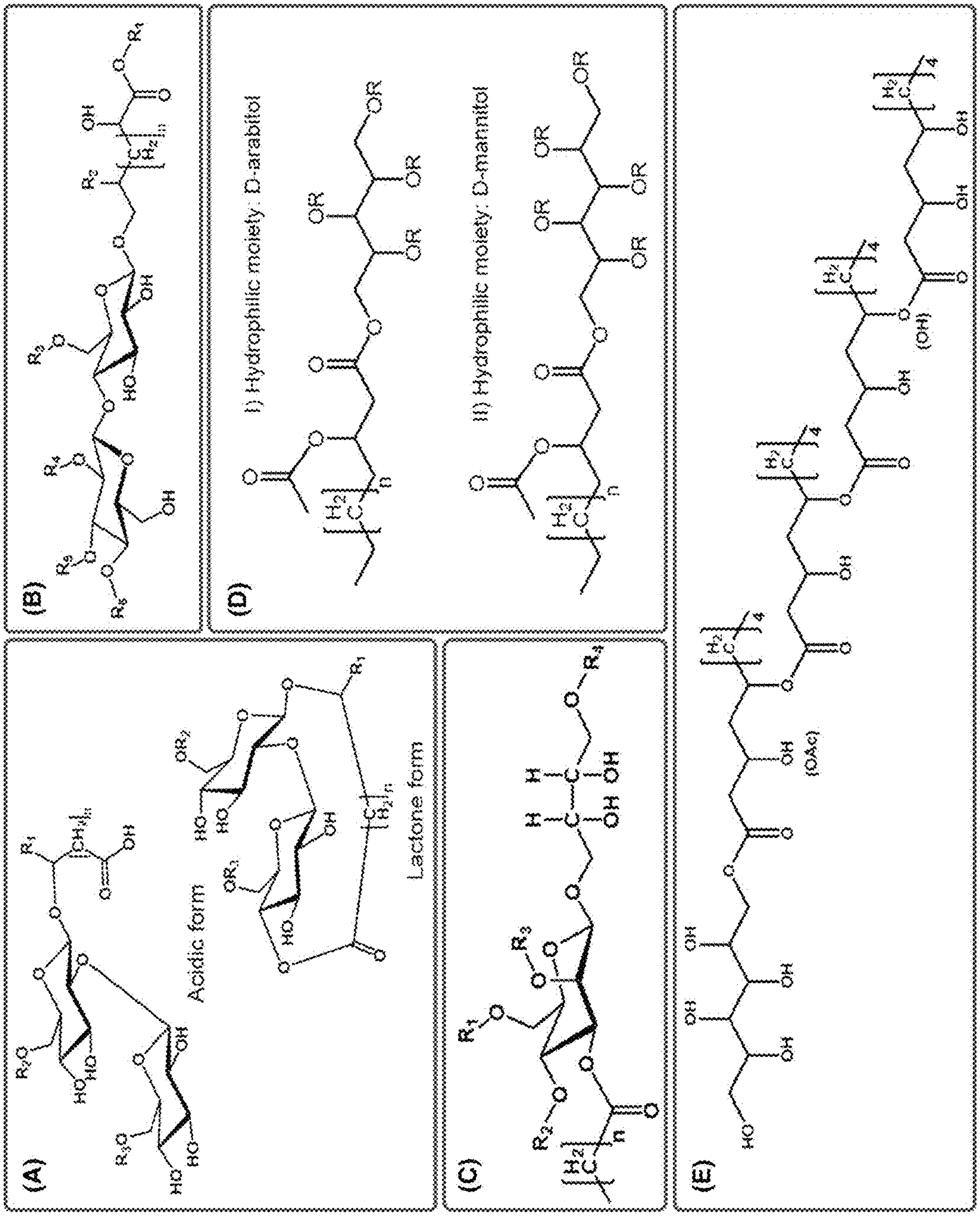
FIGS. 1A-E depicts structure of the five known yeast secreted GL biosurfactants: (A) sophorolipids, (B) cellobiose lipids, (C) mannosylerythritol lipids, (D) polyol esters of fatty acids and (E) liamocins.

Methods, yeast cultures and polyol lipid compositions are described herein, based in part on the discovery of yeast species that convert hydrophilic carbon sources (e.g., simple sugars) into lipids, and then secrete them into the medium in a form that can be harvested without solvent extraction—a breakthrough that addresses obstacles of harvesting and extraction.

The methods, yeast cultures and polyol lipid compositions described herein enable development of yeast-based processes to convert lignocellulosic hydrolysates into a suite of products, including easily harvested lipids, e.g., for use in the sustainable production of biodiesel and other oleochemicals.

The methods, yeast cultures and polyol lipid compositions described herein overcome the disadvantages of the prior art in that polyol lipids are produced by these yeasts in commercially relevant quantities without provision of hydrophobic substrate or substrates. The methods, yeast cultures and polyol lipid compositions described herein entail the use of yeasts in phylum Basidiomycota, class Microbotryomycetes, order Sporidiobolales, genera *Rhodotorula, Rho-*

*dosporidiobolus* and *Sporobolomyces* for conversion of glucose or other carbohydrates to polyol lipids Polyol lipids are produced by these yeasts in commercially relevant quantities without provision of hydrophobic substrate or substrates.

Yeasts have been used as model organisms for decades. The first eukaryotic genome to be sequenced was that of the yeast *Saccharomyces cerevisiae* [26], in part due to its long history of use as a model organism for genetics research, and for food, beverage and biofuel production. *Starmerella bombicola* is a model yeast for conversion of carbohydrate plus fatty acids or vegetable oil to secreted glycolipids (e.g., sophorolipids) [18, 27, 28].

We identified basidiomycetous yeast strains that are able to secrete polyol lipids, particularly, polyol esters of fatty acids (PEFAs). In addition to producing between 0.7 and 12 g/L intracellular lipids, primarily triacylglycerols (TAGs), these yeasts are able to secrete up to an estimated 25-27 g/L crude polyol lipids.

Basidiomycetous yeasts in the order Sporidiobolales are able to directly convert less expensive simple sugars into significant quantities of secreted polyol lipids (e.g., polyol esters of fatty acids (PEFAs)), opening up opportunities to use these polyol lipids for a broader range of consumer and industrial surfactant applications. The present yeast cultures, methods and polyol lipid compositions facilitate the development of an economically favorable industrial process for biosurfactant production.

The advantages of these basidiomycetous yeasts for production of polyol lipids include without limitation:

- Tulloch, et al, partially determined glycolipid structures produced in low yields (between 1-2 g/L) by basidiomycetous species. See Tulloch, et al., 1964, supra. Tulloch 1964 determined the components of the secreted glyocolipids: the polyols arabitol and mannitol plus trace amounts of xylitol, hydroxy fatty acid and acetate. But Tulloch 1964 did not determine how these pieces were assembled or the mixture of PEFA molecules, as provided herein. Moreover, the basidiomycetous yeast and yeast cultures described herein produce and secrete significant quantities of polyol esters of fatty acids, as much as to 25-27 g/L, or more, when fed only hydrophilic carbon sources (e.g., simple sugars such as glucose, xylose or sucrose).
- The polyol lipids are secreted, so cell harvesting and lysis are not necessary.
- The polyol lipids are heavier than water and yeast cells, so inexpensive gravimetric techniques can be used to harvest them.
- The oils are extracellular and mostly insoluble in water, so organic solvent extraction is not required. This greatly reduces both facility construction and processing costs, decreases environmental impact and increases operational safety.
- Because the cells producing the polyol esters of fatty acids need not be harvested or lysed, a continuous or fed-batch culture system further reduces costs.

2. Methods of Producing Polyol Lipids

Generally, the methods entail culturing a population of basidiomycetous yeast cells in a yeast culture containing relatively high concentrations of a hydrophilic (e.g., non-hydrophobic) carbon source and low concentrations of nitrogen, and with or without the presence of a hydrophobic carbon source.

a. Yeast Cultures

Provided are yeast cultures for producing one or more polyol lipids (e.g., polyol esters of fatty acids (PEFAs)) according to the methods described herein. In varying embodiments, the yeast culture comprises a population of basidiomycetous yeast cells, a hydrophilic (e.g., non-hydrophobic) carbon source, and at least about 1 g/L total polyol lipid, e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L total polyol lipid, e.g., up to about 450 g/L of total polyol lipid. The one or more polyol lipids are extracellularly secreted by the yeast cells into the media and can be harvested without cell lysis and extracted without use of organic solvent.

In varying embodiments, the culture does not comprise one or more hydrophobic carbon sources. In varying embodiments, the culture comprises one or more hydrophobic carbon sources. In varying embodiments, the one or more hydrophobic carbon sources are selected from the group consisting of oils, hydrocarbons, unsaturated hydrocarbons, fatty acids, fatty esters including glycerides and mixtures thereof, alcohols, diols, sterols, waste streams, hydrolysates, and mixtures thereof. In varying embodiments, the one or more hydrophobic carbon sources include an oil, e.g., a mineral oil, animal oil, a plant oil, a microbial oil (e.g., an algal oil, a yeast oil, a bacterial oil), a fish oil, a vegetable oil or a nutseed oil, e.g., canola oil, rapeseed oil, olive oil, almond oil, walnut oil, peanut oil, coconut oil, or others, or mixtures thereof. In varying embodiments, the one or more hydrophobic carbon sources comprise at least 8 carbon atoms, e.g., an alkane, fatty acid, fatty ester, alcohol, diol comprising 8 or more carbon atoms, e.g., from 8 to 24 carbon atoms. In varying embodiments, the one or more hydrophobic carbon sources are selected from a primary or secondary alcohol or diol having from about 4 to about 24 carbon atoms, e.g., having 8 or more carbon atoms, e.g., from 8 to 24 carbon atoms or from 8 to 14 carbon atoms. In varying embodiments, the one or more hydrophobic carbon sources are selected from an aliphatic linear or branched hydrocarbon, which may contain one or more substituents selected from the group consisting of —OR, —COOH, and an ester with a carbon chain length of about 4 to about 24 carbon atoms, e.g., having 8 or more carbon atoms, e.g., from 8 to 24 carbon atoms or from 8 to 14 carbon atoms.

In varying embodiments, the culture comprises less than about 2% (w/v) nitrogen, e.g., in the range of about 0.005% (w/v) to about 2% (w/v) nitrogen. In varying embodiments, the nitrogen source is selected from the group consisting of ammonia, ammonium salt, nitrate, nitrite, nucleotides, nucleosides, proteins, peptides, amino acids, urea and its derivatives, and mixtures thereof. In varying embodiments, the culture comprises about 0.05% (w/v) ammonium chloride.

In varying embodiments, the culture comprises one or more hydrophilic carbon sources at a concentration of at least about 0.2% (w/v), e.g., in the range of about 0.2% (w/v) to about 70% (w/v), e.g., in the range of about 0.2% (w/v) to about 10%, 20%, 30%, 40%, 50% or 60% (w/v). In varying embodiments, the culture comprises a carbon to nitrogen ratio of about 5:1 to about 400:1, e.g., from about 10:1 to about 200:1, from about 20:1 to about 100:1, e.g., from about 25:1 to about 75:1, e.g., from about 30:1 to about 70:1, e.g., from about 40:1 to about 60:1, e.g., from about 30:1 to about 40:1, e.g., using a nitrogen source that can be consumed or utilized by the yeast cells.

In varying embodiments, the hydrophilic carbon source is selected from the group consisting of monosaccharides, oligosaccharides, polysaccharides, sugar alcohols, polyols, polyol lipids (e.g., polyol esters of fatty acids (PEFAs)), organic acids, esters, aldehydes, ketones, alcohols, waste streams, plant materials, lignocellulosic hydrolysates, industrial co-products and mixtures thereof. In varying embodiments, the hydrophilic carbon source is a monosaccharide, a disaccharide, an oligosaccharide or a polysaccharide and comprises one or more sugars selected from the group consisting of glucose, sucrose, xylose, galactose, rhamnose, arabinose, mannose, cellobiose, galacturonic acid, lactose, sophorose, glycerol, and mixtures thereof. In varying embodiments, the amount of air is increased by culturing the yeast in containers designed to create turbulent flow (e.g. baffled flasks). In varying embodiments, a device capable of simultaneously allowing gas exchange with the outer environment (e.g. a foam stopper in case of using Erlenmeyer baffled flasks) and maintaining the culture sterile is used.

In varying embodiments, the population of basidiomycetous yeast cells in the yeast culture comprises basidiomycetous yeast cells within the taxonomic class Microbotryomycetes. In varying embodiments, the population of basidiomycetous yeast cells comprises cells within the taxonomic order Sporidiobolales. In varying embodiments, the basidiomycetous yeast cells are within the *Rhodotorula glutinis* clade. In varying embodiments, the population of basidiomycetous yeast cells is from genera classified within the taxonomic order Sporidiobolales selected from the group consisting of *Rhodosporidium* sp., *Sporidiobolus, Rhodotorula*, and *Sporobolomyces*. In varying embodiments, the population of basidiomycetous yeast cells comprises *Rhodosporidium* cells. In varying embodiments, the *Rhodosporidium* cells are *Rhodotorula babjevae* (syn. *Rhodosporidium babjevae*) cells. In varying embodiments, the population of basidiomycetous yeast cells comprises one or more species selected from the group consisting of *Rhodotorula babjevae* (syn. *Rhodosporidium babjevae*), *Rhodotorula diobovata* (syn. *Rhodosporidium diobovatum*), *Rhodotorula kratochvilovae* (syn. *Rhodosporidium kratochvilovae*), *Rhodotorula paludigena* (syn. *Rhodosporidium paludigenum*), *Rhodosporidium* aff. *paludigenum*, and *Rhodotorula dairenensis*. In varying embodiments, the cells do not comprise *Pseudohyphozyma bogoriensis* (syn. *Rhodotorula bogoriensis*), a species in class Microbotryomycetes but not in order Sporidiobolales [29].

In varying embodiments, the yeast culture comprises hydrophilic carbon source (e.g., a mono- or di-saccharide, e.g., glucose and/or sucrose) (30 g/L), yeast extract (1.5 g/L), ammonium chloride (0.5 g/L), potassium phosphate monobasic (7.0 g/L), sodium phosphate dibasic (5.0 g/L), magnesium sulfate hexahydrate (1.5 g/L) and micronutrient solution comprised of various salts (10 mL/L). In varying embodiments, the yeast culture comprises an iron salt. Illustrative iron salts that find use include without limitation iron chloride (II) & (III), iron sulfate (II) & (III), iron nitrate (II) & (III), iron phosphate (II) & (III), fumarate, iron edetate, iron citrate, iron malate, iron oxalate, iron tartrate, iron succinate, iron acetate, in their anhydrous or their hydrated states, and organometallic complexes thereof. In varying embodiments, the culture comprises an iron salt in a concentration in the range of about 0.001 mg/L to about 10 g/L, e.g., from about 1 mg/L to about 0.5 g/L, e.g., from about 0.01 g/L to about 0.5 g/L. In varying embodiments, the yeast culture is supplemented with extra hydrophilic carbon source (e.g., a mono- or di-saccharide, e.g., glucose and/or sucrose) to a concentration of at least about 50 g/L, 75 g/L, 100 g/L, 125 g/L, 150 g/L, 175 g/L, 200 g/L, 225 g/L, 250 g/L, 275 g/L or 300 g/L.

b. Methods of Producing Polyol Lipids

Provided are methods of producing one or more polyol lipids (e.g., polyol esters of fatty acids (PEFAs)), comprising culturing a population of basidiomycetous yeast cells in a yeast cell culture comprising a hydrophilic carbon source, wherein the culture does not comprise one or more hydrophobic carbon sources, whereby the basidiomycetous yeast cells produce and secrete one or more polyol lipids. As discussed above, the yeast cells are grown in a yeast cell culture media having a high carbon to nitrogen (C/N) ratio. In varying embodiments, the hydrophilic carbon source (e.g., a mono- or di-saccharide, e.g., glucose and/or sucrose) is added after the population of basidiomycetous yeast cells reaches stationary phase. Embodiments of the yeast culture are as described above. When culturing yeast cells in the herein described yeast cultures and according to the methods described herein, at least about at least about 1 g/L polyol lipid, e.g., at least about 2 g/L, 3 g/L, 4 g/L, 5 g/L, 6 g/L, 7 g/L, 8 g/L, 9 g/L, 10 g/L, 11 g/L, 12 g/L, 13 g/L, 14 g/L, 15 g/L, 20 g/L, 25 g/L, 30 g/L, 35 g/L, 40 g/L, 45 g/L, 50 g/L, 100 g/L, 150 g/L, 200 g/L, 250 g/L, 300 g/L, 350 g/L, 400 g/L polyol lipid, e.g., up to about 450 g/L of polyol lipid, are secreted into the yeast culture medium.

The population of basidiomycetous yeast cells is cultured in the yeast cell culture medium under conditions sufficient for yeast cell growth and polyol lipid production and secretion. The embodiments of illustrative yeast cultures are as described above and herein. For example, in certain embodiments, the yeast cells are cultured at a temperature of about 24 °C with continuous agitation (e.g., in shake flasks, e.g., baffled shake flasks, e.g., at about 200 rpm) for time period sufficient for yeast cell growth and polyol lipid production and secretion, e.g., for about 6 hours to about 168 hours post inoculation with yeast cells, e.g., about 6, 12, 24, 48, 72, 96, 120, 144, 168 hours post inoculation with yeast cells. The yeast cells are further provided with a sufficient amount of a hydrophilic carbon source, e.g., as described above. The yeast cells are supplied with sufficient levels of oxygen to metabolize the hydrophilic carbon source into a polyol lipid containing a hydroxylated fatty acid as part of its structure, e.g., in baffled flasks stoppered with porous stoppers or membranes designed to allow passage of gas without compromising the sterility of the system, or in biorcactors capable of controlling the amount of oxygen (e.g. in the form of air or mixtures of air and oxygen) through regulation of gas supply and/or agitation. In varying embodiments, the yeast cells are grown in a buffered media that requires no pH adjustment. For example, in certain embodiments the yeast cells are cultured at pH values of about 6.5. In varying embodiments, total polyol lipids are measured and determined after 1, 2, 3, 4, 5, 6, 7 or 8 days growth.

During and after growth in shake flasks, a hydrophobic liquid settles to the bottom of the growth flask or bioreactor. In varying embodiments, the one or more polyol lipids secreted by the yeast cells has density in the range of about 1.00 g/mL to about 1.10 g/mL, e.g., from about 1.08 g/mL to about 1.09 g/mL. The secreted extracellular polyol lipids have significantly lower processing costs because the costs of lysing of cells and separation of oil from cell debris can be eliminated or greatly reduced.

In varying embodiments, the yeast populations are cultured under conditions that promote aeration of the cultures and oxygenation of the cells. Such strategies can include culturing lower culture volumes in larger flasks, e.g., employing a culture volume to container volume ratio of 1:3 or greater, e.g., 1:4, 1:5, 1:6, 1:7, 1:8, 1:9, 1:10 or greater, employing baffled flasks; covered the culture flask in such a manner to allow air/oxygen exchange, e.g., with a foam stopper; and/or exposing the yeast cultures to a super-oxygenated atmosphere. In some embodiments, the yeast culture comprises dissolved oxygen at a concentration of a least about 10%, e.g., at least about 15%, 20%, 25%, 30%, 35%, 40%, 45%, and up to 60%, 70%, 80%, 90%, 100% dissolved oxygen, e.g., from about 15% to about 80%, e.g., from about 20% to about 60% dissolved oxygen. When cultured in a bioreactor, the yeast culture can fill as much as 90% of the container volume, and the oxygen can be bubbled into the culture.

In varying embodiments, the methods further comprise the step of isolating and/or purifying the one or more polyol lipids from the yeast culture. Because the polyol lipids are extracellularly secreted from the yeast cells, and the yeast cell culture does not contain a hydrophobic carbon source, the one or more polyol lipids can be isolated and/or purified from the yeast cell culture without cell lysis or extraction requiring an organic solvent. The secreted polyol lipid compounds are denser than water and can be recovered inexpensively using separation methods based on density, including without limitation centrifugation, continuous decanting, or passive settling. The extracellular polyol lipids can be washed from the rest of the cells and culture components by subsequent washing steps using water, yielding a product containing moisture to up to 8%. The moisture content does not affect the extracellular polyol lipid performance or its functionality. In varying embodiments, the moistened extracellular polyol lipid can be further dried using known techniques, e.g., tumble drying, plate drying, flash drying, freeze drying and other known techniques. In varying embodiments, both wet and dry extracellular lipids can be further fractionated to obtain pure molecular species by thin layer chromatography, HPLC, preparative chromatography, and other known techniques. Accordingly, in varying embodiments, the basidiomycetous yeast cells can be cultured under batch, fed-batch or continuous feed processing conditions. In varying embodiments, using batch, fed-batch or continuous feed cultivation conditions in which the culture is repeatedly or continuously fed allowing the cells to continue producing product, up to several hundred grams of substrate e.g., 100 g, 150 g, 200 g, 250 g, 300 g, 350 g, 400 g, 450 g or 500 g) per liter can be obtained. In varying embodiments, polyol lipid yields of about 0.5 g/L to about 30 g/L can be obtained from yeast cultures comprising in the range of about 10 g/L to about 250 g/L glucose. In varying embodiments, polyol lipid yields of about 14 g/L to about 17 g/L can be obtained from yeast cultures comprising about 50 g/L glucose.

Embodiments of the one or more polyol lipids and polyol lipid composition profiles produced according to the methods are as described below.

3. Polyol Lipid and Polyol Lipid Profiles Produced According to the Methods

Polyol lipid biosurfactants include polyol esters of fatty acids (PEFAs) and liamocins. In varying embodiments, the one or more polyol lipids in the yeast cultures, produced according to the methods, and/or in the polyol lipid compositions isolated and/or purified from the yeast cultures comprise one or more polyol esters of fatty acids (PEFAs). In varying embodiments, the one or more polyol lipids are free of any hydrophobic carbon source.

Polyol esters of fatty acids are amphiphilic molecules comprising a sugar alcohol, e.g., a D-mannitol and/or a D-arabitol, esterified to the carboxyl end of a 3-hydroxy fatty acyl moiety, which may or may not be acetylated. The non-esterified hydroxy groups of the sugar alcohol may or may not be acetylated as well (See, FIG. 1). In varying embodiments, the one or more polyol lipids produced are a mixture of similar compounds containing (R)-3-hydroxy fatty acyl moieties with varying chain lengths, in the range of about 10 to 24 carbons, preferably in the range between 12 to 20 carbons. In varying embodiments, the (R)-3-hydroxy fatty acyl moieties can present varying degrees of unsaturation in the range of about 0 to 6, e.g., in the range between 2 to 5. In varying embodiments, the non-esterified hydroxy groups of the sugar alcohol can be esterified to acetyl groups. In varying embodiments the sugar alcohol can be fully acetylated. In varying embodiments, the sugar alcohol can be non-acetylated. In varying embodiments, acetylations can range between these two states.

In varying embodiments, the one or more polyol lipids in the yeast cultures, produced according to the methods, and/or in the polyol lipid compositions isolated and/or purified from the yeast cultures comprise one or more polyol esters of fatty acid (PEFAs) listed in Table 4, below. In varying embodiments, the polyol lipid sugar alcohol moiety comprises a 5 carbon polyol, which can be D-arabitol or L-arabitol. In varying embodiments, the polyol lipid sugar alcohol moiety comprises a 6 carbon polyol, which can be D-mannitol or L-mannitol. In varying embodiments, the one or more polyol lipids comprise a fatty acid comprising from 10 to 24 carbon atoms in length. In some embodiments, the polyol lipid sugar alcohol moiety is attached or bound carboxyl end of the fatty acid. In some embodiments, the fatty acid is hydroxylated at position Δ-3 from the carboxyl end. In some embodiments, the hydroxyl group in position Δ-3 may or may not be acetylated.

In varying embodiments, the one or more polyol lipids in the yeast cultures, produced according to the methods, and/or in the polyol lipid compositions isolated and/or purified from the yeast cultures comprise a polyol lipid (e.g., PEFA) profile comprising:

i) at least about 20%, e.g., at least about 25%, 30%, 35%, 40%, up to about 45% of an acetylated C16:0 (R)-3-hydroxy fatty acid esterified to D-arabitol comprising 4 acetylations (Molecular Formula: $C_{31}H_{52}O_{12}$);

ii) at least about 5%, e.g., at least about 6%, 7%, 8%, 9%, 10%, 15%, 20%, up to about 25%, of an acetylated C18:0 (R)-3-hydroxy fatty acid esterified to D-arabitol comprising 4 acetylations (Molecular Formula: $C_{33}H_{56}O_{12}$); and/or iii) at least about 5%, e.g., at least about 6%, 7%, 8%, 9%, 10%, 15%, up to about 20% of an acetylated C18:0 (R)-3-hydroxy fatty acid esterified to D-mannitol comprising 4 acetylations (Molecular Formula: $C_{34}H_{58}O_{13}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising at least about 25%, e.g., at least about 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising:

i) at least about 5%, e.g., at least about 6%, 7%, 8%, 9%, 10%, 15%, up to about 18%, of an acetylated C18:0 (R)-3-hydroxy fatty acid esterified to D-mannitol comprising 3 acetylations (Molecular Formula: $C_{32}H_{56}O_{12}$);

ii) at least about 1%, e.g., at least about 2%, 3%, 4%, 5%, 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

iii) at least about 5%, e.g., at least about 6%, 7%, 8%, 9%, 10%, 15%, 20%, up to about 25%, of an acetylated C18:0 (R)-3-hydroxy fatty acid esterified to D-mannitol comprising 4 acetylations (Molecular Formula: $C_{34}H_{58}O_{13}$);

iv) at least about 15%, e.g., at least about 16%, 17%, 18%, 19%, 20%, 25%, 30%, 35%, 40%, 45%, up to about 50% of an acetylated C16:0 (R)-3-hydroxy fatty acid esterified to D-arabitol comprising 4 acetylations (Molecular Formula: $C_{31}H_{52}O_{12}$); and/or v) at least about 10%, e.g., at least about 11%, 12%, 13%, 14%, 15%, 16%, 17%, 18%, 19%, 20%, 25%, 30%, up to about 35% of an acetylated C18:0 (R)-3-hydroxy fatty acid esterified to D-arabitol comprising 4 acetylations (Molecular Formula: $C_{33}H_{56}O_{12}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising:

vi) at least about 2%, e.g., at least about 3%, 4%, 5%, 6%, 7%, 8%, 9%, 10%, up to about 12%, of an acetylated C16:0 (R)-3-hydroxy fatty acid esterified to D-mannitol comprising 5 acetylations (Molecular Formula: $C_{34}H_{56}O_{14}$); and/or vii) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol (Molecular Formula: $C_{36}H_{60}O_{14}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising:

i) at least about 1%, e.g., at least about 2%, 3%, 4%, 5%, 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, 30%, 35%, 40%, up to about 45%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$); and/or v) at least about 15%, e.g., at least about 20%, 25%, 30%, 35%, 40%, up to about 45% of an acetylated C18:0 (R)-3-hydroxy fatty acid esterified to D-arabitol comprising 4 acetylations (Molecular Formula: $C_{33}H_{56}O_{12}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising:

i) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 4 acetylations (Molecular Formula: $C_{34}H_{58}O_{13}$);

ii) at least about 5%, e.g., at least about 6%, 7%, 8%, 9%, 10%, 15%, 20%, 25%, up to about 30%, of an acetylated C16:0 (R)-3-hydroxy fatty acid esterified to D-mannitol comprising 5 acetylations (Molecular Formula: $C_{34}H_{56}O_{14}$);

iii) at least about 10%, e.g., at least about 11%, 12%, 13%, 14%, 15%, 16%, 17%, 18%, 19%, 20%, up to about 25%, of an acetylated C18:0 (R)-3-hydroxy fatty acid esterified to D-mannitol comprising 5 acetylations (Molecular Formula: $C_{36}H_{60}O_{14}$);

iv) at least about 5%, e.g., at least about 6%, 7%, 8%, 9%, 10%, up to about 12%, of an acetylated C16:0 (R)-3-hydroxy fatty acid esterified to D-arabitol comprising 4 acetylations (Molecular Formula: $C_{31}H_{52}O_{12}$);

v) at least about 15%, e.g., at least about 20%, 25%, 30%, 35%, 40%, up to about 45%, of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4%, 5% up to about 6% of an acetylated C14:0 (R)-3-hydroxy fatty acid esterified to D-arabitol comprising 4 acetylations (Molecular Formula: $C_{29}H_{48}O_{12}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising:

i) at least about 5%, e.g., at least about 6%, 7%, 8%, 9%, 10%, up to about 12%, of an acetylated C18:0 (R)-3-hydroxy fatty acid esterified to D-mannitol comprising 4 acetylations (Molecular Formula: $C_{34}H_{58}O_{13}$);

ii) at least about 10%, e.g., at least about 11%, 12%, 13%, 14%, 15%, 16%, 17%, 18%, 19%, 20%, up to about 25%, of an acetylated C16:0 (R)-3-hydroxy fatty acid esterified to D-mannitol comprising 5 acetylations (Molecular Formula: $C_{34}H_{56}O_{14}$);

iii) at least about 5%, e.g., at least about 6%, 7%, 8%, 9%, 10%, up to about 12%, of an acetylated C18:0 (R)-3-hydroxy fatty acid esterified to D-mannitol comprising 5 acetylations (Molecular Formula: $C_{36}H_{60}O_{14}$);

iv) at least about 15%, e.g., at least about 20%, 25%, 30%, 35%, 40%, up to about 45%, of an acetylated C16:0 (R)-3-hydroxy fatty acid esterified to D-arabitol comprising 4 acetylations (Molecular Formula: $C_{31}H_{52}O_{12}$);

v) at least about 35%, e.g., at least about 36%, 37%, 38%, 39%, 40%, up to about 45% of an acetylated C18:0 (R)-3-hydroxy fatty acid esterified to D-arabitol comprising 4 acetylations (Molecular Formula: $C_{33}H_{56}O_{12}$); and/or vi) at least about 0.5%, e.g., at least about 1%, 2%, 3%, 4% up to about 5%, of an acetylated C16:0 (R)-3-hydroxy fatty acid esterified to D-mannitol comprising 3 acetylations (Molecular Formula: $C_{30}H_{52}O_{12}$).

In varying embodiments, the one or more polyol lipids in the yeast cultures, produced according to the methods, and/or in the polyol lipid compositions isolated and/or purified from the yeast cultures comprise a polyol lipid (e.g. PEFA) profile comprising:

i) at least about 5%, e.g., at least about 6%, 7%, 8%, 9%, 10%, 15%, up to about 20%, of an acetylated C16:0 (R)-3-hydroxy fatty acid esterified to D-mannitol comprising 4 acetylations (Molecular Formula: $C_{32}H_{54}O_{13}$);

ii) at least about 45%, e.g., at least about 46%, 47%, 48%, 49%, up to about 50% of an acetylated C16:0 (R)-3-hydroxy fatty acid esterified to D-arabitol comprising 4 acetylations (Molecular Formula: $C_{31}H_{52}O_{12}$); and/or iii) at least about 5%, e.g., at least about 6%, 7%, 8%, 9%, 10%, up to about 12% of an acetylated C18:0 (R)-3-hydroxy fatty acid esterified to D-arabitol comprising 4 acetylations (Molecular Formula: $C_{33}H_{56}O_{12}$).

In varying embodiments, the one or more polyol esters of fatty acid (PEFAs) are selected from those listed in Table 4. In varying embodiments, the population of yeast cells in the yeast cell culture produces one or more polyol lipids having a polyol lipid (e.g. PEFA) profile according to the polyol lipid (e.g. PEFA) profiles provided in Tables 4A-C.

4. Compositions Comprising Polyol Lipids

Further provided are compositions comprising the one or more polyol lipids and/or having a polyol lipid (e.g. PEFA) profile as described above and herein. Surfactants (both petroleum and bio-based) are used in a broad variety of agricultural, nutritional, cosmetic, veterinary, therapeutic, and industrial applications due to their many activities. Activities include cleansers, detergents, wetting agents, anti-foam agents, emulsifiers, dispersants (e.g., for cleanup of oil including spilled petroleum), and humectants. They are used in household and industrial cleansers and detergents, textiles, agrochemicals, photo chemicals, petroleum extraction, construction materials, adhesives, lubricants, mining, and the pulp and paper industry. Surfactants used in household and laundry detergents end up in the environment. The poor performance of petroleum-based surfactants with regard to sustainability, bio-accumulation, eco-toxicity and/or biodegradability is pushing development of bio-based replacements, or biosurfactants, which can be produced microbially from renewable feedstocks, have lower toxicity, and are biodegradable.

Major biosurfactants on the market include surfactin and emulsin, and a variety of glycolipids which are the major class of biosurfactants. Polyol lipids, including polyol ester of fatty acids (PEFAs, have potential to be renewable, low-toxicity, biodegradable alternatives to petroleum-based surfactants. Rhamnolipids are produced by a pathogenic bacterium, *Pseudomonas aeruginosa*. Sophorolipids, produced by non-pathogenic yeasts, are currently on the market as detergents, emulsifiers, wetting agents, dispersants and other activities. To our knowledge, at the time of filing of this application, polyol lipids are not commercially available.

Similar to sophorolipids and acetylated lactone forms of sophorolipids, the present polyol lipid compositions can find use as effective additives in shampoos, body washes, detergents, and cosmetic products. Certain polyol lipids may have anti-bacterial activity. The acidic forms can be effective ingredients in skin treatments and as moisturizing agents. Due to skin-friendly properties, the present polyol lipids can be used in cosmetics and pharmaceuticals. Glycolipid esters have proven to be excellent moisturizers for cosmetic uses (See, e.g., U.S. Pat. No. 4,297,340). Additional uses include spermicides and virucides (Shah, et al., *Antimicrob Agents Chemother.* (2005) 49 (10): 4093-100), septic shock antagonists, anticancer agents and protein inducers/repressors in microbial systems (See, e.g., Intl. Publ. No. WO 2007/073371 A1). Derivatives and modified polyol esters of fatty acids further have been shown to have antifungal activity (See, e.g., Intl. Publication No. WO2011/127101 and U.S. Patent Publ. No. 2012/022241).

Accordingly, further provided are polyol lipid compositions, e.g., comprising one or more of the polyol lipids described above and herein, and produced by the methods described herein. Also contemplated are derivatives of the polyol lipids described above and herein, and produced by the methods described herein, for example, derivatives of either the sugar alcohol or lipid moiety, including hydroxylated fatty acids, D-mannitol, D-arabitol and their derivatives, etc. In varying embodiments, the polyol lipid composition is one or more of a cleanser, a detergent, a wetting agent, an antifoam agent, an emulsifier, a surfactant, an emollient, a dispersant, a humectant, an anti-bacterial agent, an anti-viral agent, an anti-fungal agent, a spermicide an insecticide, a lubricant, an adhesive, a crystal modifier, an instantizer, a viscosity modifier, a mixing/blending aid, and/or a release agent.

The polyol lipid compositions find use in numerous applications, including without limitation, household and industrial cleansers and detergents, textiles, agrochemicals such as control of fungal and insect pests, food processing such as cleaning agents for fresh and frozen fruits, vegetables, meats and processed foods, food processing such as rheologic modifiers in food applications including doughs, pastas and emulsions such as mayonnaise, dressings, and syrups, food processing such as antiadherents, photo chemicals, petroleum extraction such as release agents for fracking, construction materials such as lubricants and demolding agents for brick, ceramic, cement and concrete, mining such as adjuvants in the coal industry, pulp and paper industry, cosmetics such as creams, foams, mousses, balms, ointments, personal care formulations such as shampoos, body washes, conditioners, soaps, creams, skin treatments, and moisturizing agents, therapeutics such as ointments and creams, spermicides, anti-viral and anti-cancer agents, leather auxiliary agents, fuel oil emulsification for improved atomization, yielding a more complete combustion, bioremediation of contaminated soils, groundwater and surface water, dust suppression in mines and quarries, release agents for asphalt truck beds, facilitates castable aqueous emulsions for the manufacture of explosives, ingredient in metal working fluids, and oleochemicals such as biodiesel, platform chemicals. Additional uses of the polyol lipid compositions produced by the present methods are described, e.g., in U.S. Patent Publication Nos. 2012/0022241 and 2013/0072414, hereby incorporated herein by reference for all purposes.

EXAMPLES

The following examples are offered to illustrate, but not to limit the claimed invention.

Example 1

Discovery of Synthesis and Secretion of Polyol Esters of Fatty Acids by Four Basidiomycetous Yeast Species in the Order Sporidiobolales This Example is published as Garay, et al., J Ind Microbiol Biotechnol. (2017) March 13 [PMID: 28289902], which is hereby incorporated herein by reference in its entirety for all purposes.

Materials and Methods

Chemicals and yeast strains. All chemicals were of analytical grade, except glucose (catalog number S25295B, Fisher Science Education PA, USA) which was technical grade.

Sixty-five yeast strains listed in Table 2. They were revived from cryopreserved stocks in the Phaff Yeast Culture Collection, University of California Davis phaf-fcollection.ucdavis.edu by streaking onto potato dextrose agar and incubating at room temperature up to 7 days. It must be noted that the species names of many yeast strains used in this study, and recent publications [11, 37-41] have been updated due to recent taxonomic revisions [53]. The strain ID number is unchanged. For example, yeast strain UCDFST 04-877 was formerly called *Rhodosporidium babjevae* [11, 37-41], and is now called *Rhodotorula babjevae*. The former species name is listed as a synonym in Table 2.

Molecular identification. Strain identities were confirmed using ITS and partial 26S ribosomal sequencing by colony PCR using primers ITS1, ITS4 [54], NL1 and NL4 as previously described [12, 14]. Strains *Rhodotorula babjevae* UCDFST 67-478, UCDFST 06-542, UCDFST 04-830, UCDFST 67-102, *Rhodotorula mucilaginosa* UCDFST 10-221, UCDFST 67-64, and UCDFST 05-218 did not amplify with the cell lysis method previously described. Therefore, DNA was extracted and purified using the DNA Wizard Kit® (Cat. No. Promega, NY, USA) from 5 mL liquid PDB cultures inoculated with a loopful of fresh cells (≈0.02 g) streaked from a potato dextrose agar and incubated in 16 cm×150 mm disposable borosili-cate glass culture tubes (cat. number 14-961-31 Fisher Scientific, CA, USA) for 20 h. DNA extracts were successfully amplified and the corresponding PCR products were sequenced with the primers described above at The College of Biological Sciences UCDNA Sequencing Facility (University of California, Davis, CA, USA). The rest of the amplified sequences from the strains not requiring DNA extraction with the kit were sequenced with the primers described above at Beckman Coulter Genomics (Danver, MA, USA). In both cases, single pass Sanger sequencing techniques were used, and identification was performed with NCBI-BLAST [2] as previously described [12, 14].

Yeast growth conditions. A loopful of fresh cells (≈0.2 g) from a freshly grown plate was suspended in 5.0 mL of sterile deionized water. To prepare a seed culture, 500 μL of this inoculum were inoculated into 50 mL bioreaction tubes (part number 229475, Celltreat Scientific Products, Shirley, MA, USA) containing 9.5 mL of Medium A, a medium with high C:N ratio (68:1) known to induce lipid accumulation in oleaginous yeasts [11, 45]. Modified Medium A contains 50 g $L^{-1}$ glucose, 0.1 g $L^{-1}$ calcium chloride, 0.5 g $L^{-1}$ ammonium chloride, 1.5 g $L^{-1}$ yeast extract, 7.0 g $L^{-1}$ $KH_2PO_4$, 5 g $L^{-1}$ $Na_2HPO_4 \cdot 2H_2O$, 1.5 g $L^{-1}$ $MgSO_4 \cdot 7H_2O$, 0.08 g $L^{-1}$ $FeCl_3 \cdot 6H_2O$, 10.0 mg $L^{-1}$ Zn $SO_4 \cdot 7H_2O$, 0.1 mg $L^{-1}$ $MnSO_4 \cdot H_2O$, 0.1 mg $L^{-1}$ $CuSO_4$, and 0.1 mg $L^{-1}$ Co $(NO_3)_2$. The cultures were then grown for 24 h at 24 °C and 200 rpm in a rotary shaker incubator (Series 25, New Brunswick Scientific Co., Edison, NJ, USA). Five mL of this seed culture were then inoculated into 500 mL baffled Erlenmeyer flasks containing 95 mL Medium A containing 50 g $L^{-1}$ glucose, and stoppered with foam stoppers (Cat. #L800-D, Identi-Plugs®, Jacce Industrie, Inc., NY, USA). The cultures were incubated for 7 days at 24 °C and 200 rpm.

Cell pellets were harvested by centrifugation at 3220×g for 10 min and washed with sterile deionized water two times by centrifugation. The cell pellets were stored overnight at −80 °C and freeze-dried at −46 °C, 0.133 mbar (Freez-One® 4.5 L Freeze Dry System Model 7750020, Labconco®, Kansas City, MO, USA). The dry cells were weighed to estimate dry cell weight (DCW) in terms of grams of recovered dry cells per liter of culture. PEFA were recovered by one of the following methods:

When PEFA droplets were observed in the culture, 10 mL of culture were each transferred to three tared 15 mL conical tubes and centrifuged at 3220×g for 10 min at room temperature. PEFA that sedimented to the bottom of the bottles were aspirated using 9 inch Pasteur pipettes and transferred to tared 15 ml conical tubes. Because some PEFA mix with cells during pipetting, deionized sterile water was added to the mixture, which was then vortexed and centrifuged to further separate the PEFA layer from the cells. The cells were carefully resuspended in water and pipetted out from the PEFA. The PEFA were freeze dried overnight to remove moisture and weighed to estimate grams of recovered PEFA per liter culture.

If PEFA droplets were not observed in the culture, then 10 mL of whole culture were extracted twice with 40 mL of ethyl acetate in duplicate and the solvent was removed overnight using a vacuum speed concentrator (miVac Duo®, Genevac Inc., Stone Ridge, NY, USA) programmed for non-freezing solvents (e.g. ethyl acetate) at minimum working pressure (≤6 mm Hg) and 25 °C. The dry weight of the PEFA residue was recorded.

Product characterization. PEFA products were analyzed as previously described [7]. Native PEFA molecules were analyzed using reversed-phase liquid chromatography-electrospray ionization in positive mode with a quadrupole/time-of-flight mass spectrometer (RPLC-ESI(+)-QTOFMS) in MS and MS/MS modes. Aliquots containing 10 μg $mL^{-1}$ of crude PEFA in methanol were run through a system consisting of an Agilent 1290 Infinity LC system (Agilent Technologies) with a pump (G4220A), a column oven (G1316C), an autosampler (G4226A), and an Agilent 6550 iFunnel QTOFMS. Diluted samples were separated on an Acquity UPLC CSH C18 column (100×2.1 mm; 1.7 μm) coupled to an Acquity UPLC CSH C18 VanGuard pre-column (5×2.1 mm; 1.7 μm) (Waters). The column was maintained at 65 °C at a flow-rate of 0.6 mL $min^{-1}$. The mobile phases consisted of (A) acetonitrile/water (60:40, v/v) with ammonium formate (10 mM) and formic acid (0.1%) and (B) isopropanol/acetonitrile (90:10, v/v) with ammonium formate (10 mM) and formic acid (0.1%). The separation was conducted under the following gradient: 0 min 15% (B); 0-2 min 30% (B); 2-2.5 min 48% (B); 2.5-11 min 82% (B); 11-11.5 min 99% (B); 11.5-12 min 99% (B); 12-12.1 min 15% (B), 12.1-15 min 15% (B). A sample volume of 1 μL was used for the injection. Sample temperature was maintained at 4 °C. The QTOF instrument was operated in ESI(+) with the following parameters: MSI mass range: m/z 50-1700; MS/MS mass range: m/z 50-1700; collision energy: 20 eV; capillary voltage: 3 kV; nozzle voltage: 1 kV; gas temperature: 200 °C; drying gas (nitro-gen): 14 L $min^{-1}$; nebulizer gas (nitro-gen): 35 psi; sheath gas temperature: 350 °C; sheath gas flow (nitrogen): 11 L $min^{-1}$; acquisition rate MSI: 10 spectra $s^{-1}$; acquisition rate MS/MS: 13 spectra $s^{-1}$; total cycle time: 0.508 s; number of precursor ions per cycle: 4; mass range for selection of precursor ions: m/z 500-1200. The instrument was tuned using an Agilent tune mix (mass resolving power ~20,000 FWHM). A reference solution (m/z 121.0509, m/z 922.0098) was used to correct small mass drifts during the acquisition. Mass-Hunter Qualitative (B.05.00) and Quantitative (B.05.01) Analysis (Agilent) software programs were used for the data processing. For the identification of the structural fragments and structural assembly the software Mass Frontier 7.0 (Thermo Scientific, Palo Alto, CA, USA) was used.

Results

Screening of yeasts for PEFA synthesis and secretion. Sixty-five yeast strains were used in this study, including PEFA-secreting basidiomycetes *Rhodotorula babjevae* UCDFST 04-877 [7]. Table 3 lists the 19 strains belonging to 6 species that produced more than 1 g $L^{-1}$ net PEFA out of the 65 candidate yeasts. The LC-MS data revealed that overlap of triacylglycerols occurred in both strains whose PEFA was separated by physical sedimentation and water washing as well as those extracted with ethyl acetate. Therefore, a "purity percentage" is also included in Table 3, to indicate what percent of the crude extract is PEFA. Some strains carried over a conspicuously large amount of triacylglycerols, and little to no PEFA. Examples include 15 strains from the species *R. ruineniae, R. sphaerocarpa, R.* aff. *lusitaniae, S. salmonicolor, R. dairenensis, R. glutinis, S. pararoseus, S. johnsonii, C. minutum*, and *O. externus* which displayed purity coefficients of less than 80%, ranging from less than 1-71.6%.

The PEFA were detected visually when the PEFA phase separated from the culture with simple gravity separation such as centrifugation, or when extracted with ethyl acetate. The PEFA that settled in the bottom of the tubes had a density higher than water, approximately 1.08 g/L. A similar behavior was observed previously for LM and SL [52]. Fifteen strains produced at least 3 g/L net PEFA. *Rhodotorula* aff. *paludigena* UCDFST 81-84 produced 12.4 g/L PEFA and *Rhodotorula paludigena* UCDFST 81-492 produced 11.7 g/L when grown in 50 g/L glucose, ranking as the top two PEFA producers identified in the present study. All nineteen PEFA producing strains identified in the present study except *Rhodotorula kratochvilovae* UCDFST 05-632, and *Rhodotorula diobovata* UCDFST 08-225, produced at least 1 g/L net PEFA that appeared as visible droplets in the culture. For the latter two strains, PEFA was successfully extracted with ethyl acetate.

Figure 2:
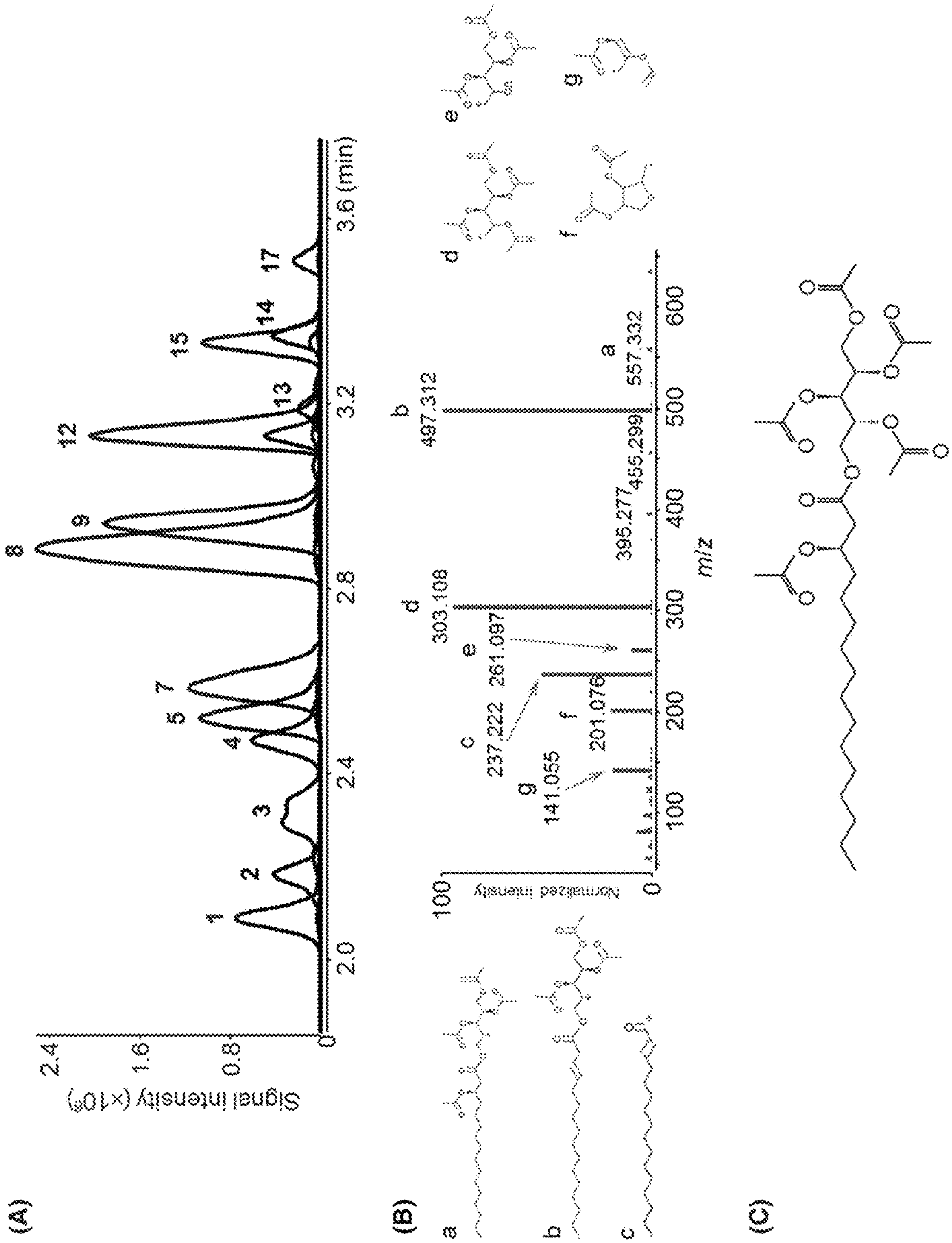
FIGS. 2A-C illustrate (A) Overlay of RPLC-ESI (+)-MS extracted ion chromatograms of extracellular lipids isolated from *Rhodotorula paludigena* UCDFST 81-492. For masses and peak annotations see Table 4; remaining unannotated lipids in this figure were either not detected or at low signal intensity. (B) MS/MS spectrum acquired at a collision energy of 20 eV and predicted fragment structures corresponding to (C) acetylated 3-hydroxypalmitic acid condensed with completely acetylated D-arabitol ($C_{31}H_{52}O_{12}$; peak 12 in FIG. 2A).
Figure 3:
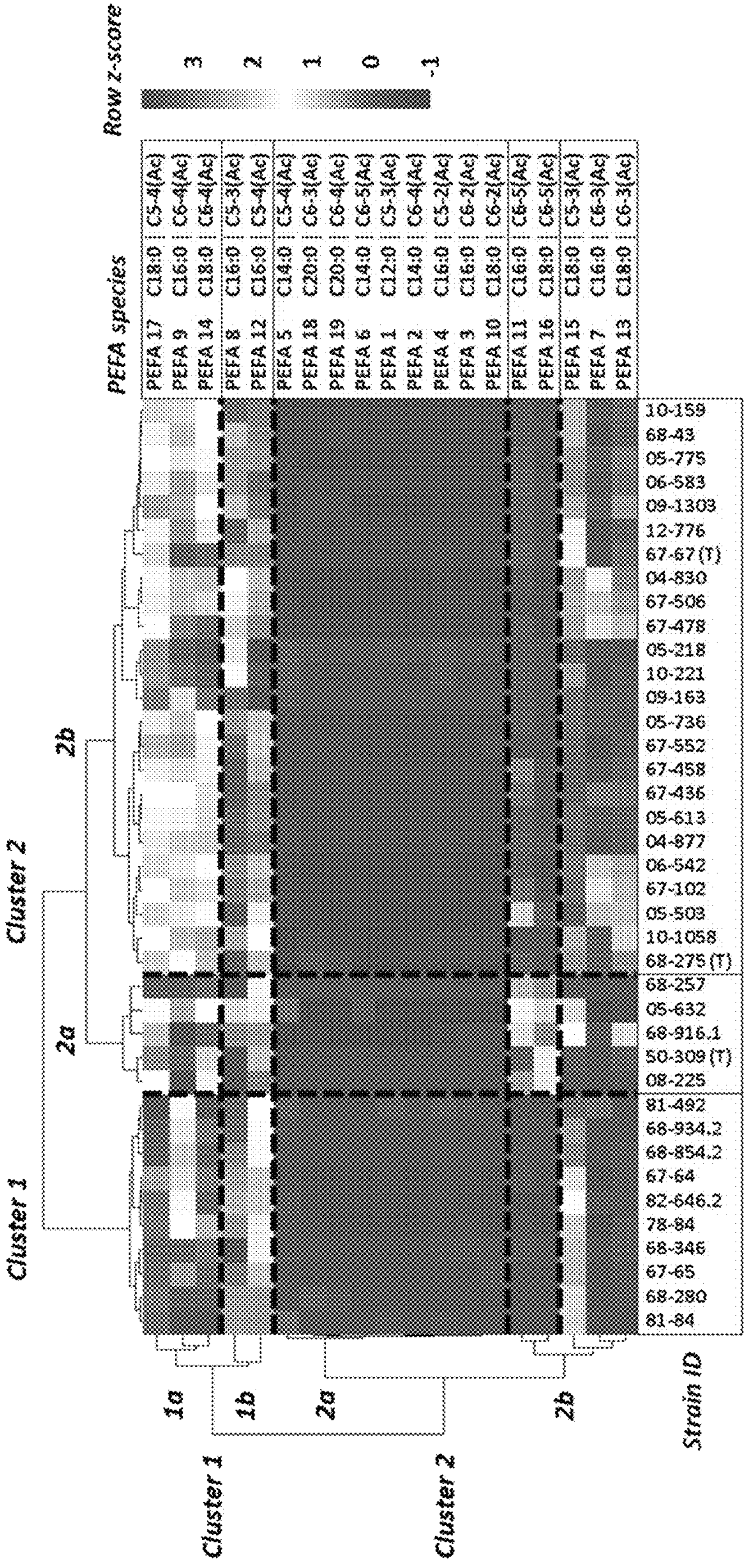
FIG. 3 illustrates unsupervised hierarchical clustering and heat map of yeast strains and PEFA species. The row z-score represents the deviation from the mean by standard deviation unit; red color indicates high percentage of PEFA; blue color indicates low percentage of PEFA. Yeast strain ID numbers are from the Phaff Yeast Culture Collection, University of California, Davis (color figure available online at link.springer.com/article/10.1007% 2Fs10295-017-1919-y).

Identification of PEFA products. Each PEFA-secreting yeast produced a mixture of nine to thirteen structurally similar PEFA, differing in the type of sugar alcohol attached (either D-mannitol or D-arabitol), the degree of acetylation in the sugar alcohol, and the chain length of the 3-hydroxy fatty acid. The hydroxy group on position 3 of the fatty acid is the only one present throughout the fatty acid chain and is acetylated in all PEFA congeners. A total of 19 different PEFA molecular congeners with different molecular weights and retention times were detected (Table 4). An example of a chromatogram showing the PEFA profile for *R. paludigena* UCDFST 81-492 and the MS/MS spectra of PEFA 12(acetylated C16:0 3-hydroxy fatty acid esterified to D-arabitol with 4 acetylations) with fragment annotations are provided in (FIG. 2*a, b*). PEFA were detected and PEFA profiles were determined for 20 strains that produced less than 1 g $L^{-1}$ PEFA, with varying purity percentages. The PEFA profiles of the yeast species fall into 3 clusters of PEFA species (FIG. 3). Details of relative abundance of each PEFA species for the 39 strains that secreted detectable amounts are presented in Table 5.

The most abundant and prevalent PEFA species among all the yeast PEFA profiles is PEFA 12 ($C_{31}H_{52}O_{12}$), present in at least 5% relative abundance across all strains that secreted trace or higher amounts of PEFA, and up to 12% relative abundance in 34 out of the 39 strains. Four more PEFA, namely PEFA 8 ($C_{29}H_{50}O_{11}$), PEFA 9 ($C_{32}H_{54}O_{13}$), PEFA 14 ($C_{34}H_{58}O_{13}$), and PEFA 17 ($C_{33}H_{56}O_{12}$) follow PEFA 12 in terms of abundance and prevalence. They are all present in at least 5% relative abundance in 30 strains and 12% relative abundance in 14 strains. PEFA 8, 12 and 17 contain D-arabitol in the structure, and PEFA 9 and 14 have D-mannitol. PEFA 12 and 17 are fully acetylated, while PEFA 8, 9 and 14 have one available hydroxy group. These characteristics are consistent with more hydrophobic physical properties.

The 19 PEFA identified in this study can be grouped into three categories in terms of their free hydroxy groups: (a) a more polar group with at least two free hydroxy groups. Six molecules belong to this group: PEFA 3 ($C_{23}H_{50}O_{11}$), PEFA 4 ($C_{27}H_{48}O_{10}$), PEFA 7 ($C_{30}H_{52}O_{12}$), PEFA 10 ($C_{30}H_{54}O_{11}$), PEFA 13 ($C_{32}H_{56}O_{12}$) and PEFA 18 ($C_{34}H_{60}O_{12}$). The strain producing the most abundant polar PEFA was *Rhodotorula babjevae* UCDFST 68-916.1, with 26.6% relative abundance; (b) a less polar group with only one free hydroxy group. Seven out of the 19 molecules are grouped here, namely PEFA 1 ($C_{27}H_{46}O_{11}$), PEFA 2 ($C_{30}H_{50}O_{13}$), PEFA 8 ($C_{29}H_{50}O_{11}$), PEFA 9 ($C_{32}H_{54}O_{13}$), PEFA 14 ($C_{34}H_{58}O_{13}$), PEFA 15 ($C_{31}H_{54}O_{11}$) and PEFA 19 ($C_{36}H_{62}O_{13}$). The strain producing the most abundant fraction of these molecules was *Occultifur externus* UCDFST 68-934.2, with 66.9% relative abundance; (c) a non-polar group with all the hydroxy groups being acetylated. Six molecules classify in this group: PEFA 5 ($C_{29}H_{48}O_{12}$), PEFA 6 ($C_{32}H_{52}O_{14}$), PEFA 11 ($C_{34}H_{56}O_{14}$), PEFA 12 ($C_{31}H_{52}O_{12}$), PEFA 16 ($C_{36}H_{60}O_{14}$) and PEFA 17 ($C_{33}H_{56}O_{12}$). The strain displaying the highest abundance is *Rhodotorula dairenensis* UCDFST 68-257 with 88.4% relative abundance. Seven out of the 19 molecules contain D-arabitol, while the rest contain D-mannitol. No other sugar alcohols were detected. Fatty acid chain length ranged from 12 to 20 carbons, in even number increments. The most abundant chain length identified was hexadecanoate (C16:0), and the second most abundant was octadecanoate (C18:0). The highest abundance of medium chain length (C12:0 and C14:0) molecules was seen in *Rhodotorula kratochvilovae* UCDFST 05-632, while the highest abundance of C20:0 was observed for *Cystobasidium minutum* UCDFST 68-280. In average, seven molecular species accounted for 78.5% of PEFA abundance across the whole panel, namely PEFA 12 ($C_{29}H_{50}O_{11}$), PEFA 8 ($C_{32}H_{54}O_{13}$), PEFA 17 ($C_{34}H_{56}O_{14}$), PEFA 9 ($C_{31}H_{52}O_{12}$), PEFA 14 ($C_{34}H_{58}O_{13}$), PEFA 15 ($C_{31}H_{54}O_{11}$) and PEFA 11 ($C_{33}H_{56}O_{12}$) with decreasing relative abundance percentages: 21.4, 12.6, 11.5, 10.5, 9.7, 7.7 and 5.1%, respectively. No unsaturated fatty acyl chains were present in the 19 PEFA identified. This is a striking difference from the intracellular oils reported for these strains, where the bulk of the acyl chains in the intracellular triacylglycerols are unsaturated [11, 41], in some cases with up to 3 double bonds in the acyl chains. The nineteen structures are described in Table 4.

Unsupervised hierarchical clustering and heat map of strains and PEFA species revealed three types of patterns (see FIG. 3). The first denotes an association between *Rhodotorula paludigena/Rhodotorula* aff. *paludigena* species and a PEFA profile where PEFA 8 is highly predominant, followed by PEFA 12. These PEFA contain D-arabitol. The second pattern involves *Rhodotorula babjevae strains* and a PEFA profile dominated by PEFA 12, which is fully acetylated and contains D-arabitol as well. The third pattern includes *Rhodotorula kratochvilovae* and *Rhodotorula diobovata*, the other two newly identified secreting yeasts, and a high percentage of PEFA 11, 16 and 17. The first two PEFA contain D-mannitol. There are two exceptions to these tendencies, namely *R. babjevae* UCDFST 68-916.1 and *R. paludigena* UCDFST 09-163, which display different patterns compared to the other strains from the same species. These results show that PEFA secretion is primarily species specific, but both qualitative and quantitative strain differences exist as well. The applications for the different PEFA compositions may differ: PEFA from *R. babjevae* should be more hydrophobic than those coming from *R. paludigena* due to fewer free hydroxy groups. More research is needed to identify optimal applications for each PEFA profile.

Discussion

Before this study, only seven species of yeasts were known to naturally synthesize and secrete PL (see Table 1). This study increased the number of known species by adding species *Rhodotorula diobovata, Rhodotorula kratochvilovae, Rhodotorula paludigena, Rhodotorula* aff. *paludigena*. The taxonomic term "aff." or affinis means it is a new species; the closest valid species is *R. paludigena*. The UCDFST (Phaff Yeast Culture Collection) strain used in this study is the only known representative of this novel species. These yeast species belong to a taxonomic clade that was recently revised [53], which resulted in genus name changes, as described above.

These four yeasts produce at least 1 g $L^{-1}$ with PEFA purities above 80%. Additional yeasts producing trace amounts of PEFA are also reported. The two highest PEFA producers in the present study, namely *R.* aff. *paludigena* UCDFST 81-84 and *R. paludigena* UCDFST 81-492, achieved glucose conversions of 0.25 and 0.23 g of PEFA per gram of glucose respectively. Cajka et al. obtained values equivalent to a glucose conversion of 0.086 g of PEFA per gram of glucose from *R. babjevae* UCDFST 04-877 and Tulloch et al. in the 1960s documented values equivalent to a glucose conversion of 0.05 g of PEFA per gram of glucose. from *R. azoricum* (previously called *R. glutinis* or *R. graminis*) CBS 4648 [7, 46]. The *R. paludigena* and *R.* aff. *paludigena* strains thus converted 2.9 times and 2.7 times more glucose into PEFA compared to Cajka et al. and 5 times and 4.6 times more compared to Tulloch et al. [7, 46] All these new PEFA-secreting yeasts present significant opportunity to expand our knowledge of synthesis and secretion of structurally complex products, which may be beneficial for development of tools for synthesis and secretion of a broad variety of oleochemicals beyond PEFA and other GL.

The function of PEFA as well as other yeast GL in natural ecosystems has been the subject of speculation. For example, the GL may aid in modifying leaf surface permeability, possibly facilitating uptake of hydrophobic carbon sources such as the long chain waxes present in the cuticle on the surface of leaves [6, 35]. Other theories include secretion of yeast GL as an external form of carbon storage [51]. Others have suggested the use of GL as anti-microbial and anti-fungal compounds [36, 42]. Indeed, LM were shown to display selective antibacterial activity against six Streptococcus species [4], even with different polyol head groups [28]. Many of the PEFA-secreting yeasts identified in this study were isolated from plant surfaces and insects, consistent with the first theory. PEFA production is more apparent in the *Rhodotorula glutinis/graminis* clade, comprising *R. glutinis, R. graminis, R. babjevae* and *R. diobovata* species, as well as in the *R. paludigena* clade, which appear in the top branches the phylogenetic tree (See, FIG. 4 of Garay, et al., J Ind Microbiol Biotechnol. (2017) March 13 [PMID: 28289902]). PEFA production was negligible or undetected in other phylogenetic branches, suggesting an evolutionary pattern. Furthermore, the highest three producers (*R.* aff. *paludigena* UCDFST 81-84, *R. paludigena* UCDFST 81-492 and *R. babjevae* UCDFST 04-877) in the present work were originally isolated from plant surfaces (Table 3). Six more PEFA producing strains (*R. paludigena* UCDFST 09-163, *R. babjevae* UCDFST 67-458, *R. graminis* 05-503, *R. paludigena* 82-646.2, *R. babjevae* UCDFST 68-916.1, *R. graminis* UCDFST 05-613, sec Table 3) originated from plant surfaces/plant surface interactions as well. All these strains agglomerate in the *R. glutinis/graminis/babjevae* and the *R. paludigena* clades, which, as mentioned before, are located in the top branches of the phylogenetic tree depicted in FIG. 4 of Garay, et al., J Ind Microbiol Biotechnol. (2017) March 13 [PMID: 28289902]. Only two PEFA secreters identified in this study had source habitats unrelated to plant surfaces/plant surface interactions.

The production of PEFA by these yeasts differs significantly from that of previously known GL secreting yeasts such as SL-secreting *Starmerella bombicola* [51, 52] in that significant levels of PEFA are produced when cultivated on glucose as the carbon source, without a hydrophobic co-substrate. Similar results were reported previously for LM, where yields of up to 6.0 g $L^{-1}$ were obtained from 50 g $L^{-1}$ sucrose by *Aureobasidium pullulans* strain CU 39 (NRRL 58551) [24], and up to 35 g $L^{-1}$ from 120 g $L^{-1}$ glucose by *Aurcobasidium* sp. strain A-21M (although the latter value came from collecting 30 mL cultures to add up a total volume of about 1 L) [18]. The consequences of this property are quite significant for commercial production of PEFA for two reasons. First, the cost of glucose and other carbohydrates is significantly lower per kilogram than fatty acids and other hydrophobic co-substrates. Second, because residual lipids do not mingle with the GL product, purifying the product would involve simpler, less costly downstream processing. Commercial production of SL requires an ethyl acetate extraction to separate the SL and other hydrophobic materials from the spent media, then a hexane extraction to remove residual input vegetable oils or fatty acids from SL [3, 51, 52]. Elimination of one or both of these steps would reduce both capital expenses for constructing facilities appropriate to handle flammable solvents, and operating expenses. Phase separation of PEFA produced by the basidiomycete yeasts described in the study suggests that a production technology with fewer or no solvent extraction steps is feasible.

These newly identified PEFA-secreting yeast species all are classified in phylum Basidiomycota. Basidiomycetes are significantly different from ascomycetes morphologically, genetically, and physiologically. The phylum names derive from differences in spore formation. Basidiomycetes have much higher GC content, often over 60%, which can lead to difficulties with PCR and DNA sequencing. Basidiomycetes have a very different cell wall structure [33], which affects methods used to harvest intracellular products as well as genetic transformation techniques. As a result, fewer genome sequences and genetic tools are available for basidiomycetous yeasts [26]. However, some genomes have been sequenced, and genetic tools are being developed for some species with biotechnology value such as oleaginous yeast *Rhodotorula toruloides* [55], which, like the PEFA-secreting yeasts reported here, is in the taxonomic order Sporidiobolales.

Basidiomycetes do have some advantages. In general, basidiomycetes, including those in the order Sporidiobolales, are able to assimilate a broader range of carbon sources, particularly pentoses that are utilized by few of the GL-secreting ascomycete species [37]. Some basidiomycetous yeasts can also grow without supplemented vitamins, reducing culture medium costs.

The basidiomycetous yeasts identified in this study simultaneously synthesize high levels of intracellular triacylglycerols, accumulating 40-65% oil by dry weight [11, 41], indicating efficient citrate flux from mitochondria to generate a rich pool of acetyl COA, that will maintain the cytosolic fatty acid synthase actively producing fatty acids. This might explain why the yeast uses fatty acids as building blocks for PEFA synthesis [10]. In addition there are three main questions that remain unsolved and required further work towards elucidating the biosynthetic pathway of PEFA. First, further research is needed to understand how the hydroxylation on position Δ3 of the fatty acyl moiety occurs. In other yeast GL systems, like SL production by species *Starmerella bombicola*, hydroxylation on the ω or ω-1 position occurs through a cytochrome P-450 enzyme that presumably is bound to the outer leaflet of the endoplasmic reticulum [48, 49]. Second, there might be a reductive step in the biosynthetic pathway to convert glucose to D-mannitol. Stodola et al. reported the existence of an NADP dependent mannitol dehydrogenase displaying high activity in cell free extracts from extracellular PEFA producing strains of *Rhodotorula glutinis* [44]. More research is needed to identify the particular location of the enzyme, and how glucose is reduced to mannitol as part of the biosynthetic pathway [44]. In the case of LM, it was shown that *Aureobasidium pullulans* strain NRRL 50380 was able to directly incorporate (D-arabitol, D-xylitol, D-ribitol and L-threitol) into the LM structures, whereas dosing of sugars like sucrose, D-fructose, D-mannose and D-arabinose resulted in LM having mannitol head groups [28]. Therefore *A. pullulans* is able to convert the sugars to mannitol, and incorporate certain polyols into the LM backbone. It is not yet known whether the basidiomycetous yeasts involved in the present study are capable of such behavior, though structural similarities between LM and PEFA suggest this may be possible. Finally, the genomes of those yeasts secreting either SL, MEL or CL have been sequenced, and genes responsible for synthesis of GL have been identified [31], as has the transporter responsible for secretion in the case of SL [43]. The SL transporter protein has been described as an ABC transmembrane transporter [50]. Further analysis is required to determine whether these newly identified PEFA-secreting yeasts possess similar synthesis and/or secretion gene clusters.

This study validates the strategy of screening taxonomic relatives to identify additional yeast species with targeted properties. For example, Kurtzman measured SL production by 26 strains belonging to 18 yeast species in the taxonomic clade that includes *Starmerella bombicola* [21]. SL production was not detected in most strains tested. Because *Candida* is a polyphyletic genus, with hundreds of species spread across numerous taxonomic clades within Ascomycota, a strong knowledge of yeast taxonomy enabled selection of appropriate species within the targeted clade. Access to a large and diverse culture collection (the USDA-ARS Culture Collection, nrrl.naur.usda.gov/cgi-bin/usda/) also enabled that study.

There were many parallels in the current study. A large and diverse culture collection was tapped to acquire a diversity of native yeast strains. Roughly half of the known yeast species in the targeted clade within the order Sporidiobolales [19] were available from the Phaff Yeast Culture Collection (phaffcollection.udcavis.edu). Taxonomic expertise enabled selection of appropriate yeast species for this study, as the genus *Rhodotorula* is polyphyletic. Novel species currently lacking valid species names were discovered to produce PEFA in the current study. To indicate new species, the taxonomic term "*affinis*" (abbreviated "aff.") is placed between the genus and the species names of the closest valid species. A novel species found to synthesize and secrete PEFA in this study is *Rhodotorula* aff. *paludigena*. The Phaff collection strain is the only known strain of this species. Further work is needed to fully describe these species and assign a valid species name.

Variation of properties among strains of a given yeast species is often observed, such as enzymatic activity [12], inhibitor tolerance and lipid content [11, 41]. When Kurtzman measured SL production by two strains of *Candida apicola*, one produced the highest levels seen in their study, and the other did not produce detectable levels. Similarly, we found different PEFA secretion levels when comparing multiple strains of *Rhodotorula babjevae*. Strain UCDFST 04-877 secreted 8.7 g $L^{-1}$, strain UCDFST 05-775 secreted 6.3 g $L^{-1}$ and strain UCDFST 68-916.1 secreted 1.1 g $L^{-1}$ crude PEFA extract, all with purity above 97% suggesting different phenotypes within the same species.

The first two digits of the Phaff collection ID number indicate the year the strain was deposited in the collection. Yeasts listed in Table 3 were acquired over the last five decades. These observations dramatically demonstrate the importance of preserving a broad variety of microbes in professionally managed collections to enable future discoveries [5], of clearly designating the yeast collection and strain ID number in publications, and of utilizing the same strain in subsequent studies to ensure consistent results.

Discovery of these PEFA-secreting yeasts may aid in improving production of renewable, sustainable, environmentally friendly surfactants for use in household and industrial cleaning products, as well as many other applications. Further studies including optimization of production, technoeconomic analysis and examination of surfactant activities will help determine whether these yeasts have the potential to alter global surfactant production and use.

REFERENCES FOR EXAMPLE 1

1. (2014) Microbial biosurfactants market: Global industry analysis, size, share, growth, trends and forecast 2014-2020. Transparency Market Research, City, pp 1-74.
2. Altschul S F, Madden T L, Schäffer A A, Zhang J, Zhang Z, Miller W, Lipman D J (1997) Gapped BLAST and PSI-BLAST: a new generation of protein database search programs. Nucleic acids Res 25:3389-3402.
3. Ashby R D, McAloon A J, Solaiman D K, Yee W C, Reed M (2013) A process model for approximating the production costs of the fermentative synthesis of sophorolipids. J Surfactants Deterg 16:683-691.

4. Bischoff K M, Leathers T D, Price N P, Manitchotpisit P (2015) Liamocin oil from *Aureobasidium pullulans* has antibacterial activity with specificity for species of *Streptococcus*. J Antibiot 68:642-645.
5. Boundy-Mills K L, Glantschnig E, Roberts I N, Yurkov A, Casaregola S, Daniel H M, Groenewald M, Turchetti B (2016) Yeast culture collections in the twenty-first century: New opportunities and challenges. Yeast 33:243-260.
6. Bunster L, Fokkema N J, Schippers B (1989) Effect of surface-active *Pseudomonas* spp. on leaf wettability. Appl Environ Microbiol 55:1340-1345.
7. Cajka T, Garay L A, Sitepu I R, Boundy-Mills K L, Fiehn O (2016) Multiplatform Mass Spectrometry-Based Approach Identifies Extracellular Glycolipids of the Yeast *Rhodotorula babjevae* UCDFST 04-877. J Nat Prod 79:2580-2589.
8. Deleu M, Paquot M (2004) From renewable vegetables resources to microorganisms: new trends in surfactants. C R Chim 7:641-646.
9. Dhanarajan G, Sen R (2014) Cost Analysis of Biosurfactant Production from a Scientist's Perspective. Biosurfactants: Production and Utilization-Processes, Technologies, and Economics 159:153.
10. Garay L, Boundy-Mills K, German J (2014) Accumulation of high value lipids in single cell microorganisms: A mechanistic approach and future perspectives. J Agric Food Chem 62:2709-2727.
11. Garay L A, Sitepu I R, Cajka T, Chandra I, Shi S, Lin T, German J B, Fiehn O, Boundy-Mills K L (2016) Eighteen new oleaginous yeast species. J Ind Microbiol Biotechnol 43:887-900.
12. Golomb B L, Morales V, Jung A, Yau B, Boundy-Mills K L, Marco M L (2013) Effects of pectinolytic yeast on the microbial composition and spoilage of olive fermentations. Food Microbiol 33:97-106.
13. Gorin P, Spencer J, Tulloch A (1961) Hydroxy fatty acid glycosides of sophorose from *Torulopsis magnoliae*. Can J Chem 39:846-855.
14. Hamby K A, Hernández A, Boundy-Mills K, Zalom F G (2012) Associations of yeasts with spotted-wing *Drosophila* (*Drosophila suzukii; Diptera: Drosophilidae*) in cherries and raspberries. Appl Environ Microbiol 78:4869-4873.
15. Johnson V, Singh M, Saini V S, Adhikari D K, Sista V, Yadav N K (1992) Bioemulsifier production by oleaginous yeast *Rhodotorula glutinis* IIP-30. Biotechnol Lett 14:487-490.
16. Khan A S, Wilcox A S, Polymeropoulos M H, Hopkinsz I A (1992) Single pass sequencingand physical and genetic mapping of human brain cDNAs. Nat Genet 2:180-185.
17. Khan M S A, Singh B, Cameotra S S (2014) Biological Applications of Biosurfactants and Strategies to Potentiate Commercial Production. Biosurfactants: Production and Utilization—Processes, Technologies, and Economics 159:269.
18. Kurosawa T, Sakai K, Nakahara T, Oshima Y, Tabuch T (1994) Extracellular Accumulation of the Polyol Lipids, 3, 5-Dihydroxydecanoyl and 5-Hydroxy-2-decenoyl Esters of Arabitol and Mannitol, by *Aureobasidium* sp. Biosci Biotechnol Biochem 58:2057-2060.
19. Kurtzman C, Fell J, Boekhout T (2011) The Yeasts: A Taxonomic Study. Elsevier, Oxford.
20. Kurtzman C P (2012) *Candida kuoi* sp. nov., an anamorphic species of the *Starmerella* yeast clade that synthesizes sophorolipids. Intl J Syst Evol Microbiol 62:2307-2311.
21. Kurtzman C P, Price N P, Ray K J, Kuo T-M (2010) Production of sophorolipid biosurfactants by multiple species of the *Starmerella* (*Candida*) *bombicola* yeast clade. FEMS Microbiol Lett 311:140-146.
22. Makkar R S, Cameotra S S, Banat I M (2011) Advances in utilization of renewable substrates for biosurfactant production. AMB express 1:1-19.
23. Manitchotpisit P, Leathers T D, Peterson S W, Kurtzman C P, Li X-L, Eveleigh D E, Lotrakul P, Prasongsuk S, Dunlap C A, Vermillion K E, Punnapayak H (2009) Multilocus phylogenetic analyses, pullulan production and xylanase activity of tropical isolates of *Aurebasidium pullulans*. Mycol Res 113:1107-1120.
24. Manitchotpisit P, Price N P, Leathers T D, Punnapayak H (2011) Heavy oils produced by *Aureobasidium pullulans*. Biotechnol Lett 33:1151-1157.
25. Marchant R, Banat I M (2012) Microbial biosurfactants: challenges and opportunities for future exploitation. Trends Biotechnol 30:558-565.
26. Mccluskey K, Wiest A, Boundy-Mills K (2014) Chapter 4. Genome Data Drives Change at Culture Collections. Fungal Genomics. Springer Berlin Heidelberg, pp 81-96.
27. Mulligan C N (2005) Environmental applications for biosurfactants. Environ Pollut 133:183-198.
28. Price N P, Bischoff K M, Leathers T D, Cossé A A, Manitchotpisit P (2016) Polyols, not sugars, determine the structural diversity of anti-streptococcal liamocins produced by *Aureobasidium pullulans* strain NRRL 50380. J Antibiot DOI 10.1038/ja.2016.92.
29. Price N P, Manitchotpisit P, Vermillion K E, Bowman M J, Leathers T D (2013) Structural characterization of novel extracellular liamocins (mannitol oils) produced by *Aureobasidium pullulans* strain NRRL 50380. Carbohydr Res 370:24-32.
30. Renkin M (2003) Environmental profile of sophorolipid and rhamnolipid biosurfactants. Riv Ital Sostanze Gr 80:249-252.
31. Roelants S L, De Maeseneire S L, Ciesielska K, Van Bogaert I N, Soetaert W (2014) Biosurfactant gene clusters in eukaryotes: regulation and biotechnological potential. Appl Microbiol Biotechnol 98:3449-3461.
32. Ruinen J, Deinema M H (1964) Composition and properties of the extracellular lipids of yeast species from the phyllosphere. Antonie van Leeuwenhoek 30:377-384.
33. Ruiz-Herrera J, Ortiz-Castellanos L (2010) Analysis of the phylogenetic relationships and evolution of the cell walls from yeasts and fungi. FEMS Yeast Res 10:225-243.
34. Rust D, Wildes S (2008) Surfactants: a market opportunity study update. OmniTech International Ltd, Midland, MI.
35. Schreiber L, Krimm U, Knoll D, Sayed M, Auling G, Kroppenstedt R M (2005) Plant-microbe interactions: identification of epiphytic bacteria and their ability to alter leaf surface permeability. New Phytol 166:589-594.
36. Shah V, Badia D, Ratsep P (2007) Sophorolipids having enhanced antibacterial activity. Antimicrob Agents Chemother 51:397-400.
37. Sitepu I, Garay L, Sestric R, Levin D, Block D E, German J, Boundy-Mills K (2014) Oleaginous yeasts for biodiesel: Current and future trends in biology and production. Biotechnol Adv 32:1336-1360.

38. Sitepu I, Ignatia L, Franz A, Wong D, Faulina S, Tsui M, Kanti A, Boundy-Mills K (2012) An improved high-throughput Nile red fluorescence assay for estimating intracellular lipids in a variety of yeast species. J Microbiol Methods 91:321-328.

39. Sitepu I, Jin M, Fernandez J, Sousa L, Balan V, Boundy-Mills K (2014) Identification of oleaginous yeast strains able to accumulate high intracellular lipids when cultivated in alkaline pretreated corn stover. Appl Microbiol Biotechnol 98:7645-7657.

40. Sitepu I, Selby T, Zhu S, Lin T, Boundy-Mills K (2014) Carbon source utilization and inhibitor tolerance of 45 oleaginous yeast species. J Ind Microbiol Biotechnol 41:1061-1070.

41. Sitepu I R, Sestric R, Ignatia L, Levin D, Bruce German J, Gillies L A, Almada L A, Boundy-Mills K L (2013) Manipulation of culture conditions alters lipid content and fatty acid profiles of a wide variety of known and new oleaginous yeasts species. Bioresour Technol 144:360-369.

42. Sleiman J N, Kohlhoff S A, Roblin P M, Wallner S, Gross R, Hammerschlag M R, Zenilman M E, Bluth M H (2009) Sophorolipids as antibacterial agents. Ann Clin Lab Sci 39:60-63.

43. Soetaert W, Van Bogaert I (2010) Sophorolipid transporter protein. United States Patent Application #US 20120311741 A1.

44. Stodola F H, Deinema M H, Spencer J (1967) Extracellular lipids of yeasts. Bacteriol Rev 31:194.

45. Suutari M, Priha P, Laakso S (1993) Temperature shifts in regulation of lipids accumulated by Lipomyces starkeyi. J Am Oil Chem Soc 70:891-894.

46. Tulloch A, Spencer J (1964) Extracellular glycolipids of *Rhodotorula* species: The isolation and synthesis of 3-d-hydroxypalmitic and 3-d-hydroxystearic acids. Can J Chem 42:830-835.

47. Tulloch A, Spencer J, Deinema M (1968) A new hydroxy fatty acid sophoroside from *Candida bogoriensis*. Can J Chem 46:345-348.

48. Van Bogaert I N, Demey M, Develter D, Soetaert W, Vandamme E J (2009) Importance of the cytochrome P450 monooxygenase CYP52 family for the sophorolipid-producing yeast *Candida bombicola*. FEMS Yeast Res 9:87-94.

49. Van Bogaert I N, Develter D, Soetaert W, Vandamme E J (2007) Cloning and characterization of the NADPH cytochrome P450 reductase gene (CPR) from *Candida bombicola*. FEMS Yeast Res 7:922-928.

50. Van Bogaert I N, Holvoet K, Roelants S L, Li B, Lin Y C, Van de Peer Y, Soetaert W (2013) The biosynthetic gene cluster for sophorolipids: a biotechnological interesting biosurfactant produced by *Starmerella bombicola*. Mol Microbiol 88:501-509.

51. Van Bogaert I N, Saerens K, De Muynck C, Develter D, Soetaert W, Vandamme E J (2007) Microbial production and application of sophorolipids. Appl Microbiol Biotechnol 76:23-34.

52. Van Bogaert I N, Zhang J, Soetaert W (2011) Microbial synthesis of sophorolipids. Process Biochem 46:821-833.

53. Wang Q-M, Yurkov A, Göker M, Lumbsch H T, Leavitt S, Groenewald M, Theelen B, Liu X-Z, Boekhout T, Bai F-Y (2015) Phylogenetic classification of yeasts and related taxa within Pucciniomycotina. Stud Mycol 81:149-189.

54. White T J, Bruns T, Lee S, Taylor J (1990) Amplification and direct sequencing of fungal ribosomal RNA genes for phylogenetics. PCR protocols: a guide to methods and applications 18:315-322.

55. Zhu Z, Zhang S, Liu H, Shen H, Lin X, Yang F, Zhou Y J, Jin G, Ye M, Zou H (2012) A multi-omic map of the lipid-producing yeast *Rhodosporidium toruloides*. Nat Commun 3:1112.

Example 2

Multiplatform Mass Spectrometry-Based Approach Identifies Extracellular Glycolipids of the Yeast *Rhodotorula babjevae* UCDFST 04-877

This example is published as Cajka, et al., *J Nat Prod.* (2016) October 28; 79 (10): 2580-2589, hereby incorporated herein by reference in its entirety for all purposes.

In this example, a multiplatform mass spectrometry-based approach was used for clucidating extracellular lipids with biosurfactant properties produced by the oleaginous yeast *Rhodotorula babjevae* UCDFST 04-877. This strain secreted 8.6±0.1 g/L extracellular lipids when grown in a benchtop bioreactor fed with 100 g/L glucose in medium without addition of hydrophobic substrate, such as oleic acid. Untargeted reversed-phase liquid chromatography-quadrupole/time-of-flight mass spectrometry (QTOFMS) detected native glycolipid molecules with masses of 574-716 Da. After hydrolysis into the fatty acid and sugar components and hydrophilic interaction chromatography-QTOFMS analysis, the extracellular lipids were found to consist of hydroxy fatty acids and sugar alcohols. Derivatization and chiral separation gas chromatography-mass spectrometry (GC-MS) identified these components as D-arabitol, D-mannitol, (R)-3-hydroxymyristate, (R)-3-hydroxypalmitate, and (R)-3-hydroxystearate. In order to assemble these substructures back into intact glycolipids that were detected in the initial screen, potential structures were in-silico acetylated to match the observed molar masses and subsequently characterized by matching predicted and observed MS/MS fragmentation using the Mass Frontier software program. Eleven species of acetylated sugar alcohol esters of hydroxy fatty acids were characterized for this yeast strain.

Materials and Methods

General Experimental Procedures. LC-MS-grade solvents, mobile-phase modifiers, derivatives, and other reagents were obtained from Fisher Scientific, Hampton, NH, USA (water, acetonitrile, methanol), and Sigma-Aldrich/Fluka, St. Louis, MO, USA (2-propanol, hexane, dichloromethane, methyl tert-butyl ether, formic acid, ammonium formate, N-methyl-N-(trimethylsilyl)trifluoroacetamide, methoxyamine hydrochloride, trifluoroacetic anhydride, (R)-(−)-α-methoxy-α-(trifluoromethyl)phenylacetyl chloride, K2CO3, pyridine, hydrochloric acid, sodium hydroxide). Standards of ribitol, xylitol, D-(+)-arabitol, L-(−)-arabitol, dulcitol, glucitol, D-mannitol, D-(+)-glucose, and 17-L-[(2'-O-β-D-glucopyranosyl-β-D-glucopyranosyl)oxy]-cis-9-octadecenoic acid 1',4"-lactone 6',6"-diacetate were from Sigma-Aldrich, while 3-hydroxytetradecanoic acid (racemate), 3-hydroxypalmitic acid (racemate), and 3-hydroxystearic acid (racemate) were purchased from Matreya LLC, State College, PA, USA. (S)-3-Hydroxymyristic acid and (R)-3-hydroxymyristic acid were from Santa Cruz Biotechnology (Dallas, TX, USA). L-Mannitol was from Carbosynth (Compton, UK).

Extracellular Lipids. The oleaginous yeast *Rhodotorula babjevae* UCDFST 04-877 was obtained from the Phaff Yeast Culture Collection (UCDFST), University of California Davis, (32, 33) and its identity was confirmed by ITS and 26S ribosomal sequencing as described previously. (18) The GenBank accession numbers are KR149271 and KU609429, respectively. (18) The yeast was revived from cryopreserved stocks and plated on potato dextrose agar plates for up to 7 days at 26 °C. A colony was suspended in 5 mL of deionized sterile water, and 500 μL of the suspension was used to inoculate 9.5 mL of medium A(34) (with 50 g/L glucose) in 50 mL bioreaction tubes (Celltreat Scientific Products, Shirley, MA, USA) and incubated at 26 °C (room temperature) for 24 h. Samples of 5 mL of the culture were used to inoculate 95 mL of fresh medium A (with 50 g/L glucose) in 500 mL baffled flasks and incubated at 26 °C for 24 h. The contents of two flasks (corresponding to 200 mL of culture) were used to inoculate a 7 L bioreactor (Bioflo 3000, New Brunswick, Edison, NJ, USA) containing a working volume of 4 L of fresh medium A (with 100 g/L glucose) and incubated for 7 days at 26 °C with no pH adjustment. Constant dissolved oxygen of 40% was maintained throughout the fermentation. A time series sampling of 10 mL aliquots was extracted twice with 40 mL of ethyl acetate and dried overnight using a modular concentrator (Mi Vac Duo, Gardiner, NY, USA) set at room temperature and minimum working pressure (oscillating between 4-6 mbar) to recover 8.6±0.1 g/L PEFA from the culture at harvest. Around 50 mg of the crude extract was resuspended in 1 mL of ethyl acetate and stored at −80 °C for the chemical structure characterization.

RPLC-MS Analysis of Native Glycolipids. (1) Sample preparation: A 10 μg/mL solution was created via a two-step dilution, by first diluting 2 mg of the sample to 2 mL with methanol to an initial concentration of 1 mg/mL and vortexing for 10 s. In a second step, 10 μL of this solution was taken to a final concentration of 10 μg/mL by adding 990 μL of methanol. (2) RPLC-MS analysis: The system consisted of an Agilent 1290 Infinity LC system (Agilent Technologies) with a pump (G4220A), a column oven (G1316C), an autosampler (G4226A), and an Agilent 6550 iFunnel QTOFMS. Diluted samples were separated on an Acquity UPLC CSH C18 column (100×2.1 mm; 1.7 μm) coupled to an Acquity UPLC CSH C18 VanGuard precolumn (5×2.1 mm; 1.7 μm) (Waters). The column was maintained at 65 °C at a flow rate of 0.6 mL/min. The mobile phases consisted of (A) acetonitrile-water (60:40, v/v) with ammonium formate (10 mM) and formic acid (0.1%) and (B) 2-propanol-acetonitrile (90:10, v/v) with ammonium formate (10 mM) and formic acid (0.1%). The separation was conducted under the following gradient: 0 min 15% B; 0-2 min 30% B; 2-2.5 min 48% B; 2.5-11 min 82% B; 11-11.5 min 99% B; 11.5-12 min 99% B; 12-12.1 min 15% B; 12.1-15 min 15% B. A sample volume of 1 μL was used for the injection. Sample temperature was maintained at 4 °C. The QTOFMS instrument was operated in electrospray ionization (ESI) in positive mode with the following parameters: MSI mass range, m/z 50-1700; MS/MS mass range, m/z 50-1700; collision energy, 20 eV; capillary voltage, +3 kV; nozzle voltage, +1 kV; gas temperature, 200 °C; drying gas (nitrogen), 14 L/min; nebulizer gas (nitrogen), 35 psi; sheath gas temperature, 350 °C; sheath gas flow (nitrogen), 11 L/min; acquisition rate MS1, 10 spectra/s; acquisition rate MS/MS, 13 spectra/s; total cycle time, 0.508 s; number of precursor ions per cycle, 4; mass range for selection of precursor ions, m/z 500-1200. The instrument was tuned using an Agilent tune mix (mass resolving power ~20 000 fwhm). A reference solution (m/z 121.0509, m/z 922.0098) was used to correct small mass drifts during the acquisition. For the data processing, MassHunter Qualitative B.05.00 and Quantitative B.05.01 Analysis (Agilent) software programs were used.

Untargeted Analysis of Hydrolyzed Samples Using HILIC-MS. (1) Sample preparation: Samples (1 mg) were hydrolyzed in a 1.5 mL Eppendorf tube with (i) 0.3 mL of 1 M HCl in methanol at 55 °C for 2 h and (ii) 0.3 mL of 1 M NaOH in methanol at 55 °C for 2 h. After cooling to room temperature, both extracts were neutralized to pH 7. An aliquot of 10 μL was added to 1990 μL of an acetonitrile-water (80:20, v/v) mixture. After brief vortexing and centrifugation (13 400 rcf for 2 min), a 100 μL aliquot was transferred to a glass vial and submitted to HILIC-MS analysis. The reagent blanks were run in the same manner. (2) HILIC-MS analysis: The system consisted of an Agilent 1290 Infinity LC system (Agilent Technologies) with a pump (G4220A), a column oven (G1316C), an autosampler (G4226A), and an Agilent 6550 QTOFMS. Extracts were separated on an Acquity UPLC BEH Amide column (150×2.1 mm; 1.7 μm) coupled to an Acquity UPLC BEH Amide VanGuard precolumn (5×2.1 mm; 1.7 μm) (Waters). The column was maintained at 45 °C at a flow rate of 0.4 mL/min. The mobile phases consisted of (A) water with ammonium formate (10 mM) and formic acid (0.125%) and (B) 95:5 (v/v) acetonitrile-water with ammonium formate (10 mM) and formic acid (0.125%). The separation was conducted under the following gradient: 0 min 100% B; 0-2 min 100% B; 2-7.7 min 70% B; 7.7-9.5 min 40% B; 9.5-10.25 min 30% B; 10.25-12.75 min 100% B; 12.75-17.75 min 100% B. A sample volume of 1 μL was used for the injection. Sample temperature was maintained at 4 °C. The QTOFMS instrument was operated in electrospray ionization in negative mode with the following parameters: mass range, m/z 50-1700; capillary voltage, −3 kV; nozzle voltage, −1 kV; gas temperature, 200 °C; drying gas (nitrogen), 14 L/min; nebulizer gas (nitrogen), 35 psi; sheath gas temperature, 350 °C; sheath gas flow (nitrogen), 11 L/min; acquisition rate, 2 spectra/s. For the data processing, the MassHunter Qualitative B.05.00 (Agilent) software program was used.

GC-MS Analysis of Free Fatty Acids. (1) Sample preparation: Samples were prepared similarly to those in "Untargeted Analysis of Hydrolyzed Samples Using HILIC-MS". After cooling to room temperature, 800 μL of hexane was added to each tube. The tube was vortexed for 10 s followed by centrifugation at 13 400 rcf for 2 min. For direct analysis of fatty acid methyl esters, 10 μL of the extracts was further diluted with hexane (90 μL) and injected. For analysis of 3-trimethylsiloxy methyl esters, 10 μL of the hexane extracts was evaporated and 100 μL of MSTFA was added, followed by shaking at 37 °C for 30 min. The contents were transferred to a glass vial and submitted to GC-MS analysis. The reagent blanks were run in the same manner. (2) GC-MS analysis: The system consisted of an Agilent GC-MS system (Agilent Technologies) with a 7683 Series autosampler, a split/splitless injector, a 6890N GC system, and a quadrupole mass spectrometer 5975C. Injection parameters were as follows: injection volume, 0.2 μL; injector temperature, 225 °C; helium carrier gas flow, 1 mL/min for 28 min, 4 ml/min2 to 2 mL/min (hold for 8.5 min); splitless period, 0.5 min. For GC separation, a 30 m×0.25 mm, 0.25 μm DB-225 ms (Agilent) capillary column was used with an oven temperature program: 60 °C (0.5 min), 15 °C/min to 135 °C (hold 5 min), 15 °C/min to 235 °C (hold 10 min). MS detection parameters were as follows: acquisition rate, 3.2 scans/s; mass range, m/z 50-500; MS ion source temperature, 230 °C; MS quadrupole temperature, 150 °C; electron multiplier voltage, 2060 V. For the data processing, the MSD ChemStation E.02.00 (Agilent) software program was used. The NIST 14 spectral library (NIST, Gaithersburg, MD, USA) was used for identification of fatty acids.

GC-MS Analysis of Polyol Composition. (1) Sample preparation: Samples were prepared similarly to those in "Untargeted Analysis of Hydrolyzed Samples Using HILIC-MS". An aliquot of 10 μL of neutralized extracts was submitted to a two-step derivatization. First, 10 μL of 40 mg/mL methoxyamine hydrochloride in pyridine was added to dry extracts followed by shaking at 30 °C for 90 min. Second, 90 μL of MSTFA was added to the extracts followed by shaking at 37 °C for 30 min. The contents were diluted 100-fold with MSTFA, transferred to a glass vial, and submitted to gas chromatography-mass spectrometry (GC-MS) analysis. The reagent blanks were run in the same manner. (2) GC-MS analysis: The system consisted of an MPS2 automatic liner exchange system (Gerstel, Mülheim an der Ruhr, Germany), an Agilent 7890A GC system, and a time-of-flight Pegasus III mass spectrometer (Leco, St. Joseph, MI, USA). Injection parameters were as follows: injection volume, 0.5 μL; injector temperature, 50 °C ramped to 250 °C; helium carrier gas flow, 1 mL/min; splitless period, 25 s. For GC separation a 30 m×0.25 mm, 0.25 μm Rtx5Sil MS (Restek, Bellefonte, PA, USA) capillary column including an additional 10 m integrated guard column (Restek) was used with an oven temperature program: 50 °C (1 min), 20 °C/min to 330 °C (5 min). MS detection parameters were as follows: acquisition rate, 17 spectra/s; mass range, m/z 85-500; MS ion source temperature, 250 °C; transfer line temperature, 280 °C; MCP detector voltage, 1600 V. For the data processing, ChromaTOF 4.50 (Leco) software was used.

GC-MS Enantioselective Analysis of 3-Hydroxy Fatty Acids. (1) Sample preparation: Samples were prepared similarly to those in "Untargeted Analysis of Hydrolyzed Samples Using HILIC-MS". After cooling to room temperature, 800 μL of hexane was added to each tube. The tube was vortexed for 10 s followed by centrifugation at 13 400 rcf for 2 min. An aliquot of 20 μL was evaporated and submitted to derivatization. Pyridine (100 μL) and (R)-(−)-MTPA-Cl (10 μL) were added to dry extracts. The mixture was allowed to react at room temperature for 2 h. Then, water (700 μL) and solid K2CO3 (one spatula tip) were added, and the mixture was vortexed for 20 s followed by addition of MTBE (700 μL). The tube was vortexed for 20 s followed by centrifugation at 13 400 rcf for 2 min. An aliquot of 100 μL of the organic phase with methylated hydroxy fatty acids as their MTPA derivatives was evaporated to dryness. The residues were dissolved in 200 μL of MTBE and subjected to GC analysis. The reagent blanks were run in the same manner. Stock solutions of (R)-3-hydroxymyristic acid, (S)-3-hydroxymyristic acid, (R,S)-3-hydroxytetradecanoic acid (racemate), (R,S)-3-hydroxyhexadecanoic acid (racemate), and (R,S)-3-hydroxyoctadecanoic acid (racemate) were prepared in methanol (1 mg/mL). An aliquot of 10 μL was treated in the same way as yeast glycolipid samples. (2) GC-MS analysis: The system consisted of an Agilent GC-MS system (Agilent Technologies), a 7693 Series autosampler, a split/splitless injector, a 7890A GC system, and a quadrupole mass spectrometer 5977A. Injection parameters were as follows: injection volume, 1 μL; injector temperature, 250 °C; helium carrier gas flow, 1 mL/min; splitless period, 1.5 min. For GC separation a 30 m×0.25 mm, 0.25 μm SLB-5 ms (Supelco) capillary column was used with an oven temperature program: 60 °C (1.5 min), 40 °C/min to 180 °C (hold 2 min), 2 °C/min to 220 °C (hold 35 min), 10 °C/min to 250 °C (hold 15 min), 20 °C/min to 300 °C (hold 10 min). MS detection parameters were as follows: acquisition rate, 2.3 scans/s; mass range, m/z 50-600; MS ion source temperature, 230 °C; MS quadrupole temperature, 150 °C; electron multiplier voltage, 1700 V. For the data processing, the MSD ChemStation E.02.00 (Agilent) software program was used.

GC-MS Enantioselective Analysis of Polyols. (1) Sample preparation: Samples were prepared similarly to those in "Untargeted Analysis of Hydrolyzed Samples Using HILIC-MS". An aliquot of 20 μL of neutralized extracts was dried and submitted to derivatization. Dichloromethane (100 μL) and trifluoroacetic anhydride (100 μL) were added, the glass tubes were closed, and the samples were heated at 50 °C for 30 min. The reagents were evaporated to dryness, and the samples were dissolved in 200 μL of dichloromethane and submitted to GC-MS analysis. The reagent blanks were run in the same manner. Stock solutions of D- and L-arabitol and D- and L-mannitol were prepared in water (1 mg/mL). An aliquot of 10 μL was evaporated and submitted to derivatization. (2) GC-MS analysis: The system consisted of an Agilent GC-MS system (Agilent Technologies), a 7683 Series autosampler, a split/splitless injector, a 6890N GC system, and a quadrupole mass spectrometer 5975C. Injection parameters were as follows: injection volume, 0.2 μL; injector temperature, 200 °C; helium carrier gas flow, 1 mL/min; splitless period, 0.5 min. For GC separation a 25 m×0.25 mm, 0.25 μm Chirasil-Dex CB (Agilent) capillary column was used with an oven temperature program: 50 °C (0.5 min), 15 °C/min to 90 °C (hold 10 min), 1 °C/min to 100 °C, 20 °C/min to 200 °C (hold 10 min). MS detection parameters were as follows: acquisition rate, 1.26 scans/s; mass range, m/z 50-650; MS ion source temperature, 230 °C; MS quadrupole temperature, 150 °C; electron multiplier voltage, 2060 V. For the data processing, the MSD ChemStation E.02.00 (Agilent) software program was used.

Structure Elucidation of Polyol Esters of Fatty Acids. Mass Frontier v. 7.0 (Thermo Scientific, Palo Alto, CA, USA) was used for structure elucidation. MS/MS spectra were submitted in MSP format (text files containing spectra in the NIST MS Search format) and structures in MOL format prepared in ACD/ChemSketch software (Advanced Chemistry Development, Toronto, Ontario, Canada).

Results and Discussion

*R. babjevae* UCDFST 04-877 was isolated from a female olive fly trapped in an olive tree at UC Davis Campus, California, USA, in 2004. This yeast is of commercial interest since it has been described to produce high amounts of intracellular lipid mainly in the form of triacylglycerols (18) as well as being able to grow in carbon sources different from glucose (e.g., glycerol) and the presence of inhibitors. (20) *R. babjevae* is a close relative of *R. glutinis* and *R. graminis*, which were identified in the 1960s to produce a heavy oil. (9) Given the analytic capabilities of the time, researchers were able to identify only broadly the constituents of the oil, but failed to provide a detailed profile of the molecules and the exact structures as the present study is providing. These glycolipids are observed as droplets that sink when grown in a nutrient-limited media under aeration conditions like the one used in the present study.

Figure 4:
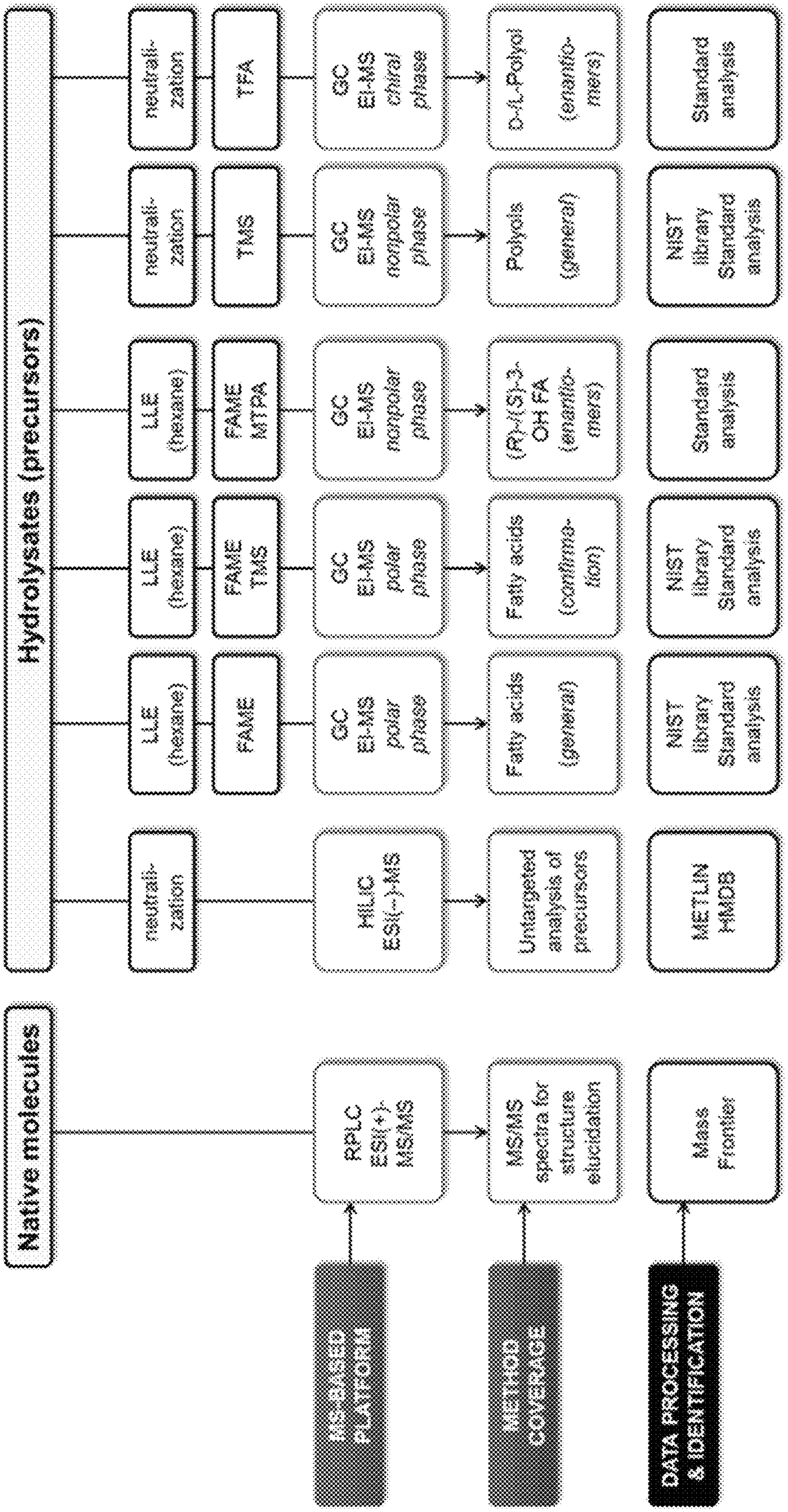
FIG. 4 illustrates General workflow of PEFA analysis. (FA, fatty acid; FAME, fatty acid methyl ester; GC-EIMS, gas chromatography-electron ionization mass spectrometry; HILIC-ESI(−) MS, hydrophilic interaction chromatography-negative electrospray ionization mass spectrometry; HMDB, Human Metabolome Database; LLE, liquid-liquid extraction; MTPA, (R)-(−)-α-methoxy-α-trifluoromethylphenylacetyl derivatives; RPLC-ESI(+)MS/MS, reversed-phase liquid chromatography-positive electrospray ionization-tandem mass spectrometry; TFA, trifluoroacetyl derivatives; TMS, trimethylsilyl derivatives).

A multiplatform mass spectrometry-based approach was used for identification and characterization of extracellular lipids produced by yeast *R. babjevae* UCDFST 04-877. FIG. 4 summarizes the workflow integrating the analysis of native molecules and the detailed characterization of hydrolyzed glycolipid precursors with the interpretation of mass spectra by in-silico software for structure elucidation. As discussed in subsequent sections, combining information obtained from both liquid chromatography-mass spectrometry (LC-MS) and gas chromatography-mass spectrometry (GC-MS) was essential for this task.

Figure 5:
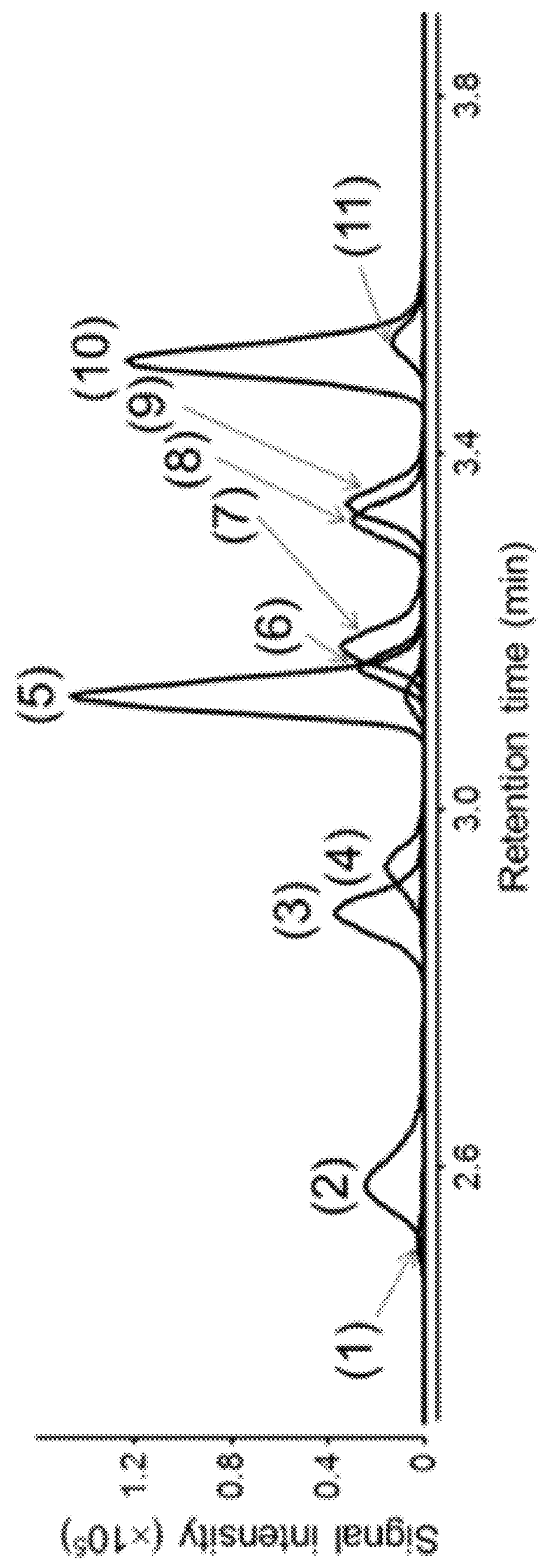
FIG. 5 illustrates an overlay of RPLC-ESI(+)MS extracted ion chromatograms of extracellular lipids isolated from *Rhodotorula babjevae* UCDFST 04-877. For masses and peak annotations see Table 5.

Structural Elucidation of Glycolipids by Chemical Analysis. The isolated extracts of glycolipids were separated using reversed-phase liquid chromatography (RPLC) on a C18 column followed by mass spectrometric (MS) detection in positive electrospray ionization (ESI) mode. Several features in the mass range of m/z 592-734 (as ammonium adducts) were found in the chromatogram (FIG. 5). For some of them, calculated elemental compositions matched those of published sophorolipid species. (21) However, follow-up analysis of a commercially available standard of sophorolipids containing dominantly 17-L-[(2'-O-β-D-glucopyranosyl-β-D-glucopyranosyl)oxy]-cis-9-octadecenoic acid 1',4"-lactone 6',6"-diacetate (>70% purity) showed that this glycolipid detected as $[M+NH4]^+$ and $[M+Na]^+$ molecular species had a retention time of 1.48 min, while the unknown glycolipid with the same elemental composition ($C_{34}H_{56}O_{14}$) and detected as the same molecular species eluted later at 3.16 min. Additional MS/MS analysis confirmed also differences in MS/MS spectra of these compounds. Because most of the elemental compositions obtained by the analysis of these native glycolipids did not provide satisfactory results in databases such as PubChem (22), SciFinder (23), or ChemSpider, (24) further experiments were conducted in order to determine the structure of these extracellular lipids.

Typical glycolipids consist of both lipophilic (e.g., fatty acid) and hydrophilic (e.g., sugar) constituents (25). Individual substructural components of glycolipids must be characterized by hydrolysis, under either acidic, alkaline, or enzymatic conditions (26). Hydrolysis using HCl and NaOH was used, both in methanol. The hydrolysis of sophorolipids consisting mainly of 17-L-[(2'-O-β-D-glucopyranosyl-β-D-glucopyranosyl)oxy]-cis-9-octadecenoic acid 1',4"-lactone 6',6"-diacetate was used as a positive control, which correctly provides 17-hydroxyoctadecenoic acid and glucose after hydrolysis treatment. This standard was used for quality control to ensure that the hydrolysis and derivatization reactions were working properly.

The hydrolysis was conducted at 55 °C for 2 h using (i) 1 M HCl in methanol and (ii) 1 M NaOH in methanol. The hydrolysates were neutralized for initial untargeted screening. A small volume of the extract was further diluted with acetonitrile-water (80:20, v/v) and separated using hydrophilic interaction chromatography (HILIC). Accurate mass detection in negative ESI was used because it permits detection of both fatty acids and sugars, typical constituents of glycolipids, including the determination of sum formulas, which is very hard to do in GC-MS. Using this method, both free fatty acids and polar constituents of these glycolipids were annotated (FIG. 6). Querying the Metlin (27) and HMDB (28) databases for the detected accurate masses, the fatty acid constituents were annotated as saturated hydroxy fatty acids with elemental compositions of $C_{14}H_{28}O_3$, $C_{16}H_{32}O_3$, and $C_{18}H_{36}O_3$. The polar constituents were found to be $C_5H_{12}O_5$ and $C_6H_{14}O_6$, indicating sugar alcohols (polyols), rather than the hexoses ($C_6H_{12}O_6$) observed in the sophorolipid control.

The position of the hydroxy group in the hydroxy fatty acids could not be identified by LC-MS/MS because current databases, including Metlin, lack MS/MS spectra for these compounds. In addition, the fragment ions of fatty acids are in general less abundant compared to precursor ions, making the identification even more difficult. Similarly, common sugar alcohols provide almost identical MS/MS spectra in LC-MS analyses. When retention time was used for reliable identification of different sugar alcohol standards under HILIC conditions, most sugar alcohols did not separate chromatographically under the conditions used in the present study. Gas chromatography-mass spectrometry (GC-MS) was therefore used, permitting improved peak capacity and availability of more comprehensive electron ionization (EI) libraries (e.g., NIST 14) for compounds such as fatty acids.

The hydrolyzed extracts were submitted to liquid-liquid extraction using hexane in order to isolate hydroxy fatty acid methyl esters. Because the hydrolysis was conducted in methanol solution, it was possible to inject the hexane extracts directly and detect the hydroxy fatty acids as methyl esters. However, for confirmation purposes, follow-up derivatization using N-methyl-N-(trimethylsilyl)trifluoroacetamide (MSTFA) was conducted for derivatization of the free hydroxy group of particular hydroxy fatty acids. Separation of both types of derivatized extracts was conducted on a GC column with a DB-225 ms polar stationary phase. The lipids were unambiguously assigned as hydroxy fatty acids with the hydroxy group in the β-position (C3), interpreting the characteristic fragments m/z 103 and m/z 175 for 3-hydroxy fatty acids detected as methyl esters or 3-trimethylsiloxy methyl esters, respectively (FIG. 7). These assignments were confirmed by analyzing authentic standards of 3-hydroxypalmitic and 3-hydroxystearic acids with matching electron ionization spectra and retention times For analysis of polar constituents, the reaction mixture was neutralized, followed by evaporation of small aliquots, conducting a two-step derivatization (methoximation and silylation) and separation of derivatives on a GC column with a nonpolar stationary phase (Rtx-5Sil MS). A series of authentic standards of sugar alcohols (C5-polyols: xylitol, D-/L-arabitol, ribitol; C6-polyols: D-/L-mannitol, dulcitol, glucitol) were derivatized and analyzed in the same way. Although only silylation is needed for derivatization of sugar alcohols, methoximation was also used because the hydrolysates might contain less volatile matrix components containing a carbonyl group. Indeed, methoximation was needed for derivatization of glucose during analysis of a sophorolipid standard (quality control). Matching retention time and mass spectra confirmed that the glycolipids contain arabitol and mannitol in their structures (FIG. 8).

Finally, an enantioselective analysis was performed using GC-MS in order to determine the D- or L-configuration of arabitol and mannitol and the R- or S-configuration of 3-hydroxy fatty acids. For enantioselective analysis of polyols, the chiral GC Chirasil-Dex CB phase was used, which permitted excellent separation of both D-/L-arabitol and D-/L-mannitol as trifluoroacetyl (TFA) derivatives. Analysis of the extracellular lipid hydrolysates confirmed that polyols are D-arabitol and D-mannitol (FIG. 9).

Under these conditions, the R- or S-configuration of 3-hydroxy fatty acids did not separate, mainly because they eluted at the upper temperature limit of the GC column (200 °C), where the effect of the chiral phase for separation is negligible. In order to verify the stereoconfiguration, 3-hydroxy fatty acids were converted into methyl esters followed by derivatization of the free 3-hydroxy group using (R)-(−)-

α-methoxy-α-trifluoromethylphenylacetyl chloride [(R)-(−)-MTPA-Cl, Mosher's reagent]. Corresponding MTPA-O-fatty acid methyl ester diastereomers (Mosher's esters) were then separated on a nonpolar GC column. (29) As FIG. 10 shows, extracellular lipid hydrolysates contained all detectable 3-hydroxy fatty acids in the R-configuration. When running R- and S-standards of 3-hydroxy C14:0, the S-diastereomer eluted earlier compared to its R-counterpart, as reported earlier (29, 30).

Structural Elucidation of Glycolipids by in-Silico Assembly. Similar components of extracellular glycolipids were reported for *R. glutinis* more than 50 years ago, (9) albeit without proving absolute configurations and without detailing the masses of the intact lipids. As stated before, the masses of the intact glycolipids were observed in the initial untargeted RPLC-QTOFMS screen in a mass range of m/z 592-734 (as ammonium adducts, Table 6). Condensing 3-hydroxystearate (or -palmitate) to mannitol or arabitol resulted in masses ranging between 406 and 464 Da. The difference from the observed masses indicated that these glycolipids were acetylated by 4-6 acetyl groups. In all cases, the hydroxy groups of the fatty acids were acetylated, as evidenced by treating 3-acetoxy fatty acid polyol esters with alkaline sodium methoxide, which led to the formation of α,β-unsaturated palmitic and stearic esters via β-elimination of acetic acid.

In order to confirm the complete, intact structures of the observed glycolipids, Mass Frontier software was used to evaluate and interpret mass spectral data based on acquired MS/MS spectra and proposed structures. (31) Structures were first submitted consisting of acetylated (R)-3-hydroxypalmitic acid and acetylated (R)-3-hydroxypalmitic stearic acid condensed to completely acetylated D-arabitol (Table 6 and FIG. 5; peaks 5 and 10). Predicted fragment structures matched accurate masses (<5 ppm) of fragments. This was further confirmed by comparing fragment structures differing by 28 Da (corresponding to C2H4 increase in the fatty acyl chain), containing fatty acid moieties such as m/z 497 (peak 5 in FIG. 5) vs m/z 525 (peak 10 in FIG. 5) or m/z 237 (peak 5, FIG. 5) vs m/z 265 (peak 10, FIG. 5), and fragments originating from acetylated D-arabitol, which were identical for both glycolipids (e.g., m/z 141, m/z 201, and m/z 303); see FIG. 11.

Less abundant glycolipids (Table 6 and FIG. 5; peaks 4 and 9) consisted of acetylated (R)-3-hydroxypalmitic acid or acetylated (R)-3-hydroxystearic acid, each condensed to partially acetylated D-mannitol with one nonacetylated hydroxy group in the sugar alcohol. All possible structures containing one free hydroxy group were probed; however, MS/MS prediction results using Mass Frontier were ambiguous with respect to the exact location of the nonacetylated hydroxy group. In fact, the observed peaks 4 and 9 in FIG. 5 might be a mixture of isomers. Fragment structures were observed differing in a 28 Da fatty acid moiety (e.g., m/z 237 vs m/z 265; m/z 467 vs m/z 495; m/z 527 vs m/z 555; m/z 569 vs m/z 597) and fragments originating from partially acetylated mannitol, which were identical for both glycolipids (e.g., m/z 153, m/z 231, m/z 273, m/z 333) (FIG. 12).

Combining all information collected, the full structures (3-hydroxy fatty acid, polyol, and degree of acetylation) of all detected glycolipids were completed (FIG. 13 and Table 6). Polyol lipids containing 3-hydroxypalmitic acid were the most abundant, followed by (R)-3-hydroxystearic acid and (R)-3-hydroxymyristic acid (detectable as trace amount, see peak 1 in FIG. 5). D-Arabitol was the dominating polyol unit in these extracellular lipids (Table 6 and FIG. 5).

Summary and Conclusions

This study demonstrated the combined use of several chromatography-mass spectrometry-based methods that together enabled the complete identification and characterization of 11 extracellular lipids produced by the yeast *R. babjevae* UCDFST 04-877, including absolute configurations. Use of LC-accurate mass fragmentation analysis was indispensable to obtain knowledge of the intact glycolipids, including final validation of complete structures by software-guided interpretation of the MS/MS spectra. However, LC-MS analysis alone was incapable of providing sufficient information for full elucidation, either with or without hydrolysis of the glycolipids into substructure components. GC-MS with various derivatization methods showed superior ability to distinguish sugar alcohol isomers, readily identified the hydroxy fatty acids, and proved to be required for defining absolute configuration analysis. This workflow shows the importance of combining different mass spectrometry-based methods together with structure elucidation using in-silico fragmentation software programs in order to determine structures of intact glycolipids.

REFERENCES FOR EXAMPLE 2

1. Lang, S.; Trowitzsch-Kienast, W. Biotenside; Springer: Wiesbaden, 2002.
2. Ines, M.; Dhouha, G. Carbohydr. Res. 2015, 416, 59-69, DOI: 10.1016/j.carres.2015.07.016
3. Reis, R. S.; Pacheco, G. J.; Pereira, A. G.; Freire, D. M. G. Biosurfactants: Production and Applications; 2013.
4. Merchant, R.; Banat, I. M. Trends Biotechnol. 2012, 30, 558-565, DOI: 10.1016/j.tibtech.2012.07.003
5. Banat, I. M.; Makkar, R. S.; Cameotra, S. S. Appl. Microbiol. Biotechnol. 2000, 53, 495-508, DOI: 10.1007/s002530051648
6. Edwards, K. R.; Lepo, J. E.; Lewis, M. A. Mar. Pollut. Bull. 2003, 46, 1309-1316, DOI: 10.1016/S0025-326X(03) 00238-8
7. Ruinen, J.; Deinema, M. H. Antonie van Leeuwenhoek 1964, 30, 377-84, DOI: 10.1007/BF02046750
8. Stodola, F. H.; Deinema, M. H.; Spencer, J. F. Bacteriol. Rev. 1967, 31, 194-213
9. Tulloch, A. P.; Spencer, J. F. T. Can. J. Chem. 1964, 42, 830-835, DOI: 10.1139/v64-123
10. Onghena, M.; Geens, T.; Goossens, E.; Wijnants, M.; Pico, Y.; Neels, H.; Covaci, A.; Lemiere, F. Anal. Bioanal. Chem. 2011, 400, 1263-1275, DOI: 10.1007/s00216-011-4741-9
11. Cajka, T.; Fiehn, O. TrAC, Trends Anal. Chem. 2014, 61, 192-206, DOI: 10.1016/j.trac.2014.04.017
12. Rathahao-Paris, E.; Alves, S.; Junot, C.; Tabet, J. C. Metabolomics 2016, 12, ARTN 10., DOI: 10.1007/s11306-015-0882-8
13. highchem.com, accessed May 21, 2016.
14 Duhrkop, K.; Shen, H. B.; Meusel, M.; Rousu, J.; Bocker, S. Proc. Natl. Acad. Sci. U.S.A. 2015, 112,12580-12585, DOI: 10.1073/pnas. 1509788112
15. Allen, F.; Greiner, R.; Wishart, D. Metabolomics 2015, 11, 98-110, DOI: 10.1007/s11306-014-0676-4
16. Tsugawa, H.; Kind, T.; Nakabayashi, R.; Yukihira, D.; Tanaka, W.; Cajka, T.; Saito, K.; Fiehn, O.; Arita, M.Anal. Chem. 2016, 88, 7946-7958, DOI: 10.1021/acs. analchem. 6b00770

17. Wolf, S.; Schmidt, S.; Muller-Hannemann, M.; Neumann, S. BMC Bioinf. 2010, 11, 148, DOI: 10.1186/1471-2105-11-148
18. Garay, L. A.; Sitepu, I. R.; Cajka, T.; Chandra, I.; Shi, S.; Lin, T.; German, J. B.; Fiehn, O.; Boundy-Mills, K. L. J. Ind. Microbiol. Biotechnol. 2016, 43, 887-900, DOI: 10.1007/s10295-016-1765-3
19. Wang, Q. M.; Yurkov, A. M.; Goker, M.; Lumbsch, H. T.; Leavitt, S. D.; Groenewald, M.; Theelen, B.; Liu, X. Z.; Boekhout, T.; Bai, F. Y. Stud. Mycol. 2015, 81, 149-189, DOI: 10.1016/j.simyco.2015.12.002
20. Sitepu, I.; Selby, T.; Lin, T.; Zhu, S.; Boundy-Mills, K. J. Ind. Microbiol. Biotechnol. 2014, 41, 1061-1070,DOI: 10.1007/s10295-014-1447-y
21. Kurtzman, C. P.; Price, N. P. J.; Ray, K. J.; Kuo, T. M. FEMS Microbiol. Lett. 2010, 311, 140-146, DOI: 10.1111/j.1574-6968.2010.02082.x
22. pubchem.ncbi.nlm.nih.gov, accessed Jan. 9, 2016.
23. scifinder.cas.org, accessed Jan. 9, 2016.
24. www.chemspider.com, accessed Jan. 9, 2016.
25. Kosaric, N.; Sukan, F. V. Biosurfactants: Production: Properties: Applications; Marcel Dekker: New York, 1993.
26. Rau, U.; Heckmann, R.; Wray, V.; Lang, S. Biotechnol. Lett. 1999, 21, 973-977, DOI: 10.1023/A:1005665222976
27. metlin.scripps.edu/metabo_search_alt2.php, accessed Feb. 16, 2016.
28. www.hmdb.ca/, accessed Feb. 16, 2016.
29. Jenske, R.; Vetter, W. J. Chromatogr. A 2007, 1146, 225-231, DOI: 10.1016/j.chroma.2007.01.102
30. Jenske, R.; Vetter, W. J. Agric. Food Chem. 2008, 56, 11578-11583, DOI: 10.1021/jf802772a
31. Kind, T.; Fiehn, O. Bioanal. Rev. 2010, 2, 23-60, DOI: 10.1007/s12566-010-0015-9
32. phaffcollection.ucdavis.edu, accessed May 27, 2016. 32.
33. Boundy-Mills, K. J. Ind. Microbiol. Biotechnol. 2012, 39, 673-680, DOI: 10.1007/s10295-011-1078-5
34. Suutari, M.; Priha, P.; Laakso, S. J. Am. Oil Chem. Soc. 1993, 70, 891-894, DOI: 10.1007/BF02545349

Example 3

Scaling Up into 7 L (4 L Culture Volume) Fed Batch Fermentors

Figure 14I:
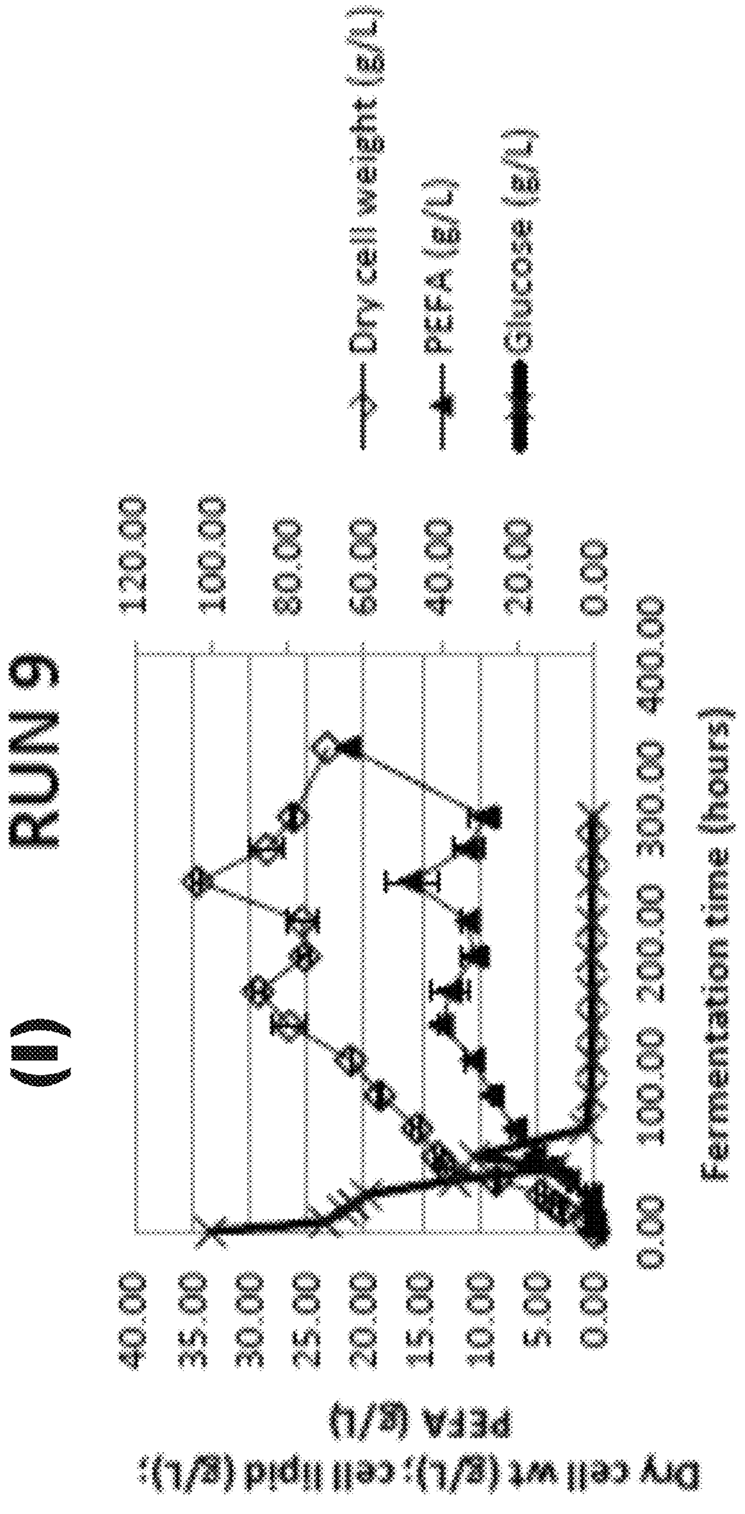

Yeast strains *Rhodosporidium* aff. *paludigenum* (UCDFST 81-84) and *Rhodosporidium babjevae* (UCDFST 04-877) were cultured in 4 L culture volume in batch fermentors. A total of 11 runs were done. The plots for each run are depicted in FIG. 14, and values at the time of harvest for cell dry weight, crude extracellular lipid and total microbial conversion are summarized in Table 7.

For all 11 runs, a seed culture was prepared by inoculating two 500 mL baffled flasks containing 95 mL of Medium A (50 g/L of either glucose or sucrose, depending on the run) with 5 mL cell suspension prepared as described in Example 1, and incubating it at room temperature for 24 hours at 200 RPM. The seed culture was transferred to a 7 L bioreactor containing 4 liters of Medium A with either glucose or sucrose with varying sugar concentrations depending on the run (see Table 7). Some of the runs had additional glucose dosings at 48 hours. Cultures were incubated for 7 days at 27 °C, 0.5 VVM (air) and agitation looped to the dissolved oxygen (DO) sensor to maintain a minimum of 40% DO during the entire fermentation. The starting pH of the media was 6.5 in all cases, and no acid or base were added during the course of the fermentation, because it was observed that adjusting the pH resulted in decreased PEFA production (results not shown). The pH values decreased during the course of the fermentation to final values of 6.3, 6.2 and 6.2. Temperature was kept constant at 27 °C. No antifoam was added during the course of fermentation, because when PEFA production began, the initial foam present on the surface of the cultures decreased until it disappeared completely.

Recovery of cells and secreted PEFA in bioreactors: Fifty mL samples were collected to monitor cell growth, glucose consumption and PEFA production. Samples were shaken thoroughly and divided into two sets of 10 mL aliquots. The first set was extracted twice with 40 mL of fresh ethyl acetate in duplicate, the solvent was removed using a vacuum speed concentrator (miVac Duo®, Genevac Inc., Stone Ridge, NY, USA), and the dry weight of the PEFA residue was recorded. The second set of 10 mL cultures were centrifuged in duplicate as described above and washed with DSW twice, and lyophilized as described above to obtain the dry weight. CMP was then determined by subtracting the PEFA output to the CMP values. Glucose concentration was determined via hydrophilic interaction chromatography-mass spectrometry (HILIC-MS). A volume of 10 μL of sample (sugar solution) was mixed with 990 μL acetonitrile/water (80:20, v/v) mixture containing $d_7$-glucose (Sigma-Aldrich, St. Louis, MO) at a concentration of 250 μg/mL. After brief vortexing and centrifugation (12,000 rpm for 2 min) 100 μL aliquot was transferred to a glass vial and submitted to HILIC-MS analysis. Quantification was conducted analyzing glucose and sucrose (Sigma-Aldrich) solutions (1-1500 μg/mL) in acetonitrile/water (80:20, v/v) mixture containing $d_7$-glucose (internal standard) at a concentration of 250 μg/mL. The system consisted of an Agilent 1290 Infinity LC system (Agilent Technologies, Santa Clara, CA) with a pump (G4220A), a column oven (G1316C), an autosampler (G4226A), and an Agilent 6550 QTOFMS. Diluted media samples were separated on an Acquity UPLC BEH Amide column (150×2.1 mm; 1.7 μm) coupled to an Acquity UPLC BEH Amide VanGuard pre-column (5×2.1 mm; 1.7 μm) (Waters). The column was maintained at 45 °C at a flow-rate of 0.4 mL/min. The mobile phases consisted of (A) water with ammonium formate (10 mM) and formic acid (0.125%) and (B) 95:5 (v/v) acetonitrile/water with ammonium formate (10 mM) and formic acid (0.125%). The separation was conducted under the following gradient: 0 min 100% (B); 0-2 min 100% (B); 2-7.7 min 70% (B); 7.7-9.5 min 40% (B); 9.5-10.25 min 30% (B); 10.25-12.75 min 100% (B); 12.75-17.75 min 100% (B). A sample volume of 3 μL was used for the injection. Sample temperature was maintained at 4 °C. The QTOF instrument was operated in electrospray ionization in negative mode with following parameters: mass range: m/z 50-1700; capillary voltage: −3 kV; nozzle voltage: −1 kV; gas temperature, 200 °C; drying gas (nitrogen), 14 L/min; nebulizer gas (nitrogen), 35 psi; sheath gas temperature, 350 °C; sheath gas flow (nitrogen), 11 L/min; acquisition rate: 2 spectra/s. For the data processing MassHunter Qualitative (B.05.00) and Quantitative (B.05.01) Analysis (Agilent) software programs were used.

Samples from run 6 and 7 were used to determine the physicochemical and surfactant properties of the PEFA mixtures, as described in Example 3.

The results are consistent with the conclusion that increasing amounts of product with increasing amount of carbon source. However, the efficiency with increasing amount of carbon source tends to drop in this particular condition.

Adjusting the glucose concentration and feed rate, and acration, can increase yields even more.

Example 4

Identifying the Physicochemical and Surfactant Properties of the PEFA Mixtures

The solubility, surface tension, surfactant particle size, emulsification index and size distribution under the microscope were analyzed for the crude PEFA mixtures obtained in runs 5 and 6. Sophorolipid (Sigma-Aldrich, catalog number 53735, 1',4"-Sophorolactone 6',6"-diacetate), one of the most well understood biosurfactants from yeast, was used as control.

Solubility: The water solubility of the PEFA was investigated by visual and turbidimetric detection (Transilluminator, FBTIV-816, Fisher Scientific). A blender (Ultra Turrax T25, IKA Labortechnik) was used to make a stock mixture of sophorolipids and water in a concentration of 1000 mg/L. The blending time was 1 minute and the blend mode was set to 11000/min. The mixtures of run 5 and run 6 were soluble to up to 10 mg/L, which was below the solubility of the control.

Surface Tension: Surface tensions were measured, using Wilhelmy plate method (Digital Tensiometer K10ST, KRÜSS) for different concentrations of PEFA in aqueous solution. The stabilization time was from 30 minutes in higher concentration to as long as 2 hours in lower concentration (below 2.5 mg/L). The final data was recorded when the measured surface tension became stable. The results are summarized in Table 8.

From a practical standpoint, a smaller dose of surfactant for both the mixture produced by strain *R. babjevae* UCDFST 04-877 and *R.* aff. *paludigenum* UCDFST 81-84was required to achieve the desired surfactant activity when compared to the control.

Surfactant Particle Size Analysis: Zetasizer (Malvern Instruments Inc. Westborough, MA) was used to measure the surfactant particle size in water by dynamic light scattering. The measurement angle was 90°. The temperature was set to be 25 °C. The refractive index was set to be 1.52. The results showed that both biosurfactants were able to create smaller particles than the control, as shown in Table 9. Smaller averages of diameters relate to a higher interfacial surface, which is a desired trait in surfactants.

Figure 15:
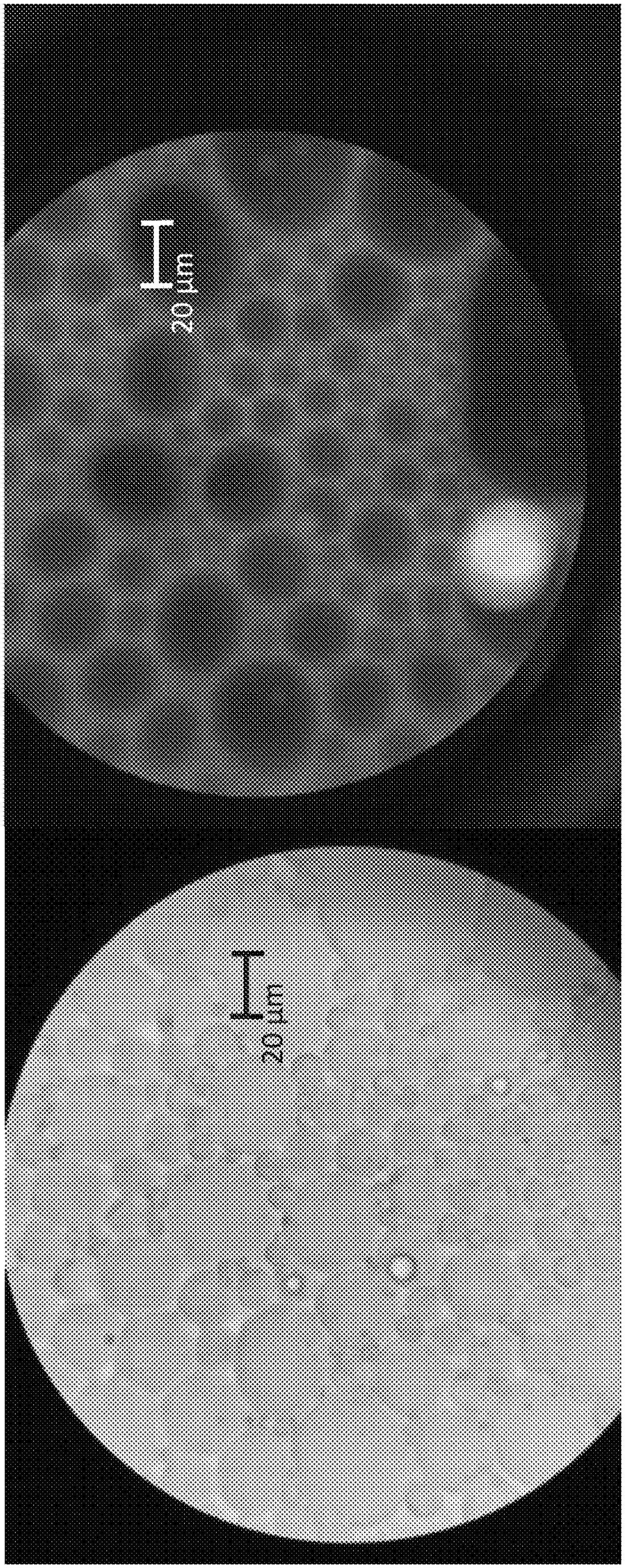
FIG. 15 illustrates a microscopic visualization using Brightfield mode and fluorescence mode at 100× magnification of the water in oil emulsion formed when 1 mL of octane is mixed with 1 mL of water and 5 mg of the mixture of PEFA produced by strain *Rhodotorula* aff. *paludigena* UCDFST 81-84, and mixed for 2 minutes using S8220 Deluxe mixer (EVANSTON, Illinois, 60201) in the mode of "FAST" at room temperature.

Size distribution under the microscope: Firstly, Nile Red was added in octane in the concentration of 0.05 mg/mL (0.005 wt %). The actual amount of dissolved Nile Red is much smaller than the added amount. Methylene Blue was added into the water in the concentration of 0.004 mg/mL (0.0004 wt %). Then 1 ml of dyed water and 1 ml of dyed octane were mixed in a 2-ml centrifuge tube. Then the tube is vortexed for 2 minutes using S8220 Deluxe mixer (EVANSTON, Illinois, 60201) in the mode of "FAST". Optical microscope (Carl Zeiss AG) was used for observation. The emulsions were observed immediately after they are prepared (within 30 minutes, see FIG. 15).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

TABLE 1

Yeast Species Previously Reported To Synthesize And Secrete Polyol Lipids: Polyol Esters of Fatty Acids (PEFA) or Liamocins

| Species | Strain | Publ. Year | Environmental source of the strain | Reference |
|---|---|---|---|---|
| Basidiomycota (PEFA) | | | | |
| *Rhodosporidiobolus azoricus* (previously identified as *Rhodotorula glutinis*) | CBS 4648 | 1964 | Leaf surface of Cacao plants, Ghana | Tulloch, et al., *Can J Chem* (1964) 42: 830-835 |
| *Rhodotorula glutinis* | 16A8 | 1964 | Flowers, Canada | |
| *Rhodotorula toruloides* (previously identified as *Rhodotorula glutinis*) | IIP-30 = ATCC 204091 | 1994 | Hydrocarbon contaminated soil, India | Johnson, et al., *Biotechnol Lett* (1992) 14: 487-490 |
| *Rhodotorula graminis* | 6CB | 1961 | Flowers, Canada | Tulloch, et al., Can J Chem (1964) 42: 830-835 |
| *Rhodotorula babjevae* (syn. *Rhodosporidium babjevae*) | UCDFST 04-877 | 2016 | Olive fly, California, USA | Cajka, *J Nat Prod* (2016) 79: 2580-2589 |
| Ascomycota (Liamocins) | | | | |
| *Aureobasidium* sp. | A-2 | 1994 | Natural sources | Kurosawa, et al., *Biosci Biotechnol Biochem* (1994) 58: 2057-2060 |
| *Aureobasidium* sp. | A-21 M | 1994 | Natural sources | |
| *Aureobasidium pullulans* (syn. *Pullularia pullulans*) | 272 | 1964 | Phyllosphere of tropical foliage, Java | Ruinen, et al., *Antonie Van Leeuwenhoek* (1964) 30: 377-384 |
| *Aureobasidium pullulans* | CU 39 = NRRL 58551 | 2009, 2011 | *Mimusops elengi* L. (Spanish cherry), Thailand | Manitchotpisit, et al., *Mycol Res* (2009) 113: 1107-1120; Manitchotpisit, et al., (2011) *Biotechnol Lett* 33: 1151-1157 |
| *Aureobasidium pullulans* | CU43 = NRRL 50380 | 2011, 2013 | Leaf of *Cassia fistula* L. (golden shower tree), Udonthani, Thailand | Manitchotpisit, et al., (2011) *Biotechnol Lett* 33: 1151-1157; Price, et al., *Carbohydr Res* 370: 24-32 |

CBS: Centraalbureau voor Schimmelcultures, The Netherlands;
ATCC: American Type Culture Collection, VA, USA;
NRRL: USDA-ARS Culture Collection, IL, USA

TABLE 2

Description of the yeast strains used for the present study.

| Strain species and Phaff collection ID | Synonym[a] | ID number in other collections | Source habitat | Genbank Accession numbers |
|---|---|---|---|---|
| Cystobasidium minutum UCDFST 68-280 | Rhodotorula minuta | CBS 319, ATCC 10658, NRRL Y-1589 | Air, Tokyo, Japan | KU609482, KU609540 |
| Hamamotoa singularis UCDFST 60-79 | Sporobolomyces singularis | CBS 5109 | *Tsuga heterophylla* (western hemlock), Siletz river, OR, USA | KU609483 |
| Occultifur externus UCDFST 68-934.2 | | | Exudate of *Acer* sp., BC, Canada | KU609481, KU609539 |
| Rhodosporidiobolus aff. lusitaniae UCDFST 06-583 | Rhodotorula aff. lusitaniae | | Olive fly, Davis, CA, USA | KU609443, KU609501 |
| Rhodosporidiobolus colostri UCDFST 05-609 | Rhodotorula colostri | | Olive *Olea europeae* flower, Winters, CA, USA | KU609442, KU609500 |
| Rhodosporidiobolus cf. fluvialis UCDFST 81-485.4 | Rhodosporidium cf. fluviale | | *Opuntia ficus-indica*, Tucson, AZ, USA | KU609434, KU609492 |
| Rhodosporidiobolus odoratus UCDFST 04-870 | Sporobolomyces odoratus | | Olive fly, Davis, CA, USA | KU609474, KU609532 |
| Rhodosporidiobolus odoratus UCDFST 09-1303 | Sporobolomyces odoratus | | Sunflower leaf, Davis, CA, USA | KU609473, KU609531 |
| Rhodosporidiobolus poonsookiae UCDFST 10-441 | Sporobolomyces poonsookiae | FORDACC 1642 | Leaf litter, Sulawesi, Indonesia | KU609475, KU609533 |
| Rhodosporidiobolus ruineniae UCDFST 10-1058 | Sporidiobolus ruineniae | FORDACC 552 | Leaf litter, Sulawesi, Indonesia | KU609462, KU609520 |
| Rhodosporidiobolus ruineniae UCDFST 10-1109 | Sporidiobolus ruineniae | FORDACC 540, InaCC 0476 | Leaf surface, Sulawesi, Indonesia | KU609463, KU609521 |
| Rhodosporidiobolus ruineniae UCDFST 12-776 | Sporidiobolus ruineniae | FORDACC 1885 | Soil, Sulawesi, Idonesia | KU609460, KU609518 |
| Rhodosporidiobolus ruineniae UCDFST 67-67[(T)] | Sporidiobolus ruineniae | | Leaves of *Malpighia coccigera*. Bogor, Indonesia | KU609461, KU609519 |
| Rhodosporidiobolus ruineniae UCDFST 78-84 | Sporidiobolus ruineniae | | Plant material, Panama | KX771208 KX771223 |
| Rhodotorula araucariae UCDFST 69-61[(T)] | | CBS 6031, ATCC 22078, NRRL Y-17376 | *Araucaria araucana* tree in Chile | KU609441, KU609499 |
| Rhodotorula babjevae UCDFST 04-830 | Rhodosporidium babjevae | | Male olive fly, Winters, CA, USA | KX771211, KX771226 |
| Rhodotorula babjevae UCDFST 04-877 | Rhodosporidium babjevae | | Olive fly, Davis, CA, USA | KU609429, KU609487 |
| Rhodotorula babjevae UCDFST 05-613 | Rhodosporidium babjevae | | Olive fly, Davis, CA, USA | KX771204, KX771219 |
| Rhodotorula babjevae UCDFST 05-736 | Rhodosporidium babjevae | | Female olive fly, Davis, CA, USA | KX771209, KX771224 |
| Rhodotorula babjevae UCDFST 05-775 | Rhodosporidium babjevae | | Dry sap of olive tree, Winters, CA, USA | KU609430, KU609488 |
| Rhodotorula babjevae UCDFST 06-542 | Rhodosporidium babjevae | | Olive-fly infested olive, Winters, CA, USA | KX771212, KX771227 |
| Rhodotorula babjevae UCDFST 67-102 | Rhodosporidium babjevae | | Sea water, Point Reyes, CA, USA | KX771203, KX771218 |
| Rhodotorula babjevae UCDFST 67-436 | Rhodosporidium babjevae | | Exudate of *Pterocarya rhoifolia*, Kaida, Kiso, Japan | KX771205, KX771220 |
| Rhodotorula babjevae UCDFST 67-458 | Rhodosporidium babjevae | | Exudate of *Betula ermani*, Mt. Fuji, Japan | KU609433, KU609491 |
| Rhodotorula babjevae UCDFST 67-478 | Rhodosporidium babjevae | | Exudate of *Prunus sargentii*, Jatani, Yamagata, Japan | KX771210, KX771225 |
| Rhodotorula babjevae UCDFST 67-506 | Rhodosporidium babjevae | | Exudate of *Ulmus davidiana* var. *japonica*. Hibara (Fukushima), Japan | KX771206, KX771221 |
| Rhodotorula babjevae UCDFST 68-916.1 | Rhodosporidium babjevae | | Insect frass in *Alnus* sp. (alder) tree, BC, Canada | KU609431, KU609489 |
| Rhodotorula dairenensis UCDFST 68-257 | | CBS 347, NRRL Y-1596 | Air, Tokyo, Japan | KU609444, KU609502 |
| Rhodotorula dairenensis UCDFST 68-275[(T)] | | CBS 2826, ATCC 32768 | Pasture grass, New Zealand | KU609448, KU609506 |
| Rhodotorula diobovata UCDFST 08-225 | Rhodosporidium diobovatum | CBS 6085 | Sea water, FL, USA. | KU609432, KU609490 |
| Rhodotorula glutinis UCDFST 50-309[(T)] | | CBS 20, ATCC 2527 | Atmosphere, Japan | KX771201, KX771216 |
| Rhodotorula graminis UCDFST 05-503 | | | Olive fly, Davis, CA, USA | KU609446, KU609504 |
| Rhodotorula kratochvilovae UCDFST 05-632 | Rhodosporidium kratochvilovae | | *Chysoperla careae* (green lacewing), Winters, CA, USA | KU609435, KU609493 |
| Rhodotorula mucilaginosa UCDFST 05-218 | | | *Drosophila melanogaster* fly in apple. Davis, CA, USA. | KX771215, KX771230 |
| Rhodotorula mucilaginosa UCDFST 10-221 | | | *Anisomorpha buprestoides* (2-stripe stick insect), Davis, CA, USA | KX771214, KX771229 |
| Rhodotorula mucilaginosa UCDFST 13-478 | | | Forest ecosystem: Rawa Aopa, Sulawesi, Indonesia | KU609450, KU609508 |

TABLE 2-continued

Description of the yeast strains used for the present study.

| Strain species and Phaff collection ID | Synonym[a] | ID number in other collections | Source habitat | Genbank Accession numbers |
|---|---|---|---|---|
| Rhodotorula mucilaginosa UCDFST 67-64 | | | Unknown. | KX771213, KX771228 |
| Rhodotorula mucilaginosa UCDFST 68-329[(T)] | | CBS 482, ATCC 24216, NRRL Y-6683 | Smut-infected leaves, France | KU609449, KU609507 |
| Rhodotorula mucilaginosa UCDFST 68-854.2 | | CBS 6462 | Exudate of *Populus tremuloides*. BC, Canada | KX771207, KX771222 |
| Rhodotorula mucilaginosa UCDFST 78-54 | | | Lake water, Wisconsin, USA | KU609445, KU609503 |
| Rhodotorula aff. paludigena UCDFST 81-84 | Rhodosporidium aff. Paludigenum | | *Opuntia* sp., Bahamas | KU609438, KU609496 |
| Rhodotorula paludigena UCDFST 09-163 | Rhodosporidium paludigenum | CBS 3044 | Leaf of *Desmodium repens*, Netherlands | KU609436, KU609494 |
| Rhodotorula paludigena UCDFST 81-492 | Rhodosporidium paludigenum | | *Opuntia ficus-indica* cactus; AZ, USA | KX771202, KX771217 |
| Rhodotorula paludigena UCDFST 82-646.2 | Rhodosporidium paludigenum | | *Melocactus intortus*, Prickly Pear Island, British Virgin Islands | KU609437, KU609495 |
| Rhodotorula sphaerocarpa UCDFST 68-43 | Rhodosporidium sphaerocarpum | | Auxotrophic mutant of strain UCDFST 48-23 | KU609439, KU609497 |
| Rhodotorula toruloides UCDFST 67-52 [(NT)] | Rhodosporidium toruloides | CBS 349, NRRL Y-1588 | Soil, Tokyo, Japan | KU609440, KU609498 |
| Sporidiobolus pararoseus UCDFST 09-1305 | | | Sunflower leaf surface, Davis, CA, USA | KU609457, KU609515 |
| Sporidiobolus pararoseus UCDFST 44-17 | | | Hemp rope, Panama | KU609454, KU609512 |
| Sporidiobolus pararoseus UCDFST 67-552 | | | Exudate of Monarch birch *Betula maximowicziana*, Tomakomai, Japan | KU609453, KU609511 |
| Sporobolomyces bannaensis UCDFST 10-421 | | FORDACC 1727, InaCC 0478 | Leaf surface, Sulawesi, Indonesia | KU609458, KU609516 |
| Sporobolomyces bannaensis UCDFST 10-451 | | FORDACC 4481, InaCC 0521 | Leaf surface, Sulawesi, Indonesia | KU609459, KU609517 |
| Sporobolomyces bannaensis UCDFST 10-453 | | FORDACC 1700, InaCC 0523 | Leaf surface, Sulawesi, Indonesia | KU609468, KU609526 |
| Sporobolomyces bannaensis UCDFST 11-470 | | FORDACC 937, InaCC 0521 | Leaf surface, Sulawesi, Indonesia | KU609469, KU609527 |
| Sporobolomyces aff. beijingensis UCDFST 11-1143 | | | Cherry, Corvallis, OR, USA | KU609477, KU609535 |
| Sporobolomyces carnicolor UCDFST 03-573 | | | *Rubiaceae* fruit, Nicaragua | KU609471, KU609529 |
| Sporobolomyces carnicolor UCDFST 68-346 | | CBS 2637 | Air, Delft, the Netherlands | KU609456, KU609514 |
| Sporobolomyces carnicolor UCDFST 68-348 | | CBS 4215 | Unknown, Nagano, Japan | KU609472, KU609530 |
| Sporobolomyces johnsonii UCDFST 67-65 | Sporidiobolus johnsonii | | Tropical foliage, Netherlands | KU609451, KU609509 |
| Sporobolomyces johnsonii UCDFST 68-29 | Sporidiobolus johnsonii | CBS 5470, ATCC 10765, NRRL Y-17303 | Infected Raspberry plant *Rubus idaeus*, WA, USA | KU609452, KU609510 |
| Sporobolomyces metaroseus UCDFST 05-893 | | | Olive fly-infested olive, Ventura, CA, USA | KU609476, KU609534 |
| Sporobolomyces salmonicolor UCDFST 10-159 | Sporidiobolus salmonicolor | | Soil in the permafrost area, Siberia, | KU609447, KU609505 |
| Sporobolomyces salmonicolor UCDFST 44-3 | Sporidiobolus salmonicolor | | Deteriorated quartermaster items, FL, USA | KU609465, KU609523 |
| Sporobolomyces salmonicolor UCDFST 67-1029 | Sporidiobolus salmonicolor | | Elm exudate in soil, Davis, CA, USA | KU609464, KU609522 |
| Sporobolomyces salmonicolor UCDFST 72-182 | Sporidiobolus salmonicolor | | Tree, Kyoto, Japan | KU609467, KU609525 |
| Trigonosporomyces aff. hylophilus UCDFST 79-1005 | Rhodotorula aff. hylophilus | | Substrate unknown, Davis, CA | KU609478, KU609536 |

UCDFST: Phaff Yeast Culture Collection, University of California Davis.
FORDACC: Ministry of Forestry Culture Collection, Bogor, Indonesia.
InaCC: Indonesian National Culture Collection, Cibinong, Indonesia.
CBS: Centraalbureau voor Schimmelcultures, Utrecht, The Netherlands.
NRRL: USDA-ARS Culture Collection, Peoria, IL, USA.
ATCC: American Type Culture Collection, Maryland, USA.
[(T)]Type strain.
[(NT)] neotype strain.
See, [53] for information on recent taxonomic changes.

TABLE 3

Yeast strains that secreted ≥1 g $L^{-1}$ net PEFA

| Strain species and Phaff collection ID | ID number in other collections | Source habitat | Dry Cell weight (g $L^{-1}$) | Crude extract containing PEFA (g $L^{-1}$) | Estimated PEFA purity (%) | Net PEFA produced (g $L^{-1}$) |
|---|---|---|---|---|---|---|
| *R. babjevae* UCDFST 04-830 | | Male olive fly, Winters, CA, USA | 13 | 8.5 | 99.9 | 8.5 |
| *R. babjevae* UCDFST 04-877 | | Olive fly, Davis, CA, USA | 14.9 | 8.7 | 00.1 | 8.6 |
| *R. babjevae* UCDFST 05-613 | | Olive tree, Davis, CA, USA | 13.6 | 4.3 | 99.8 | 4.3 |
| *R. babjevae* UCDFST 05-736 | | Female olive fly, Davis, CA, USA | 12.5 | 5.5 | 99.9 | 5.5 |
| *R. babjevae* UCDFST 05-775 | | Dry sap of olive tree, Winters, CA, USA | 14.1 | 6.5 | 88.4 | 6.4 |
| *R. babjevae* UCDFST 06-542 | | Olive-fly infested olive, Winters, CA, USA | 13 | 5.1 | 99.9 | 5.1 |
| *R. babjevae* UCDFST 07-102 | | Sea water, Point Reyes, CA, USA | 11.4 | 5.8 | 99.9 | 5.8 |
| *R. babjevae* UCDFST 07-436 | | Exudate of *Pterocarya rhoifolia*, Kaida, Kiso, Japan | 13.3 | 4 | 99.8 | 4 |
| *R. babjevae* UCDFST 07-458 | | Exudate of *Betula emani*, Mt. Fuji, Japan | 13.4 | 2.7 | 92.5 | 2.5 |
| *R. babjevae* UCDFST 07-478 | | Exudate of *Prunus sorgentii*, Jatani, Yamagata, Japan | 13.5 | 4.6 | 99.8 | 4.6 |
| *R. babjevae* UCDFST 07-506 | | Exudate of *Ulmus davidana* var. japorica Hibara (Fukushima), Japan | 12.6 | 5.1 | 99.8 | 5.1 |
| *R. babjevae* UCDFST 68-916.1 | | Insect frass in *Afnus* sp. (alder) tree, BC, Canada | 13.9 | 1.1 | 97.2 | 1.1 |
| *R. dibovata* UCDFST 08-225 | CBS 6085 | Sea water, FL, USA. | 9.6 | 2.1 | 96.9 | 2 |
| *R. graminis* UCDFST 05-503 | | Olive fly, Davis, CA, USA | 13.9 | 3.8 | 99.6 | 3.8 |
| *R. kratochvilovae* UCDFST 05-632 | | *Chysoperia careae* (green lacewing), Winters, CA, USA | 15.1 | 3.1 | 98.4 | 3.1 |
| *R. aff. paludigena* UCDFST 81-84 | | *Opuntia* sp., Bahamas | 11.9 | 12.7 | 97.4 | 12.4 |
| *R. paludigena* UCDFST 09-163 | CBS 3044 | Leaf of *Desmodium repens*, Netherlands | 13.7 | 2.2 | 96.8 | 2.1 |
| *R. paludigena* UCDFST 81-492 | | *Opuntia ficus*-indice cactus; AZ, USA | 11.1 | 11.8 | 99.8 | 11.7 |
| *R. paludigena* UCDFST 82-546.2 | | *Melocactus intortus,* Prickly Pear Island, British Virgin Islands | 14.9 | 3.1 | 98.5 | 3.1 |

The yeast strains were sourced from the Phaff Yeast Culture Collection, University of California Davis. Abbreviation "cf." (Latin "confer"): the species is quite similar to the indicated known species. Abbreviation "*aff.*" (Latin "*affinis*"): the species is significantly different from the indicated known species, and is probably a novel species based on ribosomal sequence analysis. Strains identified as "T" are the type strain of the species, "NT" is the neotype strain. The first two digits of the ID number are the year the strain was deposited in the Phaff collection.

New PEFA secreters are in bold.

N/A: Not applicable.

TABLE 4

Chemical formula, molecular weight, retention time (tR), description, and systematic name of the 19 PEFA detected in this study

| PEFA no. | Chemical formula | m/z $[M + NH_4]^+$ | $^{t}$R (min) | Description |
|---|---|---|---|---|
| PEFA1 | $C_{27}H_{46}O_{11}$ | 564.3384 | 2.05 | Acetylated C12:0 3-hydroxy fatty acid esterified to D-arabitol with 3 acetylations |
| PEFA 2 | $C_{30}H_{50}O_{13}$ | 636.3590 | 2.10 | Acetylated C14:0 3-hydroxy fatty acid esterified to D-mannitol with 4 acetylations |
| PEFA 3 | $C_{28}H_{50}O_{11}$ | 580.3697 | 2.29 | Acetylated C16:0 3-hydroxy fatty acid esterified to D-mannitol with 2 acetylations |
| PEFA 4 | $C_{27}H_{48}O_{10}$ | 550.3591 | 2.45 | Acetylated C16:0 3-hydroxy fatty acid esterified to D-arabitol with 2 acetylations |
| PEFA 5 | $C_{29}H_{48}O_{12}$ | 606.3490 | 2.49 | Acetylated C14:0 3-hydroxy fatty acid esterified to D-arabitol with 4 acetylations |
| PEFA 6 | $C_{32}H_{52}O_{14}$ | 678.3695 | 2.52 | Acetylated C14:0 3-hydroxy fatty acid esterified to D-mannitol with 5 acetylations |
| PEFA 7 | $C_{30}H_{52}O_{12}$ | 622.3803 | 2.61 | Acetylated C16:0 3-hydroxy fatty acid esterified to D-mannitol with 3 acetylations |
| PEFA 8 | $C_{29}H_{50}O_{11}$ | 592.3697 | 2.86 | Acetylated C16:0 3-hydroxy fatty acid esterified to D-arabitol with 3 acetylations |
| PEFA 9 | $C_{32}H_{54}O_{13}$ | 664.3903 | 2.87 | Acetylated C16:0 3-hydroxy fatty acid esterified to D-mannitol with 4 acetylations |
| PEFA 10 | $C_{30}H_{54}O_{11}$ | 608.4004 | 2.99 | Acetylated C18:0 3-hydroxy fatty acid esterified to D-mannitol with 2 acetylations |
| PEFA 11 | $C_{34}H_{56}O_{14}$ | 706.4008 | 3.10 | Acetylated C16:0 3-hydroxy fatty acid esterified to D-mannitol with 5 acetylations |
| PEFA 12 | $C_{31}H_{52}O_{12}$ | 634.3803 | 3.11 | Acetylated C16:0 3-hydroxy fatty acid esterified to D-arabitol with 4 acetylations |
| PEFA 13 | $C_{32}H_{56}O_{12}$ | 650.4110 | 3.12 | Acetylated C18:0 3-hydroxy fatty acid esterified to D-mannitol with 3 acetylations |
| PEFA 14 | $C_{34}H_{58}O_{13}$ | 692.4216 | 3.31 | Acetylated C18:0 3-hydroxy fatty acid esterified to D-mannitol with 4 acetylations |
| PEFA 15 | $C_{31}H_{54}O_{11}$ | 620.4010 | 3.29 | Acetylated C18:0 3-hydroxy fatty acid esterified to D-arabitol with 3 acetylations |

TABLE 4-continued

Chemical formula, molecular weight, retention time (tR), description, and systematic name of the 19 PEFA detected in this study

| PEFA no. | Chemical formula | m/z $[M + NH_4]^+$ | $^tR$ (min) | Description |
|---|---|---|---|---|
| PEFA 16 | $C_{36}H_{60}O_{14}$ | 734.4321 | 3.49 | Acetylated C18:0 3-hydroxy fatty acid esterified to D-mannitol with 5 acetylations |
| PEFA 17 | $C_{33}H_{56}O_{12}$ | 662.4116 | 3.47 | Acetylated C18:0 3-hydroxy fatty acid esterified to D-arabitol with 4 acetylations |
| PEFA 18 | $C_{34}H_{60}O_{12}$ | 678.4423 | 3.52 | Acetylated C20:0 3-hydroxy fatty acid esterified to D-mannitol with 3 acetylations |
| PEFA 19 | $C_{36}H_{62}O_{13}$ | 720.4529 | 3.69 | Acetylated C20:0 3-hydroxy fatty acid esterified to D-mannitol with 4 acetylations |

PEFA were detected as $[M + NH4]^+$ and $[M + Na]^+$ adducts using RPLC-ESI(+)-QTOFMS

TABLE 5

All polyol esters of fatty acids (PEFA) detected, as a percent of total PEFA produced by those yeast strains whose PEFA crude extracts gave signals above the detection level.

| Strain species and Phaff collection ID | PEFA 1 | PEFA 2 | PEFA 3 | PEFA 4 | PEFA 5 | PEFA 6 | PEFA 7 | PEFA 8 | PEFA 9 | PEFA 10 | PEFA 11 | PEFA 12 | PEFA 13 | PEFA 14 | PEFA 15 | PEFA 16 | PEFA 17 | PEFA 18 | PEFA 19 | Others (N/I) |
|---|---|---|---|---|---|---|---|---|---|---|---|---|---|---|---|---|---|---|---|---|
| *Cystobasidium minutum* UCDFST 68-280 | 0.4 | 0.1 | 0.1 | 0.2 | 1.1 | 0.1 | 0.4 | 27.7 | 3.4 | 0.6 | 0.6 | 28.0 | 1.6 | 3.7 | 13.0 | 0.5 | 6.2 | 4.0 | 1.6 | 4.7 |
| *Occultifur externus* UCDFST 68-934.2 | 0.4 | 0.3 | 0.3 | 0.6 | 1.1 | 0.2 | 0.5 | 35.6 | 15.2 | 0.5 | 0.8 | 19.2 | 1.3 | 6.3 | 8.7 | 0.6 | 3.3 | 0.2 | 0.5 | 3.3 |
| *Rhodosporidiobolus aff. lusitaniae* UCDFST 06-583 | 0.2 | 0.4 | 0.6 | 0.8 | 0.8 | 0.4 | 2.6 | 7.3 | 7.8 | 0.9 | 4.0 | 25.3 | 5.4 | 11.3 | 7.0 | 2.1 | 11.9 | 1.3 | 0.7 | 6.0 |
| *Rhodosporidiobolus odoratus* UCDFST 09-1303 | 0.6 | 0.7 | 1.3 | 1.5 | 1.6 | 0.0 | 3.6 | 7.2 | 6.7 | 1.0 | 3.3 | 17.2 | 5.8 | 10.2 | 6.6 | 2.2 | 6.4 | 2.3 | 1.9 | 13.8 |
| *Rhodosporidiobolus ruineniae* UCDFST 10-1058 | 0.3 | 0.4 | 0.8 | 1.2 | 0.4 | 0.2 | 4.3 | 8.0 | 9.2 | 1.4 | 2.5 | 13.4 | 10.1 | 18.6 | 8.2 | 2.6 | 13.0 | 0.8 | 0.4 | 2.4 |
| *Rhodosporidiobolus ruineniae* UCDFST 12-776 | 1.2 | 0.9 | 1.0 | 1.1 | 1.0 | 0.7 | 1.5 | 4.3 | 6.5 | 0.9 | 3.0 | 16.7 | 3.5 | 13.3 | 10.3 | 1.7 | 12.5 | 1.9 | 1.2 | 10.4 |
| *Rhodosporidiobolus ruineniae* UCDFST 67-67 (T) | 0.1 | 0.1 | 0.2 | 0.6 | 0.6 | 0.2 | 1.4 | 7.6 | 3.2 | 0.5 | 4.3 | 29.2 | 5.7 | 5.6 | 15.0 | 1.9 | 21.0 | 0.3 | 0.2 | 1.5 |
| *Rhodosporidiobolus ruineniae* UCDFST 78-84 | 1.0 | 0.5 | 1.8 | 1.4 | 2.0 | 0.4 | 0.7 | 19.9 | 12.4 | 0.7 | 1.8 | 14.2 | 2.9 | 8.0 | 9.2 | 1.0 | 5.4 | 1.2 | 1.0 | 8.2 |
| *Rhodotorula babjevae* UCDFST 04-830 | 0.2 | 0.1 | 0.3 | 1.5 | 1.2 | 0.2 | 12.4 | 13.6 | 10.0 | 0.2 | 2.9 | 18.8 | 6.9 | 9.3 | 8.2 | 0.9 | 12.9 | 0.0 | 0.0 | 0.0 |
| *Rhodotorula babjevae* UCDFST 04-877 | 0.1 | 0.3 | 0.2 | 0.4 | 1.1 | 0.2 | 1.6 | 4.2 | 12.8 | 0.2 | 3.9 | 31.4 | 3.5 | 12.2 | 5.4 | 2.1 | 19.9 | 0.1 | 0.3 | 0.1 |
| *Rhodotorula babjevae* UCDFST 05-613 | 0.0 | 0.3 | 0.0 | 0.1 | 1.0 | 0.1 | 3.4 | 5.5 | 17.7 | 0.1 | 3.1 | 26.9 | 4.3 | 12.7 | 5.6 | 1.4 | 17.4 | 0.0 | 0.1 | 0.0 |
| *Rhodotorula babjevae* UCDFST 05-736 | 0.05 | 0.46 | 0.05 | 0.23 | 1.18 | 0.16 | 3.38 | 8.39 | 21.71 | 0.07 | 3.07 | 22.11 | 2.99 | 15.31 | 5.78 | 1.19 | 13.60 | 0.01 | 0.02 | 0.02 |
| *Rhodotorula babjevae* UCDFST 05-775 | 0.2 | 0.4 | 0.8 | 1.2 | 1.7 | 0.2 | 4.2 | 8.1 | 12.0 | 0.8 | 3.7 | 22.2 | 6.6 | 13.3 | 7.9 | 1.9 | 14.1 | 0.1 | 0.2 | 0.0 |
| *Rhodotorula babjevae* UCDFST 06-542 | 0.1 | 0.2 | 0.3 | 0.4 | 0.9 | 0.2 | 10.2 | 7.6 | 16.2 | 0.3 | 3.1 | 19.0 | 8.6 | 13.7 | 6.2 | 1.1 | 11.6 | 0.0 | 0.0 | 0.0 |
| *Rhodotorula babjevae* UCDFST 67-102 | 0.1 | 0.1 | 0.1 | 0.2 | 0.8 | 0.4 | 11.5 | 6.6 | 10.7 | 0.1 | 5.6 | 20.6 | 9.6 | 11.7 | 5.6 | 2.0 | 13.9 | 0.0 | 0.1 | 0.0 |

TABLE 5-continued

All polyol esters of fatty acids (PEFA) detected, as a percent of total PEFA produced by those yeast strains whose PEFA crude extracts gave signals above the detection level.

| Strain species and Phaff collection ID | PEFA 1 | PEFA 2 | PEFA 3 | PEFA 4 | PEFA 5 | PEFA 6 | PEFA 7 | PEFA 8 | PEFA 9 | PEFA 10 | PEFA 11 | PEFA 12 | PEFA 13 | PEFA 14 | PEFA 15 | PEFA 16 | PEFA 17 | PEFA 18 | PEFA 19 | Others (N/I) |
|---|---|---|---|---|---|---|---|---|---|---|---|---|---|---|---|---|---|---|---|---|
| *Rhodotorula babjevae* UCDFST 67-436 | 0.0 | 0.2 | 0.0 | 0.0 | 0.7 | 0.3 | 6.5 | 3.4 | 16.0 | 0.1 | 5.7 | 26.2 | 6.1 | 12.7 | 4.4 | 2.0 | 15.3 | 0.0 | 0.1 | 0.0 |
| *Rhodotorula babjevae* UCDFST 67-458 | 0.0 | 0.2 | 0.0 | 0.0 | 0.8 | 0.3 | 2.7 | 3.4 | 19.2 | 0.1 | 7.3 | 22.2 | 4.7 | 17.5 | 4.6 | 2.6 | 13.8 | 0.0 | 0.4 | 0.0 |
| *Rhodotorula babjevae* UCDFST 67-478 | 0.1 | 0.1 | 0.2 | 0.8 | 1.1 | 0.2 | 11.7 | 11.3 | 7.0 | 0.2 | 3.4 | 24.5 | 9.8 | 5.7 | 8.5 | 1.1 | 14.1 | 0.0 | 0.0 | 0.0 |
| *Rhodotorula babjevae* UCDFST 67-506 | 0.1 | 0.1 | 0.4 | 1.5 | 0.6 | 0.1 | 10.2 | 13.0 | 9.8 | 0.3 | 2.1 | 20.3 | 8.0 | 11.0 | 9.0 | 0.8 | 12.5 | 0.0 | 0.0 | 0.0 |
| *Rhodotorula babjevae* UCDFST 68-916.1 | 0.1 | 0.0 | 2.4 | 1.3 | 0.1 | 0.2 | 3.3 | 7.2 | 1.9 | 2.3 | 11.2 | 7.9 | 16.9 | 5.3 | 13.2 | 7.2 | 18.7 | 0.3 | 0.1 | 0.2 |
| *Rhodotorula dairenensis* UCDFST 68-257 | 0.0 | 0.0 | 0.0 | 0.0 | 0.0 | 0.0 | 0.1 | 0.2 | 2.9 | 0.1 | 12.4 | 23.1 | 0.4 | 6.1 | 1.7 | 9.1 | 43.8 | 0.0 | 0.0 | 0.1 |
| *Rhodotorula diobovata* UCDFST 08-225 | 0.0 | 0.0 | 0.0 | 0.0 | 0.0 | 0.2 | 0.1 | 0.4 | 0.8 | 0.1 | 30.7 | 7.8 | 1.2 | 16.9 | 0.9 | 22.3 | 18.4 | 0.0 | 0.1 | 0.0 |
| *Rhodotorula glutinis* UCDFST 05-503 | 0.0 | 0.2 | 0.2 | 0.1 | 0.7 | 0.7 | 9.3 | 4.3 | 15.3 | 0.2 | 10.5 | 15.2 | 9.4 | 14.0 | 4.2 | 4.5 | 10.5 | 0.0 | 0.0 | 0.0 |
| *Rhodotorula glutinis* UCDFST 50-309 (T) | 0.0 | 0.1 | 0.1 | 0.1 | 0.2 | 0.5 | 0.7 | 1.1 | 4.9 | 0.2 | 36.1 | 11.8 | 3.6 | 13.2 | 2.9 | 15.4 | 8.2 | 0.1 | 0.4 | 0.2 |
| *Rhodotorula dairenensis* UCDFST 68-275 (T) | 0.5 | 1.1 | 0.9 | 1.4 | 0.6 | 0.5 | 3.4 | 3.3 | 10.2 | 0.9 | 3.4 | 14.5 | 5.9 | 14.3 | 6.0 | 2.1 | 8.4 | 2.6 | 1.9 | 10.1 |
| *Rhodotorula kratochvilovae* UCDFST 05-632 | 0.1 | 0.0 | 0.0 | 0.5 | 5.6 | 3.5 | 0.8 | 10.1 | 8.1 | 0.2 | 11.5 | 11.0 | 2.4 | 12.4 | 10.1 | 8.9 | 13.1 | 0.2 | 0.4 | 0.0 |
| *Rhodotorula mucilaginosa* UCDFST 05-218 | 1.5 | 1.1 | 1.0 | 2.0 | 3.1 | 0.8 | 1.5 | 13.3 | 3.2 | 1.1 | 1.9 | 35.8 | 1.1 | 1.4 | 4.7 | 0.9 | 7.9 | 1.3 | 0.9 | 8.1 |
| *Rhodotorula mucilaginosa* UCDFST 10-221 | 0.7 | 0.2 | 0.7 | 1.8 | 2.7 | 0.6 | 1.2 | 16.9 | 5.8 | 0.3 | 2.3 | 32.5 | 2.4 | 3.8 | 8.0 | 1.3 | 8.2 | 0.7 | 0.3 | 5.9 |
| *Rhodotorula mucilaginosa* UCDFST 67-64 | 1.1 | 0.7 | 1.1 | 1.1 | 1.3 | 0.7 | 1.0 | 18.4 | 9.6 | 1.0 | 2.2 | 15.9 | 2.4 | 5.5 | 9.7 | 1.4 | 7.0 | 0.4 | 1.1 | 11.0 |
| *Rhodotorula mucilaginosa* UCDFST 68-854.2 | 0.8 | 0.6 | 1.1 | 0.9 | 1.2 | 0.3 | 1.5 | 29.5 | 23.1 | 0.5 | 1.4 | 16.0 | 2.1 | 4.3 | 7.3 | 0.9 | 3.9 | 0.2 | 0.2 | 2.1 |
| *Rhodotorula aff. paludigena* UCDFST 81-84 | 1.9 | 0.0 | 0.2 | 1.0 | 6.0 | 0.0 | 0.5 | 33.3 | 0.6 | 0.1 | 0.0 | 34.4 | 0.2 | 0.1 | 15.0 | 0.0 | 5.8 | 0.0 | 0.0 | 0.0 |

TABLE 5-continued

All polyol esters of fatty acids (PEFA) detected, as a percent of total PEFA produced by those yeast strains whose PEFA crude extracts gave signals above the detection level.

| Strain species and Phaff collection ID | PEFA 1 | PEFA 2 | PEFA 3 | PEFA 4 | PEFA 5 | PEFA 6 | PEFA 7 | PEFA 8 | PEFA 9 | PEFA 10 | PEFA 11 | PEFA 12 | PEFA 13 | PEFA 14 | PEFA 15 | PEFA 16 | PEFA 17 | PEFA 18 | PEFA 19 | Others (N/I) |
|---|---|---|---|---|---|---|---|---|---|---|---|---|---|---|---|---|---|---|---|---|
| *Rhodotorula paludigena* UCDFST 09-163 | 0.1 | 0.4 | 0.1 | 0.3 | 1.8 | 0.1 | 2.1 | 6.2 | 16.4 | 0.2 | 1.5 | 47.7 | 2.4 | 6.9 | 5.7 | 0.2 | 7.4 | 0.0 | 0.1 | 0.1 |

TABLE 6

Identified Extracellular Lipids (Polyol Esters of Fatty Acids) Secreted by *Rhodotorula babjevae* UCDFST 04-877

| peak number[a] | $t_R$ (min) | m/z $[M + NH_4]_+$ | elemental composition | acetylated (R)-3-hydroxy fatty acid | D-polyol | degree of acetylation of polyol |
|---|---|---|---|---|---|---|
| 1 | 2.43 | 606.349 | C29H48O12 | C14:0 | arabitol | 4 |
| 2 | 2.48 | 622.3803 | C30H52O12 | C16:0 | mannitol | 3 |
| 3 | 2.8 | 592.3697 | C29H50O11 | C16:0 | arabitol | 3 |
| 4 | 2.87 | 664.3908 | C32H54O13 | C16:0 | mannitol | 4 |
| 5 | 3.07 | 634.3803 | C31H52O12 | C16:0 | arabitol | 4 |
| 6 | 3.1 | 706.4014 | C34H56O14 | C16:0 | mannitol | 5 |
| 7 | 3.12 | 650.4116 | C32H56O12 | C18:0 | mannitol | 3 |
| 8 | 3.27 | 620.401 | C31H54O11 | C18:0 | arabitol | 3 |
| 9 | 3.29 | 692.4221 | C34H58O13 | C18:0 | mannitol | 4 |
| 10 | 3.44 | 662.4116 | C33H56O12 | C18:0 | arabitol | 4 |
| 11 | 3.46 | 734.4327 | C36H60O14 | C18:0 | mannitol | 5 |

TABLE 7

| Run number | Yeast Strain | UCDFST Strain ID | Type of carbon source used | Amount and Feeding Strategy | Dry Cell weight (g/L) | Crude extracellular lipid (g/L) | Total Microbial Conversion (g/L) |
|---|---|---|---|---|---|---|---|
| 1 | *R. babjevae* | 04-877 | Glucose | 50 g/L initial | 16.59 | 3.98 | 20.6 (41.1% conversion) |
| 2 | *R. aff. paludigenum* | 81-84 | Glucose | 50 g/L initial | 14.39 | 7.69 | 22.1 (44.16% conversion) |
| 3 | *R. aff. paludigenum* | 81-84 | Glucose | 100 g/L initial 50 g/L at 48 hours | 22.71 | 15.22 | 37.9 (25.28% conversion) |
| 4 | *R. babjevae* | 04-877 | Glucose | 100 g/L initial, 50 g/L at 48 hours | 32.77 | 7.32 | 40.1 (26.73% conversion) |
| 5 | *R. babjevae* | 04-877 | Glucose | 100 g/L initial | 29.22 | 8.55 | 37.8 (37.77% conversion) |
| 6 | *R. aff. paludigenum* | 81-84 | Glucose | 100 g/L initial | 21.87 | 14.48 | 36.4 (36.35% conversion) |
| 7 | *R. aff. paludigenum* | 81-84 | Sucrose | 50 g/L initial | 16.66 | 9.53 | 26.2 (52.38% conversion) |
| 8 | *R. aff. paludigenum* | 81-84 | Sucrose | 100 g/L initial | 28.84 | 19.44 | 48.3 (48.28% conversion) |
| 9 | *R. aff. paludigenum* | 81-84 | Sucrose | 150 g/L initial, 50 g/L at 48 hours, | 23.24 | 21.48 | 44.7 (22.36% conversion) |
| 10 | *R. paludigena* | 81-492 | Glucose | 100 g/L initial | 18.6 | 17.5 | 36.1 (36.1% conversion) |
| 11 | *R. aff. paludigena* | 81-84 | Glycerol | 100 g/L initial | 20.3 | 18.7 | 39.0 (39.0% conversion) |

TABLE 8

| Surfactants | Minimum surface tension (mN/m) | Critical Micelle Concen-tration (mg/L) | Slope of linear part for surface tension line (mN/m) | Surface excess concen-tration (mol/m²) | Average area occupied by each molecule (Å²/molecule) |
|---|---|---|---|---|---|
| R. babjevae UCDFST 04-877 | 30.4 | 1.5 | −11.14 | $4.5 \times 10^{-6}$ | 35.7 |
| R. aff. paludigenum UCDFST 81-84 | 33.4 | 1.3 | −31.94 | $1.29 \times 10^{-5}$ | 12.5 |
| Sophorolipid | 36.8 | 15.2 | −11.14 | $2.93 \times 10^{-6}$ | 54.7 |

TABLE 9

| Surfactants | Z-Average of diameter (nm) |
|---|---|
| R. babjevae UCDFST 04-877 | 298.2 |
| R. aff. paludigenum UCDFST 81-84 | 491.9 |
| Commercial sophorolipid | 749.2 |

What is claimed is:

1. A method of producing one or more polyol lipids, comprising culturing a population of basidiomycetous yeast cells in a yeast cell culture comprising:

one or more hydrophilic carbon sources;

at least about 1 g/L of a polyol lipid;

at least one iron salt of a concentration in the range of about 0.001 mg/L to about 10 g/L; and at least one nitrogen source with a carbon to nitrogen ratio of about 30:1 to about 70:1;

whereby the basidiomycetous yeast cells produce one or more polyol lipids.

2. The method of claim 1, wherein said yeast cell culture further comprises one or more hydrophobic carbon sources.

3. The method of claim 1, wherein the culture comprises one or more hydrophilic carbon sources at a concentration in the range of about 0.2% (w/v) to about 50% (w/v).

4. The method of claim 1, wherein the nitrogen source is selected from the group consisting of ammonia, ammonium salt, nitrate, nitrite, nucleotides, nucleosides, proteins, peptides, amino acids, urea and its derivatives, and mixtures thereof, wherein the yeast culture comprises less than about 2% (w/v) nitrogen.

5. The method of claim 1, wherein the population of basidiomycetous yeast cells is from genera classified within the taxonomic order Sporidiobolales selected from the group consisting of *Rhodosporidiobolus, Rhodotorula*, and *Sporobolomyces*.

6. The method of claim 1, further comprising purifying and/or isolating the polyol lipids, wherein the polyol lipid can be purified and/or isolated without cell lysis and without solvent extraction.

7. The method of claim 1, wherein the one or more polyol lipid is a lipid selected from the group consisting of a 3-hydroxy fatty acid moiety from 10 to 24 carbon atoms in length, a sugar alcohol moiety esterified to the carboxyl end of a 3-hydroxy fatty acyl moiety, an acetylated 3-hydroxy fatty acyl moiety; acetylated, non-esterified hydroxy groups of a polyol lipid sugar alcohol moiety, a polyol lipid sugar alcohol moiety comprising a mannitol or arabitol backbone, and one or more polyol esters of fatty acid (PEFAs).

8. The method of claim 1, wherein the iron salt is selected from the group consisting of iron chloride (II) & (III), iron sulfate (II) & (III), iron nitrate (II) & (III), iron phosphate (II) & (III), fumarate, iron edetate, iron citrate, iron malate, iron oxalate, iron tartrate, iron succinate, iron acetate, in their anhydrous or their hydrated states, and organometallic complexes thereof.

* * * * *